US012257416B1

(12) United States Patent
Halpert et al.

(10) Patent No.: US 12,257,416 B1
(45) Date of Patent: Mar. 25, 2025

(54) FLUID THERAPY BASED ON SODIUM EXCRETION, AND ASSOCIATED SYSTEMS, DEVICES, AND METHODS

(71) Applicant: REPRIEVE CARDIOVASCULAR, INC., Milford, MA (US)

(72) Inventors: Andrew V. Halpert, Brookline, MA (US); Antony Jonathan Fields, San Francisco, CA (US); Jeffrey Testani, New Haven, CT (US)

(73) Assignee: Reprieve Cardiovascular, Inc., Milford, MA (US)

( * ) Notice: Subject to any disclaimer, the term of this patent is extended or adjusted under 35 U.S.C. 154(b) by 0 days.

(21) Appl. No.: 18/883,857

(22) Filed: Sep. 12, 2024

Related U.S. Application Data

(60) Provisional application No. 63/680,042, filed on Aug. 6, 2024, provisional application No. 63/582,218, filed on Sep. 12, 2023.

(51) Int. Cl.
*A61M 5/14* (2006.01)
*A61B 5/00* (2006.01)
*A61B 5/20* (2006.01)
*A61M 5/172* (2006.01)

(52) U.S. Cl.
CPC .......... *A61M 5/1407* (2013.01); *A61B 5/208* (2013.01); *A61B 5/4839* (2013.01); *A61M 5/1723* (2013.01)

(58) Field of Classification Search
CPC ....... A61B 5/4839; A61B 5/201; A61B 5/208; A61M 5/1407; A61M 5/1723
See application file for complete search history.

(56) References Cited

U.S. PATENT DOCUMENTS

| 3,954,010 | A | 5/1976 | Hilblom |
| 4,132,644 | A | 1/1979 | Kolberg |
| 4,146,029 | A | 3/1979 | Ellinwood, Jr. |
| 4,204,957 | A | 5/1980 | Weickhardt |
| 4,216,462 | A | 8/1980 | McGrath et al. |

(Continued)

FOREIGN PATENT DOCUMENTS

| EP | 0258690 | 3/1998 |
| EP | 1986007 | 10/2008 |

(Continued)

OTHER PUBLICATIONS

U.S. Appl. No. 16/544,975, filed Aug. 20, 2019, Levin.

(Continued)

*Primary Examiner* — Bradley J Osinski
(74) *Attorney, Agent, or Firm* — Perkins Coie LLP

(57) ABSTRACT

This present disclosure relates to fluid therapy based on sodium excretion, and associated systems, devices, and methods. Exemplary methods can include receiving a sodium excretion input for the patient; receiving a urine output rate; determining an adjusted urine output rate based on the sodium excretion input and the urine output rate; and providing fluid therapy based on the adjusted urine output rate. By determining the amount and/or rate of the infused diuretic and/or hydration fluid based on a patient's actual sodium excretion levels, embodiments of the present technology can optimize and/or customize all or a subset of a diuretic therapy to an individual patient's physiology.

28 Claims, 28 Drawing Sheets

(56) References Cited

U.S. PATENT DOCUMENTS

| | | | |
|---|---|---|---|
| 4,229,299 A | 10/1980 | Savitz et al. |
| 4,261,360 A | 4/1981 | Perez |
| 4,275,726 A | 6/1981 | Schael |
| 4,291,692 A | 9/1981 | Bowman et al. |
| 4,343,316 A | 8/1982 | Jespersen |
| 4,411,649 A | 10/1983 | Kamen |
| 4,448,207 A | 5/1984 | Parrish |
| 4,449,538 A | 5/1984 | Corbitt et al. |
| 4,504,263 A | 3/1985 | Steuer et al. |
| 4,658,834 A | 4/1987 | Blankenship et al. |
| 4,712,567 A | 12/1987 | Gille et al. |
| 4,728,333 A | 3/1988 | Masse et al. |
| 4,728,433 A | 3/1988 | Buck et al. |
| 4,813,925 A | 3/1989 | Anderson, Jr. et al. |
| 4,923,598 A | 5/1990 | Schal |
| 4,994,026 A | 2/1991 | Fecondini |
| 5,038,109 A * | 8/1991 | Goble .................. G01N 33/493 |
| | | | 324/692 |
| 5,098,379 A | 3/1992 | Conway et al. |
| 5,176,148 A | 1/1993 | Wiest et al. |
| 5,179,862 A | 1/1993 | Lynnworth |
| 5,207,642 A | 5/1993 | Orkin et al. |
| 5,573,506 A | 11/1996 | Vasko |
| 5,586,973 A | 12/1996 | Lemaire et al. |
| 5,709,670 A | 1/1998 | Vancaillie et al. |
| 5,722,947 A | 3/1998 | Jeppsson et al. |
| 5,769,087 A | 6/1998 | Westphal et al. |
| 5,814,009 A | 9/1998 | Wheatman |
| 5,891,051 A | 4/1999 | Han et al. |
| 5,910,252 A | 6/1999 | Truitt et al. |
| 5,916,153 A | 6/1999 | Rhea, Jr. |
| 5,916,195 A | 6/1999 | Eshel et al. |
| 5,981,051 A | 11/1999 | Motegi et al. |
| 5,984,893 A | 11/1999 | Ward |
| 6,010,454 A | 1/2000 | Arieff et al. |
| 6,171,253 B1 | 1/2001 | Bullister et al. |
| 6,231,551 B1 | 5/2001 | Barbut |
| 6,272,930 B1 | 8/2001 | Crozafon |
| 6,514,226 B1 | 2/2003 | Levin et al. |
| 6,531,551 B2 | 3/2003 | Ohno et al. |
| 6,537,244 B2 | 3/2003 | Paukovits et al. |
| 6,554,791 B1 | 4/2003 | Cartledge et al. |
| 6,640,649 B1 | 11/2003 | Paz et al. |
| 6,740,072 B2 | 5/2004 | Starkweather et al. |
| 6,752,779 B2 | 6/2004 | Paukovits et al. |
| 6,796,960 B2 | 9/2004 | Cioanta et al. |
| 6,827,702 B2 | 12/2004 | Lebel et al. |
| 6,942,637 B2 | 9/2005 | Cartledge et al. |
| 7,029,456 B2 | 4/2006 | Ware et al. |
| 7,044,002 B2 | 5/2006 | Ericson et al. |
| 7,086,615 B2 | 8/2006 | Joseph |
| 7,137,964 B2 | 11/2006 | Flaherty |
| 7,278,983 B2 | 10/2007 | Ireland et al. |
| 7,727,222 B2 | 6/2010 | Da Silva |
| 7,736,354 B2 | 6/2010 | Gelfand |
| 7,739,921 B1 | 6/2010 | Babcock |
| 7,758,562 B2 | 7/2010 | Gelfand |
| 7,758,563 B2 | 7/2010 | Gelfand |
| 7,837,667 B2 | 11/2010 | Gelfand |
| 7,938,817 B2 | 5/2011 | Gelfand |
| 8,007,460 B2 | 8/2011 | Gelfand |
| 8,075,513 B2 | 12/2011 | Rudko et al. |
| 8,233,957 B2 | 7/2012 | Merz et al. |
| 8,444,623 B2 | 5/2013 | Gelfand |
| 8,556,846 B2 | 10/2013 | O'Mahony et al. |
| 8,714,030 B1 | 5/2014 | Liu |
| 9,526,833 B2 | 12/2016 | Gelfand et al. |
| 10,045,734 B2 | 8/2018 | Da Silva |
| 10,537,281 B2 | 1/2020 | Thompson et al. |
| 10,639,419 B2 | 5/2020 | Halpert |
| 10,881,774 B2 | 1/2021 | Halpert |
| 11,064,939 B2 | 7/2021 | Da Silva |
| 11,213,621 B2 | 1/2022 | Halpert |
| 11,357,446 B2 | 6/2022 | Levin et al. |
| 11,633,137 B2 | 4/2023 | Conley et al. |
| 11,696,985 B2 | 7/2023 | Halpert |
| 11,950,925 B2 | 4/2024 | Levin |
| 11,986,302 B2 | 5/2024 | Conley et al. |
| 11,992,332 B2 | 5/2024 | Da Silva |
| 2001/0029340 A1 | 10/2001 | Mault et al. |
| 2002/0025597 A1 | 2/2002 | Matsuda |
| 2002/0072647 A1 | 6/2002 | Schock et al. |
| 2002/0107536 A1 | 8/2002 | Hussein |
| 2002/0151834 A1 | 10/2002 | Utterberg |
| 2002/0161314 A1 | 10/2002 | Sarajarvi |
| 2003/0040700 A1 | 2/2003 | Hickle |
| 2003/0048185 A1 | 3/2003 | Citrenbaum et al. |
| 2003/0048432 A1 | 3/2003 | Jeng et al. |
| 2003/0114786 A1 | 6/2003 | Hiller et al. |
| 2004/0025597 A1 | 2/2004 | Ericson et al. |
| 2004/0059295 A1 | 3/2004 | Cartledge et al. |
| 2004/0081585 A1 | 4/2004 | Reid |
| 2004/0087894 A1 | 5/2004 | Flaherty |
| 2004/0122353 A1 | 6/2004 | Shahmirian et al. |
| 2004/0133187 A1 | 7/2004 | Hickle |
| 2004/0163655 A1 | 8/2004 | Gelfand et al. |
| 2004/0167415 A1 | 8/2004 | Gelfand |
| 2004/0167464 A1 | 8/2004 | Ireland et al. |
| 2004/0176703 A1 | 9/2004 | Christensen et al. |
| 2004/0193328 A1 | 9/2004 | Zaitsu et al. |
| 2004/0243075 A1 | 12/2004 | Harvie |
| 2005/0027254 A1 | 2/2005 | Vasko |
| 2005/0065464 A1 | 3/2005 | Talbot et al. |
| 2005/0085760 A1 | 4/2005 | Ware et al. |
| 2006/0052764 A1 | 3/2006 | Gelfand et al. |
| 2006/0064053 A1 | 3/2006 | Bollish et al. |
| 2006/0100743 A1 | 5/2006 | Townsend et al. |
| 2006/0184084 A1 | 8/2006 | Ware et al. |
| 2006/0235353 A1 | 10/2006 | Gelfand et al. |
| 2006/0253064 A1 | 11/2006 | Gelfand et al. |
| 2006/0270971 A1 | 11/2006 | Gelfand et al. |
| 2007/0055198 A1 | 3/2007 | O'Mahony et al. |
| 2007/0088333 A1 | 4/2007 | Levin et al. |
| 2008/0027409 A1 | 1/2008 | Rudko et al. |
| 2008/0033394 A1 | 2/2008 | Gelfand et al. |
| 2008/0051764 A1 | 2/2008 | Dent et al. |
| 2008/0171966 A1 | 7/2008 | Rudko et al. |
| 2008/0221512 A1 | 9/2008 | Da Silva et al. |
| 2009/0054745 A1 | 2/2009 | Jennewine |
| 2009/0062730 A1 | 3/2009 | Woo |
| 2010/0133510 A1 | 6/2010 | Kim et al. |
| 2010/0185175 A1* | 7/2010 | Kamen .................. A61M 5/142 |
| | | | 604/67 |
| 2010/0280443 A1 | 11/2010 | Gelfand et al. |
| 2010/0280444 A1 | 11/2010 | Gelfand et al. |
| 2010/0286559 A1 | 11/2010 | Paz et al. |
| 2010/0312039 A1 | 12/2010 | Quirico |
| 2011/0046514 A1 | 2/2011 | Greenwald et al. |
| 2011/0046516 A1 | 2/2011 | Paz et al. |
| 2011/0120231 A1 | 5/2011 | Berger |
| 2011/0196304 A1 | 8/2011 | Kramer et al. |
| 2011/0218411 A1 | 9/2011 | Keenan |
| 2011/0288524 A1 | 11/2011 | Gelfand et al. |
| 2012/0078137 A1 | 3/2012 | Mendels |
| 2012/0259308 A1 | 10/2012 | Gelfand |
| 2013/0104667 A1 | 5/2013 | Koyano |
| 2013/0235691 A1 | 9/2013 | Volker |
| 2013/0261412 A1 | 10/2013 | Reed |
| 2013/0274705 A1 | 10/2013 | Burnes et al. |
| 2014/0031787 A1 | 1/2014 | Burnes et al. |
| 2014/0073973 A1 | 3/2014 | Sexton |
| 2014/0228755 A1 | 8/2014 | Darrah et al. |
| 2014/0260600 A1 | 9/2014 | Rike |
| 2014/0366641 A1 | 12/2014 | Jedema et al. |
| 2015/0105694 A1 | 4/2015 | Mahajan |
| 2015/0233749 A1 | 8/2015 | Wang et al. |
| 2015/0258277 A1 | 9/2015 | Halpert |
| 2016/0051176 A1 | 2/2016 | Ramos et al. |
| 2016/0051750 A1 | 2/2016 | Tsoukalis |
| 2016/0136356 A1 | 5/2016 | Ribble et al. |
| 2017/0016755 A1 | 1/2017 | Boussange et al. |
| 2017/0052056 A1 | 2/2017 | Yamasaki et al. |
| 2017/0290974 A1 | 10/2017 | Tsoukalis |
| 2018/0071455 A9 | 3/2018 | Halpert |

(56) References Cited

U.S. PATENT DOCUMENTS

| | | | |
|---|---|---|---|
| 2018/0110455 A1 | 4/2018 | Chang et al. | |
| 2018/0177945 A1 | 6/2018 | Sims et al. | |
| 2018/0245967 A1 | 8/2018 | Parker et al. | |
| 2018/0280620 A1 | 10/2018 | Reichthalhammer | |
| 2019/0001057 A1 | 1/2019 | Tsoukalis | |
| 2019/0038833 A1 | 2/2019 | Pirazzoli et al. | |
| 2019/0046723 A1* | 2/2019 | Halpert | A61B 5/20 |
| 2019/0262532 A1 | 8/2019 | Oh et al. | |
| 2019/0321588 A1 | 10/2019 | Burnett | |
| 2020/0230351 A1 | 7/2020 | Kelly et al. | |
| 2020/0324044 A1 | 10/2020 | Gylland et al. | |
| 2020/0360604 A1 | 11/2020 | Kolko et al. | |
| 2020/0284234 A1 | 12/2020 | Niland | |
| 2020/0405955 A1 | 12/2020 | Shah et al. | |
| 2021/0077007 A1 | 3/2021 | Jouret et al. | |
| 2021/0085853 A1 | 3/2021 | Chen et al. | |
| 2021/0128815 A1 | 5/2021 | Byrne et al. | |
| 2021/0162188 A1 | 6/2021 | Cui | |
| 2021/0169408 A1 | 6/2021 | Levin | |
| 2021/0170084 A1 | 6/2021 | Zacharia | |
| 2021/0196880 A1 | 7/2021 | O'Mahony et al. | |
| 2021/0236727 A1 | 8/2021 | Levin et al. | |
| 2021/0244381 A1 | 8/2021 | Sweeney et al. | |
| 2021/0260306 A1 | 8/2021 | Gravenstein et al. | |
| 2021/0283357 A1 | 9/2021 | Leonard | |
| 2021/0298653 A1 | 9/2021 | Woodward et al. | |
| 2021/0369959 A1 | 12/2021 | Abal et al. | |
| 2022/0152302 A1 | 5/2022 | Halpert | |
| 2022/0273213 A1 | 9/2022 | Sokolov | |
| 2022/0288362 A1 | 9/2022 | Porter et al. | |
| 2022/0296406 A1 | 9/2022 | Keelen | |
| 2022/0313158 A1 | 10/2022 | Levin et al. | |
| 2022/0330866 A1 | 10/2022 | Conley et al. | |
| 2022/0330867 A1 | 10/2022 | Conley et al. | |
| 2022/0339622 A1 | 10/2022 | Halpert | |
| 2023/0010793 A1 | 1/2023 | Testani | |
| 2023/0068431 A1 | 3/2023 | Erbey, II et al. | |
| 2023/0414871 A1 | 12/2023 | Halpert | |
| 2024/0260874 A1 | 2/2024 | Halpert | |

FOREIGN PATENT DOCUMENTS

| | | |
|---|---|---|
| EP | 3278833 | 2/2018 |
| EP | 4108171 | 12/2022 |
| GB | 2560580 | 9/2018 |
| JP | 2008110150 | 5/2008 |
| JP | A-2011-520549 | 7/2011 |
| JP | A-2017-536857 | 2/2017 |
| KR | 10-2022-0035738 | 3/2022 |
| WO | WO-1996016685 | 6/1996 |
| WO | WO-1996028209 | 9/1996 |
| WO | WO-1997016220 | 5/1997 |
| WO | WO-1999006087 | 2/1999 |
| WO | WO-2005102441 | 11/2005 |
| WO | WO-2006041496 | 4/2006 |
| WO | WO-2009029899 | 3/2009 |
| WO | WO-2013154783 | 10/2013 |
| WO | WO-2014022422 | 2/2014 |
| WO | WO-2015142617 | 9/2015 |
| WO | WO-2016103256 | 6/2016 |
| WO | WO-2018114794 | 6/2018 |
| WO | WO-2019222485 | 11/2019 |
| WO | WO-2020033752 | 2/2020 |
| WO | 2021205345 | 10/2021 |
| WO | WO-2022219578 | 10/2022 |

OTHER PUBLICATIONS

U.S. Appl. No. 18/595,182, filed Mar. 4, 2024, Levin.
U.S. Appl. No. 18/637,340, filed Apr. 16, 2024, Conley et al.
U.S. Appl. No. 18/641,241, filed Apr. 19, 2024, Da Silva.
U.S. Appl. No. 18/883,857, filed Sep. 12, 2024, Halpert.

"2016 ESC Guidelines for the Diagnosis and Treatment of Acute and Chronic Heart Failure—Web Addenda," European Heart Journal, 17 pages.
Adams et al., "Executive Summary: HFSA 2006 Comprehensive Heart Failure Practice Guideline," Journal of Cardiac Failure, vol. 12, No. 1, 2006, pp. 10-38.
Adaptec Medical Devices, "Ongoing Access to Real-Time And Accurate Monitoring of Urine Output Could Improve Management of Critically Ill Patients," Clinical Literature Review, (2016) 8 pages.
Allen et al., "Continuous Versus Bolus Dosing of Furosemide for Patients Hospitalized for Heart Failure," American Journal of Cardiology, 105(12):1794-1794, 2010.
Baliga, "Diuretic Therapy for Heart Failure Patients," American College of Cardiology, 75:1178-1195, 2020.
Bart et al., "Ultrafiltration in Decompensated Heart Failure With Cardiorenal Syndrome", The New England Journal of Medicine, Dec. 13, 2012, 9 pages, Massachusetts Medical Society.
Bell et al., "Risk of Postoperative Acute Kidney Injury in Patients Undergoing Orthopaedic Surgery—Development and Validation of Risk score and Effect of Acute Kidney Injury on Survival: Observational Cohort Study," BMJ: 2015, 9 pages.
Bouman et al., "Red Blood Cell Transfusion and Furosemide in Cardiac Surgery: Friend and Foe?" The Netherlands Journal of Medicine, Dec. 2012, vol. 70, No. 10, 3 pages.
Brater, "Diuretic Therapy," New England Journal of Medicine, 339:387-395, 1998.
Brezis et al., Hypoxia of the Renal Medulla—Its Implications for Disease, New England Journal of Medicine, vol. 322, No. 10, Mar. 9, 1995, 9 pages.
Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, 10 pages.
Conradds, "Sensitivity and Positive Predictive Value of Implantable Intrathoracic Impedance Monitoring as a Predictor of Heart Failure Hospitalizations: The SENSE-HF Trial," European Heart Journal (2011) 32, 2266-2273, 8pages.
Cosgrove III et al., "Automated Control Postoperative Hypertension: a Prospective Randomized Multicenter Study," 1989 by The Society of Thoracic Surgeons, 6 pages.
Dorval et al., "Feasibility Study of the RenalGuard™ Balanced Hydration System: a Novel Strategy for the Prevention of Contrast-Induced Nephropathy in High Risk Patients", International Journal of Cardiology, 2011, 5 pages, Elsevier Ireland Ltd.
Doty et al., Effect of Increased Renal Venous Pressure on Renal Function, The Journal of Trauma: Injury, Infection and Critical Care, vol. 47, No. 6, Dec. 1999, 4 pages.
Edelson et al., Pharmacokinetics of Iohexol, a New Nonionic Radiocontrast Agent, in Humans, Journal of Pharmaceutical Sciences, vol. 73, No. 7, Jul. 1984, 3 pages.
Ellison et al., "Diuretic Treatment in Heart Failure," New England Journal of Medicine, 377:1964-1975, 2017.
Farcy, "Review: Pitfalls in Using Central Venous Pressure as a Marker of Fluid Responsiveness," Emergency Medicine. Jan. 2016;48(1):18-28, 15 pages.
Farkas, "Deresuscitation: Dominating the Diuresis," The Internet Book of Critical Care, 43 pages, 2020.
Felker et al., "Diuretic Strategies in Patients With Acute Decompensated Heart Failure", The New England Journal of Medicine, Mar. 3, 2011, vol. 364, No. 9, 9 pages.
Furutani et al., "An Automatic Control System of the Blood Pressure of Patients Under Surgical Operation," International Journal of Control, Automation, and Systems, vol. 2, No. 1, Mar. 2004, pp. 39-54.
Gheorghiade et al., "Current Medical Therapy for Advanced Heart Failure," American Heart Journal, Jun. 1998, pp. S231-S248.
Gloor, James M. and Vincente E. Torres, Reflux and Obstructive Nephropathy, Atlas of Diseases of the Kidney, on-line edition, vol. Two, Section I, Ch. 8, pp. 8.1-8.25, 1999, 27 pages.
Goren et al., "Perioperative Acute Kidney Injury," British Journal of Anaesthesia, 2015, 12 pages.

(56) References Cited

OTHER PUBLICATIONS

Hasselblad et al., "Relation Between Dose of Loop Diuretics and Outcomes in a Heart Failure Population: Results of the ESCAPE Trial", European Journal of Heart Failure, 9(10):1064-1069, 2007.

Heyman et al., Pathophysiology of Radiocontrast Nephropathy: a Role for Medullary Hypoxia, Investigative Radiology, vol. 34, No. 11, Nov. 1999, 7 pages.

Hvistendahl et al., Renal Hemodynamic Response to Gradated Ureter Obstruction in the Pig, Nephron 1996, 74:168-74, 7 pages.

Jin et al., "Intensive Monitoring of Urine Output is Associated With Increased Detection of Acute Kidney Injury and Improved Outcomes," Chest Journal—Original Research Critical Care, 152#5, pp. 972-979 (Nov. 2017) 8 pages.

Josephs et al., "Perioperative Risk Assessment, Prevention, and Treatment of Acute Kidney Injury," International Anesthesiology Clinics, vol. 47, No. 4, www.anesthesiaclinics.com, pp. 89-105.

Kalantari, "Assessment of Intravascular Volume Status and Volume Responsiveness in Critically Ill Patients," Kidney International (2013) 83, 1017-1028 (Jan. 9, 2013) 12 pages.

Kolh, "Renal Insufficiency After Cardiac Surgery: a Challenging Clinical Problem," European Heart Journal, 2009, pp. 1824-1827.

Lara, "Accurate Monitoring of Intravascular Fluid Volume: a Novel Application of Intrathoracic Impedance Measures For the Guidance of Volume Reduction Therapy," IJC Heart & Vasculature, 8 (2015) pp. 47-51, 5pages.

Lassnigg et al., "Lack of Renoprotective Effects of Dopamine and Furosemide During Cardiac Surgery," J. Am Soc Nephrol, 2000, pp. 97-104.

Lelarge et al., Acute Unilateral Renal Failure and Contralateral Ureteral Obstruction, American Journal of Kidney Diseases, vol. XX, No. 3, Sep. 1992, 3 pages.

Lenihan et al., "Trends in Acute Kidney Injury, Associated Use of Dialysis and Mortality After Cardiac Surgery, 1999 to 2008," Ann Thorac Surg. 2013, 17 pages.

Levin et al. High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, 1 page.

Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, 161 pages.

Magder et al., "The Clinical Role of Central Venous Pressure Measurements", Journal of Intensive Care Medicine 22(1); 207, 8 pages.

Marenzi et al., "Prevention of Contrast Nephropathy by Furosemide With Matched Hydration," JACC: Cardiovascular Interventions, 5(1):90-97, 2011.

Marenzi et al.. "Prevention of Contrast Nephropathy by Furosemide With matched Hydration. The MYTHOS (Induced Diuresis With Matched Hydration Compared to Standard Hydration for Contrast Induced Nephropathy Prevention) Trial", JACC: Cardiovascular Interventions, vol. 5, No. 1, 2012 The American College of Cardiology Foundation, 8 pages.

Mawer et al., "Value of Forced Diuresis in Acute Barbiturate Poisoning", Jun. 29, 1968, British Medical Journal, 2, 4 pages.

Mayo Clinic, "Creatinine Test", Mayo Foundation for Medical Education and Research (MFMER) (downloaded Aug. 16, 2018).

Meersch et al., "Perioperative Acute Kidney Injury: An Under-Recognized Problem," vol. 125, No. 4, www.anesthesia-analgesia. org, Oct. 2017, pp. 1223-1232.

Mendeley et al., "Furosemide", Science Direct, 5 pages, 2016.

Oh et al., "Loop Diuretics in Clinical Practice," Review: Electrolyte Blood Press, 13(1): 5 pages, 2015.

Olivero et al., "Acute Kidney Injury After Cardiovascular Surgery: an Overview," debakeyheartcenter.com/journal, 2012, pp. 31-36.

Otero, "A New Device to Automate the Monitoring of Critical Patients' Urine Output", Hindawi Publishing Corp, BioMed Research Int'l, vol. 2014, Article ID 587593, 8 pages.

Palazzuli et al. "Continuous versus bolus intermittent loop diuretic infusion in acutely decompensated heart failure: a prospective randomized trial," Critical Care 18, 2014.

Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, 7 pages.

Pederson et al., Renal Water and Sodium Handling During Gradated Unilateral Ureter Obstruction, Scand J. Urol Nephrol, 2002, 36:163-72, 11 pages.

Prandota et al., "Pharmacokinetics and metabolism of furosemide in man," European Journal of Drug Metabolism and Pharmcokinetics, 1(4): 5 pages, 1976.

Rihal et al., Incidence and Prognostic Importance of Acute Renal Failure After Percutaneous Coronary Intervention, Circulation, May 14, 2002, 6 pages.

Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5, 4 pages.

Rosenberg et al., "Combination Therapy with Metolazone and Loop Diuretics in Outpatients with Refactory Heart Failure: an Observational Study and Review of the Literature," Cardiovascular Drugs and Therapy, Kluwer Academic Publishers, vol. 19, No. 4, Aug. 2005, 6 pages.

Rui Geng et al., "Identification of Modifiable Risk Factors for Acute Kidney Injury After Coronary Artery Bypass Graft Surgery in an Asian Population," The Journal of Thoracic and Cardiovascular Surgery, Apr. 2014, pp. 1356-1361.

S215 Ultra Low Profile Single Point Load Cell—Strain Guage Sensors and Load Cells, Ultra-Low Profile Single Point Load Cell—S215, http://smdsensors.com/detail_pgs/s215.htm 2005, 3 pages.

Se Won Oh et al., "Loop Diuretics in Clinical Practice", Electrolytes & Blood Pressure, www.ncbi.nlm.nih.gov/pmc/articles/PMC4520883, printed Mar. 25, 2019, 6 pages.

Shepherd, "Measuring and Managing Fluid Balance", Nursing Times, vol. 107, No. 28, pp. 12-16 (Jul. 19, 2011) 5 pages.

Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21, 5 pages.

Stevens, Melissa A., MD et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, 9 pages.

Stevenson et al., "Editorial Comment, Torrent or Torment From the Tubules?", Challenge of the Cardiorenal Connections, Journal of the American College of Cardiology, vol. 45, No. 12, 2005, 4 pages.

Stickler et al., "A Sensor to Detect the Early Stages in the Development of Crystalline Proteus mirabilis Biofilm on Indwelling Bladder Catheters", Journal of Clinical Microbiology, Apr. 2006, p. 1540-1542.

Teixeira et al., "Fluid Balance and Urine Volume are Independent Predictors of Mortality in Acute Kidney Injury", Critical Care 17:R14 (2013) 11 pages.

Testani et al., "Rapid and Highly Accurate Prediction of Poor Loop Diuretic Natriuretic Response in Patients with Heart Failure," Circulation; Heart Failure, vol. 9. No. 1, 2016, 32 pages.

Thakar, "Perioperative Acute Kidney Injury," Advances in Chronic Kidney Disease, vol. 20, No. 1, 2013, pp. 67-75.

Tricoli, "Miniaturized Bio-and Chemical-Sensors for Point-of-Care Monitoring of Chronic Kidney Diseases," Sensors 2018, 18, 942; (Mar. 22, 2018) 18 pages.

Unknown Author, "Furosemide Drug Summary," Prescriber's Digital Reference, pp. 1-31, 2016.

Vellinga et al., "Identification of Modifiable Risk Factors for Acute Kidney Injury After Cardiac Surgery," The Netherlands Journal of Medicine, vol. 70, No. 10, Dec. 2012, pp. 450-454.

Wakelkamp et al., The influence of drug input rate on the development of tolerance to frusemide, Br. J. Clin. Pharmacol 1998, 46:479-487, 9 pages.

(56) References Cited

OTHER PUBLICATIONS

Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415, pages.

Yeh et al., "Goal-directed diuresis: a case—control study of continuous furosemide infusion in critically ill trauma patients", The Journal of Emergencies, Trauma, and Shock, 8(1): 34-38, 2015.

Written Opinion of the International Searching Authority for PCT Application No. PCT/US2005/008948 dated Oct. 3, 2006, 3 pages.

Written Opinion of the International Searching Authority for PCT Application No. PCT/US2007/021791 dated May 8, 2008, 7 pages.

Written Opinion of the International Searching Authority for PCT Application No. PCT/U20S07/009685 dated Jul. 18, 2008, 10 pages.

Written Opinion of the International Searching Authority for PCT Application No. PCT/US2007/009684 dated Jul. 21, 2008, 7 pages.

Written Opinion of the International Searching Authority for PCT Application No. PCT/US2008/007845 dated Sep. 17, 2008, 5 pages.

Written Opinion of the International Searching Authority for PCT Application No. PCT/US2008/007841 dated Sep. 18, 2008 4 pages.

Written Opinion of the International Searching Authority for PCT Application No. PCT/US2007/009683 dated Nov. 24, 2008, 6 pages.

Written Opinion of the International Searching Authority for PCT Application No. PCT/US2009/002739 dated Jun. 19, 2009, 4 pages.

Written Opinion of the International Searching Authority for PCT Application No. PCT/US2010/000137 dated Mar. 16, 2010, 8 pages.

Written Opinion of the International Searching Authority for PCT Application No. PCT/US2015/020196, dated Jun. 12, 2015, 5 pages.

Phillips et al., "Measurement of sodium ion concentration in undiluted urine with cation-selective polymeric membrane electrodes after the removal of interfering compounds", Talanta, Elsevier, Amsterdam, NL, vol. 74, No. 2, Nov. 15, 2007, pp. 255-264.

International Search Report and Written Opinion for International Patent Application No. PCT/US24/46468, Applicant: Reprieve Cardiovascular, Inc., mailed Dec. 19, 2024, 15 pages.

\* cited by examiner

200 ⬊

```
        ┌─────────────────┐
        │  Treat Patient  │
        └────────┬────────┘
                 │
202 ⬊            ▼
┌─────────────────────────────────────────────────────┐
│      Obtaining a urine output rate from a patient    │
└─────────────────────────┬───────────────────────────┘
                          │
204 ⬊                     ▼
┌─────────────────────────────────────────────────────┐
│ Causing a diuretic to be provided to the patient at a dosage rate │
└─────────────────────────┬───────────────────────────┘
                          │
206 ⬊                     ▼
┌─────────────────────────────────────────────────────┐
│ Causing a hydration fluid to be provided to the patient at a hydration rate │
└─────────────────────────┬───────────────────────────┘
                          │
208 ⬊                     ▼
┌─────────────────────────────────────────────────────┐
│ Adjusting at least one of the dosage rate of the diuretic or the hydration rate of │
│ the hydration fluid, thereby causing net fluid loss from the patient │
└─────────────────────────────────────────────────────┘
```

```
         ( Treat Patient )
               │
               ▼
502 ┌─────────────────────────────────────────────────────────┐
    │ Obtaining a sodium excretion input for the patient      │
    └─────────────────────────────────────────────────────────┘
               │
               ▼
504 ┌─────────────────────────────────────────────────────────┐
    │ Obtaining a urine output rate of the patient            │
    └─────────────────────────────────────────────────────────┘
               │
               ▼
506 ┌─────────────────────────────────────────────────────────┐
    │ Determining an adjusted urine output rate based, at least in part, on the │
    │ sodium excretion input and the urine output rate        │
    └─────────────────────────────────────────────────────────┘
               │
               ▼
508 ┌─────────────────────────────────────────────────────────┐
    │ Providing fluid therapy based, at least in part, on the adjusted urine output rate │
    └─────────────────────────────────────────────────────────┘
```

*FIG. 5A*

FLUID THERAPY BASED ON SODIUM EXCRETION, AND ASSOCIATED SYSTEMS, DEVICES, AND METHODS

CROSS-REFERENCE TO RELATED APPLICATION

The present application claims priority to U.S. Provisional Application No. 63/582,218, filed Sep. 12, 2023, and U.S. Provisional Application No. 63/680,042, filed Aug. 6, 2024, the disclosures of which are hereby incorporated by reference in their entireties.

TECHNICAL FIELD

This present disclosure relates to fluid therapy based on adjusted urine output rate, and associated systems, devices, and methods.

BACKGROUND

Human physiological systems seek to naturally maintain a balance between fluid intake and fluid excretion. An imbalance in fluid intake and excretion rates may cause the body to retain excess amounts of fluid, also known as fluid overload. Fluid overload can be caused by acute decompensated heart failure (ADHF), chronic heart failure (CHF), or other conditions in which insufficient fluid is excreted. Patients exhibiting fluid overload may suffer from shortness of breath (dyspnea), edema, hypertension, and other undesirable medical conditions.

To treat fluid overload, patients are typically administered a diuretic drug which induces and/or increases urine production, thus reducing the amount of fluid and sodium in the body. The rate of urine output may be carefully monitored and/or controlled for safety reasons, e.g., to avoid placing undue stress on the patient's kidneys. Different patients may respond differently to treatment, such that the same diuretic type and/or dosage may produce drastically different urine output rates. However, conventional systems and methods for treating fluid overload may not be capable of accurately monitoring a patient's urine output and/or urine characteristics to respond to changes in urine output.

BRIEF DESCRIPTION OF THE DRAWINGS

Features, aspects, and advantages of the presently disclosed technology may be better understood with regard to the following drawings.

FIG. 2 is a flow diagram of a method for treating a patient, configured in accordance with embodiments of the present technology.

FIG. 5A is a flow diagram of a method for treating a patient based on an adjusted urine output rate, configured in accordance with embodiments of the present technology.

Figure 1:
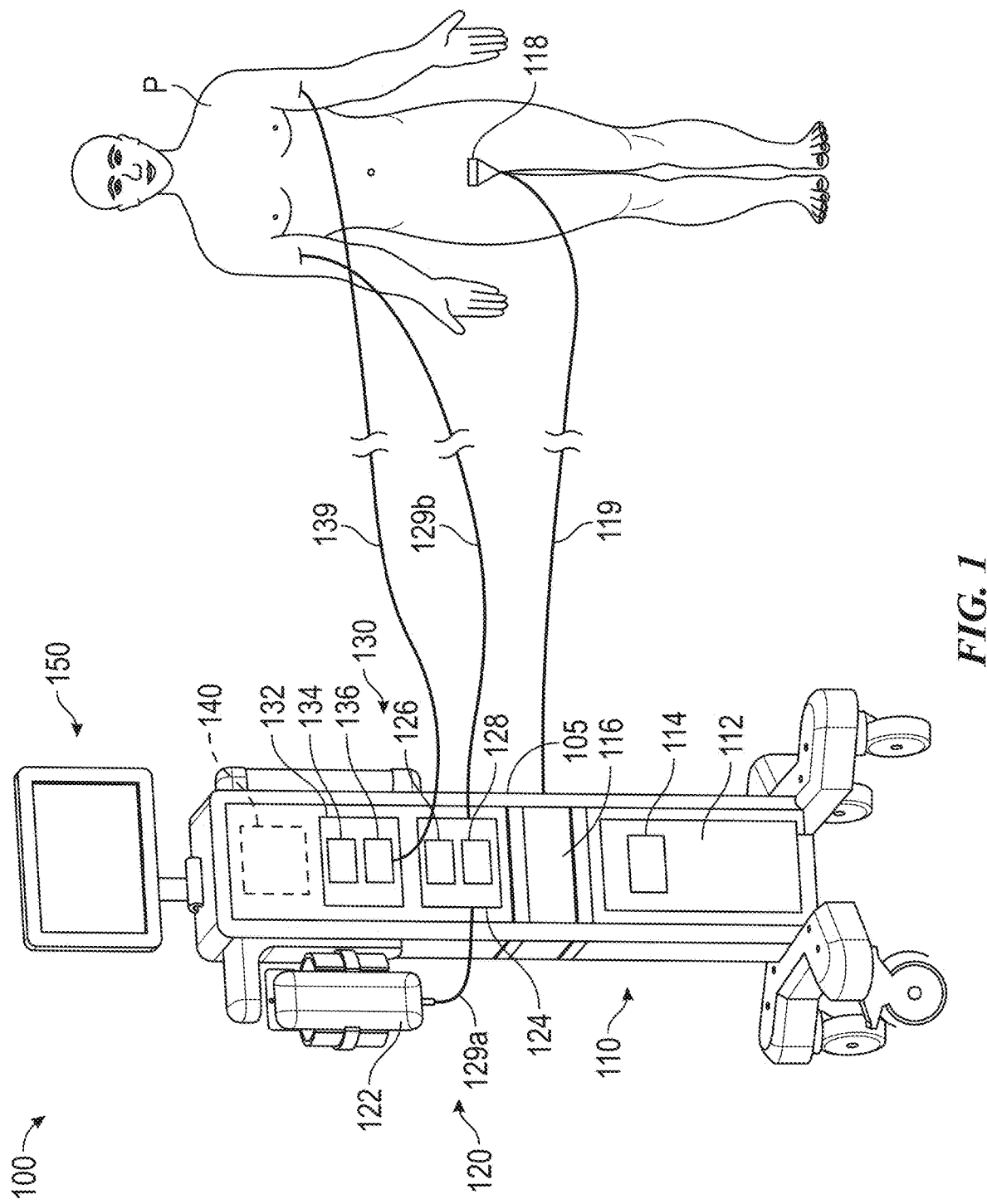
FIG. 1 is a partially schematic view of a fluid management system, configured in accordance with embodiments of the present technology.

A person skilled in the relevant art will understand that the features shown in the drawings are for purposes of illustrations, and variations, including different and/or additional features and arrangements thereof, are possible.

DETAILED DESCRIPTION

The headings provided herein are for convenience only and are not intended to limit or interpret the scope or meaning of the technology.

I. OVERVIEW

The present technology is directed to systems for managing (e.g., increasing or decreasing) a patient's urine and/or sodium output based on an adjusted urine output rate of the patient. The adjusted urine output rate can be determined based, at least in part, on a urine output of the patient (e.g., a volume and/or a rate of urine output) and a urine sodium level or sodium excretion of the patient (e.g., an amount, a concentration, and/or an excretion rate of sodium in the patient's urine). In some embodiments, an amount, concentration, or excretion rate of one or more other charged particles or compounds (e.g., chloride, charged ions, or combinations thereof) in the patient's urine can be determined in addition to or in lieu of determining sodium levels. As such, "sodium" as used herein can be replaced with one or more of chloride or charged ions. The adjusted urine output rate can, in turn, be used to determine an amount and/or rate of a diuretic and/or a hydration fluid administered to the patient during fluid therapy. In some embodiments, the patient's urine sodium excretion rate can be used to determine the amount and/or rate of the diuretic and/or the hydration fluid, e.g., instead of the adjusted urine output.

Some treatment protocols determine diuretic and/or hydration fluid infusion based on a standard or assumed sodium excretion. For example, some treatment protocols assume (e.g., do not measure) the concentration of sodium in the patient's urine and determine the amount and/or rate of the infused diuretic and/or hydration fluid based on the patient's urine output and the assumed urine sodium concentration. While a standardized treatment protocol can be effective for most patients, some patients may have a sodium excretion level (e.g., an actual urine sodium concentration) that is different (e.g., greater or lesser) than the assumed sodium excretion level, which can prevent or inhibit optimal therapy. As an example, certain patients may intake (e.g., drink) more fluids than stipulated during therapy which, in turn, naturally dilutes the sodium concentration in the urine of these patients and causes these patients to excrete urine with a lower than expected sodium concentration (e.g., even though the increased fluid intake may increase the volume of urine that the patient excretes). Infusing hydration fluid (e.g., saline) based on the assumed urine sodium concentration can lead to more hydration fluid (and thus more sodium) than required being infused into these patients. Because sodium naturally causes the body to retain water, one goal of fluid therapy is to reduce a patient's overall fluid balance by removing sodium, e.g., via urine. Accordingly, infusing excessive amounts of hydration fluid (and thus excess sodium) can prevent or inhibit optimal therapy by causing sodium to be removed at sub-optimal rates. Similarly, controlling diuretic therapy based on dilute urine output (e.g., low sodium urine) can cause the system to under-dose diuretic, which may also lead to sub-optimal sodium excretion and thus sub-optimal sodium removal. Providing fluid therapy based on a patient's measured urine sodium content can require a different set of therapeutic benchmarks for each of the various phases of fluid therapy. As such, modifying a system that operates based (e.g., solely based) on a patient's urine output rate to utilize the patient's measured urine sodium content (and/or the content of one or more other charged particles in the patient's urine, such as the patient's measured urine chloride content, and/or other surrogate values) can require a fundamental reworking of how that system was designed and intended to operate. In contrast, by determining the amount and/or rate of the infused diuretic and/or hydration fluid based on a patient's adjusted urine output, which takes into account the patient's actual and/or estimated sodium excretion levels, embodiments of the present technology can optimize and/or customize all or a subset of a diuretic therapy to an individual patient's physiology, for example, to maximize decongestion and/or minimize clinical sequelae. Moreover, by determining and providing fluid therapy based on a patient's adjusted urine output rate that factors in the patient's actual urine sodium content, embodiments of the present technology can continue to provide fluid therapy based on pre-existing urine output benchmarks and simply adjusting those benchmarks as needed to account for patient-to-patient variations in adjusted urine output rates.

II. FLUID MANAGEMENT SYSTEMS AND METHODS

The present technology is generally directed to systems, devices, and associated methods for fluid therapy based on patient data, including managing fluid levels of the patient based at least partially in response to data received from the patient before and/or during the fluid therapy. In some embodiments, the systems, devices, and methods described herein are used to treat a patient for fluid overload. To treat fluid overload, patients can be administered a diuretic drug which induces and/or increases urine production. For example, loop diuretics are diuretics that act at the ascending limb of the loop of Henle in the kidney, and include bumetanide (Bumex®), ethacrynic acid (Edecrin®), furosemide (Lasix®), torsemide (Demadex®), thiazide and thiazide-like diuretics (e.g., chlorothiazide, metolazone), potassium-sparing diuretics (e.g., amiloride, spironolactone), carbonic anhydrase inhibitors (e.g., acetazolamide), Vaptans (e.g., Conivaptan), SGLT2 inhibitors, and osmotic diuretics (e.g., mannitol). Diuretics can be given orally as a pill or as an intravenous (IV) injection. IV diuretics can be used when oral diuretics are no longer effective and/or able to be absorbed.

The short-term effects of diuretics on a patient's urine production may be difficult to predict, particularly at early stages of treatment. For example, one patient may produce much less urine than expected for a given dose of diuretic, while another patient administered the same dose may produce very large amounts of urine. Low urine production can prolong treatment time and/or reduce treatment efficacy, while high urine production can raise concerns of hypotension, hypovolemia, electrolyte imbalance (e.g., hypokalemia), and/or vital organ damage. High doses of a diuretic, regardless of the urine response, can also raise concerns about ototoxicity. Due to these uncertainties, physicians typically initially prescribe a conservative (e.g., low) diuretic dosage and often wait a full day before considering whether to increase the dosage. If the physician determines that a higher diuretic dosage is needed, the physician may slowly and incrementally increase the dosage until the patient's urine output reaches the desired level and/or rate. However, this approach can prolong the time the patient remains in the fluid overloaded condition, which can exacerbate the patient's underlying clinical state. For example, conservative treatment procedures can require hours or even days before the patient's urine output is sufficiently high to cause significant fluid loss and relieve the fluid overload condition. The patient may be hospitalized for several days (e.g., 4-5 days), which can be expensive and burdensome. Additionally, the long-term treatment efficacy may be limited, such that approximately 25% of patients are readmitted for fluid overload within 30 days.

To overcome these and other challenges, the present technology provides systems, and associated devices and methods, for managing a patient's fluid levels. In some embodiments, the present technology can (i) improve efficacy, safety, and quality of fluid management treatment, (ii) improve resource management in hospitals and other clinical settings, (iii) quickly assess if a patient is diuretic resistant (e.g., in the first few hours of treatment), and/or (iv) increase diuretic efficiency (e.g., the amount of urine and/or excreted electrolytes (e.g., sodium and/or chloride) obtained over a given time per mg of diuretic infused intravenously). The embodiments described herein can increase net removal of fluid and/or electrolytes (e.g., sodium and/or chloride), and can also treat fluid overload conditions in a more efficient manner (e.g., shorter timeframe and/or higher net fluid loss).

FIG. 1 is a partially schematic illustration of a fluid management system 100 ("system 100") for monitoring urine output and/or control fluid infusion into a patient P, in accordance with embodiments of the present technology. The system 100 includes a urine collection and monitoring system 110 ("urine system 110"), an automated hydration fluid infusion system 120 ("hydration system 120"), an automated diuretic infusion system 130 ("diuretic system 130"), a controller or control system 140 ("controller 140"), and a display or input/output unit 150 ("display 150"). The controller 140 can be operably coupled to each of the urine system 110, hydration system 120, diuretic system 130, and/or display 150. The system 100 can further include a console or structure 105 ("console 105") that incorporates, houses, and/or otherwise supports all or portions of the urine system 110, hydration system 120, diuretic system 130, the controller 140, and/or the display 150.

The urine system 110 is configured to collect urine from the patient P and/or monitor the patient's urine output (e.g., urine output amount and/or rates). The urine system 110 can include one or more collection containers 112 ("container 112") configured to hold urine, such as a disposable bag or other collection device. The container 112 can be fluidly coupled to the patient P via a fluid line 119 (e.g., a tubing line). The fluid line 119 can be connectable to a disposable catheter 118 (e.g., a Foley or other indwelling catheter, a non-indwelling catheter such as a Texas Condom catheter or a PureWick catheter, and/or one or more other catheters) placed in or otherwise connected to the bladder of the patient P.

In some embodiments, urine flow through the fluid line 119 is driven by the patient's urine production, gravity (e.g., the bladder of the patient P is positioned higher than the container 112), and/or a siphon effect between the patient's bladder and the container 112. In other embodiments, the urine system 110 can also include a pump (not shown) operably coupled to the fluid line 119 for actuating urine flow through the fluid line 119 and into the container 112. The pump can be or include any device suitable for pumping fluid, such as a peristaltic pump. The pump can be used to initiate urine flow from the patient's body at the start of the procedure. The pump can also be used to clear air locks and/or other obstructions from the fluid line 119.

The urine system 110 can include one or more sensors 114 ("sensor(s) 114") configured to detect characteristics of the patient's urine output (e.g., an amount and/or rate of urine output, and/or electrical, chemical, and/or physical properties of the patient's urine including, e.g., urine sodium concentration, urine conductivity, urine temperature, urine oxygen content, and/or combinations thereof). Accordingly, the sensor(s) 114 can generate data based at least partially on the patient's urine such that the controller 140 can monitor and/or compute the patient's urine output based on the data generated by the sensor(s) 114.

The urine output can be determined in many different ways, such as based on urine flow (e.g., through the fluid line 119 and/or into the container 112), the amount of urine in the container 112 (e.g., based on the weight of the container 112, level of urine in the container 112, and/or combinations thereof), and/or other properties associated with the urine. The sensor(s) 114 can include one or more of the following: a flow sensor, drip counter, fluid weight sensor, fluid level sensor, float sensor, optical sensor, ultrasonic sensor, and/or other sensors known in the art suitable for measuring a urine output amount and/or rate. In the embodiment of FIG. 1, the sensor(s) 114 are positioned at the console 105. In other embodiments, however, some or all of the sensor(s) 114 can be at a different location in the system 100, such as on or in the line 119, on or in the container 112, and/or on or in the patient P.

In some embodiments, the sensor(s) 114 can include at least one sensor configured to measure one or more characteristics of the urine, in addition to detecting the patient's urine output. For example, the sensor(s) 114 can be configured to measure urine temperature, urine conductivity, urine oxygenation, urine specific gravity, and/or levels of one or more analytes in the urine (e.g., creatinine, sodium, potassium, and/or combinations thereof). Such characteristics can be useful, e.g., in determining effectiveness of a particular therapy and/or whether the patient P is in or could be approaching a critical condition. For example, urine conductivity and/or urine electrolytes (e.g., sodium) can indicate whether the patient is responding well to the fluid therapy, or whether the patient is in a critical condition and fluid therapy should cease. In some embodiments, urine conductivity (either alone or in combination with urine specific gravity) is used as a proxy for measurements of urine sodium and/or other urine electrolytes, e.g., a higher urine conductivity can correlate to higher urine sodium levels and a lower urine conductivity can correlate to lower urine sodium levels. The urine conductivity and/or urine electrolyte levels can be used to determine a patient's actual urine sodium content and, accordingly, determine the patient's adjusted urine output rate. In some embodiments, the patient's actual urine sodium content can be measured directly by, e.g., one or more of the sensors 114. As another example, urine temperature measurements can be used to detect urine flow (e.g., based on heat loss through the fluid line 119). The urine temperature can also be used as a proxy for the patient's body temperature, which in turn can correlate to the patient's current clinical state.

Optionally, the sensor(s) 114 can include at least one sensor configured to monitor the status of the urine collection procedure, such as whether urine collection is proceeding normally, whether there are interruptions in urine flow, whether there is a blockage or leak in the urine system 110, and/or combinations thereof. For example, the sensor(s) 114 can include a leak sensor configured to detect whether a leakage is present in the urine system 110 (e.g., at or near the fluid line 119, catheter 118, and/or container 112). Leaks can be detected based on changes in urine flow rate, changes in pressure, the presence of moisture, or any other suitable parameter. In some embodiments, the controller 140 is configured to analyze the data from the leak sensor and/or other sensor(s) 114 to differentiate between low urine output rates versus leaks in the urine system 110.

As another example, the sensor(s) 114 can include a pressure sensor configured to measure the fluid pressure in the fluid line 119. The controller 140 can use the pressure measurements to monitor the status of urine flow, and optionally, detect whether there are any interruptions (e.g., decreases, sudden stoppages) or other issues with urine collection. In some embodiments, the controller 140 analyzes the pressure measurements to determine whether interruptions are due to low urine flow (e.g., the patient's bladder is empty or nearly empty), an air lock or other obstruction in the fluid line 119, a leak in the urine system 110 and/or a kink in the fluid line 119 and/or catheter 118. The controller 140 can alert the user if manual intervention is helpful or needed (e.g., to clear the obstruction, fix the leak, remove kinks from the fluid line 119, and/or combinations thereof). In embodiments where the urine system 110 includes a pump, the controller 140 can automatically activate the pump and/or increase the pumping rate to clear the obstruction from the fluid line 119.

The hydration system 120 can include at least one hydration fluid source 122 ("fluid source 122"—a bag, bottle, reservoir, and/or combinations thereof) containing a hydration fluid, such as saline (e.g., a premixed saline solution), Ringer's lactate solution, and/or other any other liquid solution configured to prevent or treat dehydration of the patient P. The hydration fluid can be isotonic, hypertonic, or hypotonic, e.g., depending on the patient's condition and/or other treatment considerations. Optionally, the composition of the hydration fluid (e.g., sodium, chloride, potassium, bicarbonate, other substances and/or compounds, and/or combinations thereof) can be varied based on the patient's condition and/or expected or measured electrolyte loss during the treatment procedure.

The fluid source 122 can be connected to the patient P via at least one fluid line (e.g., an IV line or other tubing), such as first fluid line 129a and a second fluid line 129b. The fluid source 122 can be operably coupled to one or more hydration fluid components 124 for actuating and/or monitoring hydration fluid infusion via the first and second fluid lines 129a-b, such as a hydration fluid pump 126 and/or at least one hydration fluid sensor 128 ("fluid sensor 128"). In the illustrated embodiment, the fluid source 122 is fluidly coupled to the hydration fluid pump 126 via the first fluid line 129a, and the hydration fluid pump 126 can pump the hydration fluid into the patient P via the second fluid line 129b. The hydration fluid pump 126 can be or include a peristaltic pump or other pump suitable for infusing a fluid into the patient's body (e.g., via an IV route or another route).

The fluid sensor 128 can be configured to determine an amount and/or rate of hydration fluid flowing from the fluid source 122 toward the patient P, and can include a flow sensor, pressure sensor, and/or other sensor configured to determine fluid output from the pump 126. Alternatively, or in combination, the fluid sensor 128 can monitor hydration infusion rate by measuring the pumping rate of the pump 126 (e.g., the number of rotations of the pump 126 per minute). As described elsewhere herein, the controller 140 can be operatively coupled to the hydration system 120 and can receive sensor data from the fluid sensor 128 to determine a hydration fluid infusion rate. The controller 140 can control the pumping rate of the pump 126 to control the amount and/or rate of hydration fluid provided to the patient P.

Optionally, the amount of hydration fluid in the fluid source 122 can be monitored, e.g., based on weight, volume, fluid levels, flow rates, and/or combinations thereof. In such embodiments, the fluid source 122 can be operably coupled to an additional sensor separate from the fluid sensor 128 (not shown), such as a fluid level monitor, float sensor, weight sensor, optical sensor, drip counter, flow measurement sensor, or the like. The additional sensor can provide an independent source of measurement data for determining and/or verifying the amount and/or rate of hydration fluid being provided to the patient P, which can be helpful for improving measurement accuracy.

In some embodiments, the hydration system 120 includes at least one sensor configured to detect the presence of the fluid source 122, such as a location sensor, optical sensor, weight sensor, one or more other sensors, and/or combinations thereof. The hydration system 120 can use the sensor data to automatically determine whether the fluid source 122 is present or absent, e.g., to assess whether the system 100 is ready to initiate the fluid therapy treatment. Optionally, the sensor data can be used to detect if the user is removing the fluid source 122 during the treatment procedure, e.g., to switch an empty or nearly empty fluid source 122 with a new fluid source 122. In such embodiments, the system 100 can automatically pause hydration fluid infusion until the fluid source 122 has been replaced. Accordingly, the user can switch fluid sources 122 without having to inform the system 100 or manually pause the procedure.

The diuretic system 130 can be configured to automatically provide a diuretic to the patient P. The diuretic system 130 can include a diuretic source 134 (e.g., syringe, bag, reservoir, and/or combinations thereof) containing a diuretic, such as bumetanide (Bumex®), ethacrynic acid (Edecrin®), furosemide (Lasix®), torsemide (Demadex®), and/or other diuretics known in the art, each of which may be part of a fluid solution (e.g., a mixture of saline and a diuretic or other agent). In some embodiments, the identity and/or concentration of the diuretic can be received by the controller 140 via user input (e.g., using the display 150), by scanning a barcode of the diuretic source 134 or other container of the diuretic, and/or any other suitable technique.

The diuretic source 134 can be connected to the patient P via a fluid line 139 (e.g., an IV line or other tubing). The diuretic source 134 can also be operably coupled to one or more diuretic components 136 for actuating and/or monitoring diuretic delivery via the fluid line 139. For example, the diuretic components 136 can include a diuretic pump configured to pump the diuretic through the fluid line 139 and toward the patient P. The diuretic pump can include a peristaltic pump, a syringe pump, a metering pump, or other device suitable for delivering the diuretic to the patient P at a plurality of dosage rates. The diuretic pump can deliver the diuretic according to any suitable delivery profile, such as at a controlled continuous rate and/or in controlled boluses delivered at regular intervals through the fluid line 139.

In some embodiments, the diuretic pump is or includes a syringe pump having a mechanical injector or plunger that is operably coupled to the controller 140, such that the controller 140 causes movement of the injector to transfer the diuretic to the patient P. The syringe pump can include or be coupled to an actuator that mechanically drives the injector to control the delivery of the diuretic to the patient P. For example, the actuator can be or include a mechanical actuator, such as a nut for rotating a screw to drive the injector. The syringe pump can also include or be operably coupled to a sensor for detecting the position of the injector. Alternatively, or in combination, the diuretic pump can include other types of pumps and/or actuators. For example, the diuretic pump can include a motor, a gearbox operatively connected to the motor, a sensor for measuring rotation of said motor (e.g., a tachometer or an optical encoder), and/or a microcontroller configured to control operation of the motor and monitor the quantity of diuretic delivered to the patient P. As another example, the diuretic pump can include an electric motor, such as a rotary motor, a linear motor, and/or a series of electrically actuated solenoids configured to propel liquid from the diuretic source 134 and through the line 139 toward the patient P.

In some embodiments, the diuretic components 136 include one or more diuretic sensors configured to determine an amount and/or rate of diuretic flowing toward the patient P. The one or more diuretic sensors can include, for example, a flow sensor, weight sensor, and/or other sensor type configured to determine the amount and/or rate of diuretic delivered from the diuretic source 134. Optionally, the diuretic sensors can measure diuretic delivery based on the output from the diuretic pump, such as by monitoring the pumping rate (e.g., number of rotations of the diuretic pump per minute, plunger position, and/or combinations thereof). The diuretic components 136 can include additional functional components, such as an air bubble detector, pressure sensor, extravasation sensor (e.g., ivWatch device), and/or other embedded electronics, e.g., to provide feedback signals to the controller 140 to ensure accurate diuretic infusion and/or monitor infusion status.

The controller 140 is configured to automatically control hydration fluid and/or diuretic infusion (e.g., based at least in part on the patient's urine output) to promote safe and effective diuresis of the patient P. The controller 140 can include one or more processor(s) and tangible, non-transient memory configured to store programmable instructions. The controller 140 can be operably coupled to the urine system 110, hydration system 120 and/or diuretic system 130 to receive data (e.g., sensor data) from and transmit data (e.g., control signals) to the various components of these systems. For example, the controller 140 can receive sensor data from the urine system 110 (e.g., from sensor(s) 114) to determine and/or monitor the patient's urine output (including, e.g., the patient's adjusted urine output rate). Based on the urine output, the controller 140 can determine an appropriate diuretic dosage amount and/or rate to administer to the patient P, and can cause the diuretic system 130 to deliver the diuretic accordingly. For example, the controller 140 can determine a pumping rate of the diuretic pump to produce the desired delivery profile for the diuretic. Similarly, the controller 140 can determine an appropriate hydration fluid infusion rate for the patient P (e.g., based on the urine output and/or the diuretic dosage rate), and can cause the hydration system 120 to deliver the appropriate hydration fluid amount and/or rate. For example, the controller 140 can determine a pumping rate for the hydration fluid pump 126 to achieve the desired hydration fluid infusion rate. The controller 140 can regulate the diuretic dosage rate and/or hydration fluid infusion rates based on a suitable treatment regimen protocol, e.g., prescribed by a physician and/or managed by the controller 140.

During the procedure, the controller 140 can receive sensor data from the various sensors of the urine system 110, hydration system 120 and/or diuretic system 130 to monitor the urine output, hydration fluid infusion rate, and/or diuretic dosage rate, respectively. The controller 140 can also receive sensor data from additional sensors configured to monitor patient status and/or operational status of the system 100, such as fluid pressure sensors, blood pressure sensors, air bubble detectors, analyte detectors, and the like. For example, the controller 140 can be operably coupled to at least one sensor implanted in, attached to, or otherwise associated with the patient P. The sensor(s) can provide data regarding any of the following patient parameters: pressure levels (e.g., pulmonary artery pressure, left atrial pressure), bioelectric measurements (e.g., bioimpedance vector analysis (BIVA)), hemoglobin measurements (e.g., non-invasive hemoglobin measurements), urine oxygenation levels, urine composition (e.g., creatinine, sodium, potassium, chloride, and/or one or more other substances and/or compounds), urine temperature, body temperature (e.g., bladder temperature), oral fluid intake, heart rate, heart rate variability, blood oxygenation, hematocrit, hemodynamic data, and any other data described herein. The controller 140 can use the data from any of the sensors described herein to monitor treatment progress (e.g., whether the treatment is complete), patient status (e.g., whether the patient is responding well or poorly to treatment), and/or potential safety concerns (e.g., whether the diuresis is too aggressive, whether the patient is exhibiting side effects). The controller 140 can also adjust the hydration fluid infusion rate and/or diuretic dosage rate based on the sensor data. Additionally, the sensor data can also provide feedback to the controller 140 to confirm or verify the effectiveness of the fluid therapy.

The controller 140 can also use other data for monitoring and/or controlling the therapy, such as settings for the system 100, user input, data indicative of a desired treatment regimen (e.g., a programmed diuretic and/or hydration fluid delivery profile over time), and/or other data collected or calculated by the controller 140. In some embodiments, the data used by the controller 140 includes current and/or historical data for the patient P, such as diuretic dosages delivered to the patient P, urine output volume or rate, the amount of hydration fluid infused into the patient P, the weight or change in weight of the patient P at various times during the infusion of the diuretic, indicators of the patient's renal function (e.g., estimated glomerular Filtration Rate (eGFR)), and/or the time(s) during which the patient P was treated with the system 100. Additionally or alternatively, the data used by the controller 140 can include historical data for one or more other patients, as described elsewhere herein.

The display 150 (e.g., a touchscreen, monitor, and/or one or more other display devices) can include a user interface configured to receive inputs from the user and display outputs to the user. In some embodiments, the display 150 is operatively coupled to the controller 140 and thus can be used to receive user input indicating treatment parameters, such as parameters for urine output, hydration fluid infusion, and/or diuretic dosage. The treatment parameters can include, for example: a desired fluid balance level (e.g., a positive, negative, or neutral fluid balance), estimated excess fluid volume, target fluid removal volume (e.g., minimum and/or maximum amount of fluid to be removed), desired urine output level (e.g., a total amount of urine output; a target maximum, minimum, and/or average urine output rate), treatment duration (e.g., maximum and/or minimum duration of the treatment procedure; planned duration of the input balance level and/or urine output level), hydration fluid type, hydration fluid infusion rate (e.g., maximum, minimum, and/or average infusion rate), hydration fluid infusion profile (e.g., a function indicating how the amount and/or rate of hydration fluid infusion should vary over time), time limits associated with hydration fluid infusion (e.g., maximum and/or minimum time period for hydration fluid infusion), diuretic type, diuretic dosage (e.g., maximum and/or minimum dosage), diuretic dosage rate (e.g., maximum, minimum, and/or average dosage rate), diuretic dosage profile (e.g., a function indicating how the dosage amount and/or dosage rate of diuretic should vary over time), time limits associated with diuretic delivery (e.g., maximum and/or minimum time period for diuretic delivery), other fluids received by the patient during the procedure (e.g., volume of ingested fluid, volume of fluid from other medical agents besides the diuretic and/or hydration fluid), and/or suitable combinations thereof. Other patient-related inputs may also be received at the display 150 and can include, for example, the patient's sex, weight (e.g., "dry" weight), age, ethnicity, clinical state (e.g., renal function parameters, electrolyte levels such as serum chloride levels), medical history (e.g., outcomes of previous fluid removal procedures, prior response to fluid therapy, and/or combinations thereof), diagnoses (e.g., ADHF, CHF), medications (e.g., whether the patient is diuretic-naïve or diuretic-resistant), dietary factors (e.g., whether the patient is consuming a high-salt or low-salt diet, amount of oral fluid intake), and/or combinations thereof.

Alternatively, or in combination, the user input via the display 150 can prompt the controller 140 to retrieve treatment parameters (e.g., maximum diuretic dosage, maximum continuous diuretic dosage, and minimum desired urine rate) from tables and/or other data sources. The data sources can be stored in the system 100 (e.g., in a memory associated with the controller 140) and/or can be stored in a separate device (e.g., a remote computing device). In some embodiments, the controller 140 retrieves data from a remote database and/or server via a communication network (e.g., a wired network, a wireless network, a cloud-based network, the Internet, and/or suitable combinations thereof). In such embodiments, the controller 140 can be operably coupled to a communication device and/or interface configured to transmit and receive data via the communication network.

The controller 140 can output the treatment parameters to the user via the display 150 for review and/or feedback. For example, the display 150 can show recommended treatment parameters for the patient P, such as recommendations for the diuretic, diuretic dosage rate (e.g., initial, maximum, and/or minimum dosage rate), hydration fluid infusion rate (e.g., initial, maximum, and/or minimum infusion rate), urine output rate (e.g., measured urine output rate, adjusted urine output rate, maximum and/or minimum output rate, and/or combinations thereof), treatment duration (e.g., maximum time period for diuretic and/or hydration fluid infusion; maximum total treatment duration), treatment escalation (e.g., thiazide, temporarily increased fluid matching, additional loop diuretic), end of treatment, and so on. As another example, the display 150 can output one or more predetermined treatment programs so the user can select the appropriate program for the particular patient P. Optionally, the user can modify any of the displayed treatment parameters, if desired.

During the treatment procedure, the controller 140 can output information regarding procedure status to the user via the display 150. For example, the controller 140 can display information regarding any of the following: urine output (e.g., current urine output rate and/or amount, urine output rate and/or amount over time, total amount of urine output so far), hydration fluid infusion (e.g., current infusion rate and/or amount, infusion rate and/or amount over time, total amount of hydration fluid infused so far), diuretic delivery (e.g., current dosage rate and/or amount, dosage rate and/or amount over time, total amount of diuretic delivered so far), fluid balance (e.g., current fluid balance, fluid balance over time, net fluid removal so far), system status (e.g., amount of hydration fluid remaining in the fluid source 122, amount of diuretic remaining in the diuretic source 134, remaining storage capacity in the container 112), treatment time (e.g., treatment start time, projected and/or planned treatment end time, total treatment duration so far), notifications (e.g., alerts, alarms, messages, recommendations, predictions, error messages), and the like. The user can review the displayed information, and, if appropriate, provide input instructing the controller 140 to adjust, pause, and/or stop the treatment procedure.

In some embodiments, the system 100 includes redundancy in the urine system 110, hydration system 120, and/or diuretic system 130 to reduce or minimize treatment interruptions, e.g., due to running out of urine collection capacity, running out of hydration fluid, and/or running out of diuretic. For example, the system 100 can include redundant components (e.g., containers 112, fluid sources 122, and/or diuretic sources 134), which can be stored at predetermined locations (e.g., on or within the console 105 or another portion of the system 100). The controller 140 can be configured to detect the presence of the redundant components, and can automatically or semi-automatically switch between these components so the treatment procedure can continue uninterrupted or substantially uninterrupted. Alternatively, or in combination, the system 100 can adjust the timing of user alerts related to urine collection capacity, hydration fluid levels, and/or diuretic levels, based on the availability of redundant components. For example, if redundant components are available, the system 100 can generate alerts at a later time (e.g., closer in time to when the container 112 would be full, when the fluid source 122 would be empty, and/or when the diuretic source 134 would be empty), since the system 100 can automatically switch to using the redundant components, or the user can rapidly perform the switch using the redundant components that are already stored locally at the system 100, rather than having to retrieve replacements from another location.

The lack of interruption in fluid therapy can help ensure effectiveness of the fluid therapy, e.g., by relieving the patient's fluid overload condition as quickly and safely as possible. In some embodiments, even brief interruptions in diuretic delivery and/or hydration fluid infusion can significantly affect the patient's urine output (e.g., cause the urine output rate to drop), which can interfere with therapeutic efficacy and prolong treatment time. The concerns described above regarding diuretic and/or hydration fluid backup supply may be unique to the present technology, e.g., due to the relatively large amounts of diuretic and/or hydration fluid that are utilized over time in some embodiments of the treatment procedures described herein. That is, whereas conventional systems and methods may utilize just a single diuretic source and/or a single hydration fluid source because of the relatively low amount of diuretic and/or hydration fluid administered, the present technology may benefit from multiple diuretic sources and/or hydration fluid sources to ensure treatment continuity. Similarly, the treatment procedures of the present technology can cause the patient P to produce relatively large volumes and/or rates of urine output compared to conventional procedures, such that multiple containers 112 may be helpful to reduce the number of times the user has to empty and/or replace the containers 112 during the procedure.

For example, in some embodiments, the urine system 110 includes two or more redundant containers 112 to ensure fluid therapy does not need to be stopped or interrupted due to the container 112 being full. In such embodiments, the urine system 110 can include a flow control assembly 116 (e.g., valves and/or other flow control components) operably coupled to the controller 140, and configured to selectively direct the urine from the patient P to one or more of the containers 112. The flow control assembly 116 can initially direct the urine received from the patient P to a first container 112. Once the flow control assembly 116 detects or determines the first container is full or nearly full (e.g., based on sensor data from the sensor(s) 114), the flow control assembly 116 can redirect the urine received from the patient P to a second container 112. While urine is being directed to the second container 112, a user can empty the first container 112 or replace the first container 112 with an empty container 112. The flow control assembly 116 and/or controller 140 can generate an alert to the user to indicate the first container is full and needs to be replaced or emptied. This process can be repeated such that fluid management therapy is not inadvertently interrupted due to the containers 112 being full and/or the urine system 110 being unable to accept urine output. In some embodiments, the treatment procedures described herein result in relatively large amounts and/or rates of urine output (e.g., compared to conventional therapies), such that automatic switching between multiple urine containers is advantageous to minimize treatment interruptions.

As another example, the hydration system 120 can include multiple redundant hydration fluid sources 122, e.g., to ensure the hydration fluid infusion can continue without interruption for the entirety of a therapy session and/or to provide an additional time window for switching hydration fluid sources 122 without interrupting hydration fluid infusion. In such embodiments, the hydration system 120 can include a hydration control assembly (e.g., valves and/or other flow control components—not shown) operably coupled to the controller 140, and configured to switch the source of hydration fluid from a first fluid source 122 to a second fluid source 122. In such embodiments, the hydration control assembly can initially deliver hydration fluid from the first fluid source 122 to the patient P. The hydration control assembly can monitor whether the first fluid source 122 is empty or nearly empty, e.g., based on data from the fluid sensor 128 and/or other sensors associated with the hydration system 120. Once the hydration control assembly detects or determines the first fluid source 122 is empty or nearly empty (e.g., the remaining amount of hydration fluid is below a predetermined threshold), the hydration control assembly can switch to delivering hydration fluid from the second source 122. The switching process can be repeated such that fluid therapy is not inadvertently interrupted due to the fluid source 122 being empty and/or the hydration system 120 being unable to provide hydration fluid.

The process of switching the hydration fluid source 122 can be performed automatically, semi-automatically, or manually. In some embodiments, semi-automatic or manual switching between the first and second fluid sources 122 may be beneficial to ensure the hydration system 120 does not automatically infuse hydration fluid without user confirmation. In such embodiments, the hydration control assembly and/or controller 140 can output an alert asking the user to verify that the hydration fluid should be switched from the first fluid source 122 to the second fluid source 122. Upon switching to the second fluid source 122, the controller 140 can generate an alert to the user to indicate the first fluid source 122 is empty and needs to be replaced. Optionally, the hydration control assembly and/or controller 140 can implement a pre-approval procedure in which the user allows the hydration system 120 to automatically infuse a specified volume of additional hydration fluid. Once that volume has been delivered to the patient P, the user may need to provide re-approval before further automatic infusion of hydration fluid.

In some embodiments, the different fluid sources 122 of the hydration system 120 each provide the same type of hydration fluid. In other embodiments, however, some or all of the fluid sources 122 can provide different types of hydration fluid. The hydration fluids can differ from each other with respect to tonicity, composition, electrolyte content, one or more other properties, and/or combinations thereof. Depending on the patient's response to diuresis, the hydration system 120 can deliver multiple different hydration fluids to the patient P sequentially or concurrently. For example, if the patient's urine output (including, e.g., the patient's adjusted urine output rate) indicates that the patient P has an electrolyte imbalance (e.g., a positive sodium balance), the hydration system 120 can switch to delivering a hydration fluid that would address the imbalance (e.g., a hydration fluid with lower sodium content). The switching can be performed using any of the techniques and/or devices described above. Accordingly, the particular fluid or fluids delivered to the patient P can be tailored to the patient's particular clinical state and/or response to treatment.

In yet another example, the diuretic system 130 can include multiple redundant diuretic sources 134, e.g., to ensure the diuretic delivery can continue without interruption for the entirety of a therapy session and/or to provide an additional time window for switching diuretic sources 134 without interrupting diuretic delivery. For example, if a first diuretic source 134 (e.g., a first syringe or container) is spent, the diuretic can continue to be supplied (e.g., without substantial interruption) via a second diuretic source 134 (e.g., a second syringe or container). The second diuretic source 134 can be connected to the console 105, and can be operably coupled to a sensor configured to detect the presence of the second diuretic source 134 (e.g., a location sensor, optical sensor, weight sensor, one or more other sensors, and/or combinations thereof). Accordingly, the diuretic system 130 can switch to the second diuretic source 134 if the first diuretic source 134 is empty or nearly empty, and the second diuretic source 134 is present.

In some embodiments, the diuretic system 130 includes two independent diuretic pumps each including its own diuretic source 134. For example, the diuretic system 130 can include syringe pumps each fluidly coupled to its own syringe filled with diuretic. In some cases, such syringes may only be filled by pharmacists or other health care professionals, and thus may not be readily replaced (e.g., in less than a few hours) by the user. When the diuretic system 130 and/or controller 140 detects that the first diuretic source 134 is empty or nearly empty (e.g., below a predetermined threshold), the diuretic supply can be switched (e.g., automatically or manually) to a second diuretic source 134. The switching process can include stopping a first syringe pump fluidly coupled to the first syringe, and starting a second syringe pump fluidly coupled to the second syringe. In other embodiments, the diuretic system 130 includes a single diuretic pump (e.g., syringe pump) connected to two diuretic sources 134. In such embodiments, case switching between the first and second diuretic sources 134 can involve using a diuretic control assembly (e.g., valves and/or other flow control components) to switch the diuretic pump from delivering diuretic from the first diuretic source 134 to the second diuretic source 134. The switching process can be repeated such that fluid therapy is not inadvertently interrupted due to the diuretic source 134 being empty and/or the diuretic system 130 being unable to provide diuretic.

The process of switching the diuretic source 134 can be performed automatically, semi-automatically, or manually. In some embodiments, manual or semi-automatic switching between the first and second diuretic sources 134 may be beneficial to ensure the diuretic system 130 does not automatically infuse a large volume of diuretic without user confirmation. In such embodiments, the controller 140 can output an alert asking the user to verify that the diuretic should be switched from the first diuretic source 134 to the second diuretic source 134. Upon switching to the second diuretic source 134, the controller 140 can generate an alert to the user to indicate the first diuretic source 134 is empty and needs to be replaced. Optionally, the controller 140 can predict a time point and/or time range when the first diuretic source 134 will be empty (e.g., based on the diuretic dosage rate), and can output a notification so the user can order or otherwise prepare a replacement diuretic source 134 before the first diuretic source 134 runs out. Moreover, the diuretic control assembly and/or controller 140 can implement a pre-approval procedure in which the user allows the diuretic system 130 to automatically delivery a specified additional dosage of diuretic. Once that dosage has been delivered to the patient P, the user may need to provide re-approval before further automatic delivery of diuretic.

In some embodiments, the different diuretic sources 134 of the diuretic system 130 each provide the same type of diuretic. In other embodiments, however, some or all of the diuretic sources 134 can provide different types of diuretics. Depending on the patient's response to diuresis, the diuretic system 130 can deliver multiple different diuretics to the patient P sequentially or concurrently. For example, the diuretic system 130 can initially deliver a first diuretic to the patient P from a first diuretic source 134. If the patient P responds poorly to the first diuretic (e.g., the urine output rate does not increase or increases very slowly), the diuretic system 130 can switch to delivering a second, different diuretic from a second diuretic source 134. The diuretic system 130 can continue delivering the first diuretic concurrently with the second diuretic, or can terminate delivery of the first diuretic when the second diuretic is delivered. The switching can be performed using any of the techniques and/or devices described above. As another example, if the patient P does not respond well to a single diuretic, the diuretic system 130 can simultaneously administer multiple diuretics to the patient P. The ratio of the different diuretics can be varied as appropriate to elicit a suitable urine output rate. In other embodiments, however, rather than automatically administering additional diuretics, the diuretic system 130 can output a notification recommending that the user manually administer a different diuretic to the patient P and/or requesting that the user approve administration of a different diuretic, which may be beneficial for patient safety. Without being bound by theory, some diuretics are absorbed at a proximal end of the kidney and other diuretics are absorbed at a distal end of the kidney, and using combinations of diuretics that are absorbed at the proximal and distal ends can be effective for improving overall fluid therapy.

The system 100 illustrated in FIG. 1 can be configured in many different ways. For example, the locations of the various components of the system 100 can be altered, e.g., the urine system 110, hydration system 120, and/or diuretic system 130 can be at different locations in the console 105.

As another example, any one of the urine system 110, hydration system 120, or diuretic system 130 can be part of a separate system or device (e.g., a separate console), or can be omitted altogether. For instance, in some embodiments, the urine system 110 is replaced with a mechanism for monitoring the patient's urine output that does not require the catheter 118 and/or urine collection, such as an ultrasound sensor that measures the patient's bladder volume. The ultrasound sensor can be implemented as a patch or similar device that is coupled to the patient's body. The controller 140 can process the ultrasound sensor data to detect changes in the bladder volume, and can determine the corresponding amount and/or rate of urine output based on the bladder volume. The use of non-invasive urine monitoring mechanisms such as an ultrasound sensor can allow the treatment procedures described herein to be performed in outpatient settings.

As another example, in some embodiments, the hydration system 120 is omitted such that diuresis is performed without hydration fluid infusion, or the hydration fluid is infused manually. Diuresis with hydration fluid infusion may be more beneficial for patients with low serum chloride levels (e.g., patients with low-salt diets), while patient with high serum chloride levels (e.g., patients with high-salt diets) may tolerate diuresis with little or no hydration fluid infusion. Optionally, the hydration fluid infusion rate can be varied at least partially based on the patient's serum chloride levels, e.g., lower amounts and/or rates of hydration fluid infusion can be used if the patient's serum chloride level is high (e.g., greater than or equal to 105 mmol/L).

In yet another example, the diuretic system 130 can be omitted such that no diuresis is performed, or the diuresis is performed manually. In such embodiments, the system 100 can provide automated fluid replacement via the hydration system 120 and/or can automatically monitor the patient's urine output via the urine system 110, but the diuretic would be administered manually by a healthcare professional in accordance with techniques known to those of skill in the art.

The system 100 can optionally include or be used in combination with additional systems or devices, such as systems or devices configured to perform any the following functions: administering other medications and/or agents besides the diuretic and hydration fluid (e.g., heart failure medication), monitoring other patient parameters besides urine output (e.g., blood pressure, weight, heart rate, blood oxygenation, respiratory rate, temperature), and/or performing other types of medical procedures on the patient P concurrently or sequentially with the fluid removal procedure (e.g., dialysis, ultrafiltration).

FIG. 2 is a flow diagram of a method 200 for treating a patient, in accordance with embodiments of the present technology. In some embodiments, the method 200 is used to treat the patient for fluid overload by removing fluid from the patient to produce a negative fluid balance (net fluid loss). The method 200 can be performed by any embodiment of the systems and devices described herein, such as the system 100 of FIG. 1. In some embodiments, some or all of the blocks of the method 200 are performed by a system or device including one or more processors and a memory storing instructions that, when executed by the one or more processors, cause the system or device to perform one or more of the blocks described herein. For example, the method 200 can be performed by the controller 140 of the system 100 of FIG. 1 and/or another suitable processor.

Optionally, some or all of the blocks of the method 200 can performed automatically or semi-automatically, with little or no human intervention.

The method 200 can begin at block 202 with obtaining a urine output rate from a patient. The urine output rate can be obtained from a urine monitoring and/or collection system connected to the patient, such as the urine system 110 of FIG. 1. The system can determine the urine output rate based on received input data, such as data from one or more sensors (e.g., the sensor(s) 114 of FIG. 1). As described above, the sensor(s) can be configured to measure the urine output rate based on flow rate, weight (e.g., of the container 112 of FIG. 1), volume, fluid level, and/or any other suitable parameter. The urine output rate can be calculated based on the received input, e.g., by a controller (e.g., controller 140 of FIG. 1) operatively coupled to the sensor(s). The urine output rate can be a current rate or an average rate measured over a predetermined time period (e.g., the previous 5 or 10 minutes). The urine output rate can be updated on a continuous or recurring basis (e.g., every 30 seconds, 1 minutes, 2 minutes, etc.). In some embodiments, the process of block 202 is performed concurrently with some or all of the other blocks of the method 200 (e.g., blocks 204, 206, and/or 208) to provide continuous or substantially continuous urine output monitoring through the entirety of the method 200. As described in greater detail below with reference to at least FIGS. 5A and 5B, in some embodiments the method 200 includes obtaining an adjusted urine output rate, e.g., based at least in part on the obtained urine output rate and a sodium excretion level of the patient.

At block 204, the method 200 optionally continues with causing a diuretic to be provided to the patient at a dosage rate. The diuretic can be or include furosemide, bumetanide, ethacrynic acid, torsemide, combinations thereof, and/or other diuretics known in the art. In some embodiment, the diuretic is delivered as part of a solution including saline or other hydration fluid(s) mixed therewith. The diuretic can be provided automatically or semi-automatically by a diuretic system connected to the patient, such as the diuretic system 130 of FIG. 1. The diuretic system can be operably coupled to a controller (e.g., controller 140 of FIG. 1) for causing diuretic delivery in accordance with a planned and/or preprogrammed treatment procedure.

In some embodiments, the treatment procedure includes multiple phases, and each phase is associated with a different delivery profile for the diuretic. In such embodiments, block 204 can be performed as part of an initial phase to determine an appropriate diuretic dosage rate for treating the patient (also known as a "dosage determining phase"). In the dosage determining phase, the diuretic is injected at an initial dosage rate, and the dosage rate can then be gradually increased (e.g., "ramped") to elicit an increase in the patient's urine output rate. The diuretic dosage rate can be increased according to a desired function or delivery profile, such as a continuous function, a block-wise function, or a combination thereof). The function can include iteratively increasing the dosage rate linearly, exponentially, according to a polynomial function, and/or any other suitable ramp function or profile. In some embodiments, the diuretic is delivered in a manner such that a subsequent dosage rate is a predetermined percentage (e.g., at least 5%, 10%, 15%, 25%, etc.) above the immediately previous dosage rate. The predetermined percentage can increase or decrease over time, e.g., depending on the desired fluid therapy and/or patient considerations. Optionally, the diuretic can be provided in a manner that doubles the diuretic dosage rate or total diuretic within a period of time (e.g., 10 minutes, 15 minutes, 20 minutes, or within a range of 10-20 minutes). In other embodiments, however, the dosage determining phase can include one or more time periods during which the diuretic dosage rate does not increase and/or is held substantially constant. The dosage determining phase can continue until the patient's urine output reaches or exceeds a desired threshold rate and/or a predetermined time period has elapsed, at which point the diuretic dosage rate can be adjusted, as described in block 208 below.

At block 206, the method 200 can optionally include causing a hydration fluid to be provided to the patient at a hydration rate. The hydration fluid can comprise saline and/or other fluids having sodium, and can be provided automatically or semi-automatically by a hydration fluid system connected to the patient, such as the hydration system 120 of FIG. 1. The hydration fluid can be provided before, during, and/or after providing the diuretic in block 204 (e.g., before, during, and/or after the dosage determining phase). Intravenous infusion of hydration fluid containing electrolytes (e.g., sodium and/or chloride) can increase diuretic efficiency, which is counterintuitive since a goal of fluid therapy is net removal of fluid. Hydration fluid can also reduce or inhibit intravascular depletion, decreases in cardiac output, and/or decreases in renal perfusion, among other benefits.

In some embodiments, the hydration fluid is provided to the patient based at least in part on the corresponding urine output rate, e.g., to drive net fluid loss from the patient. For example, the hydration rate can be less than the urine output rate. In some embodiments, the hydration rate is a percentage of the urine output rate (e.g., 90%, 80%, 70%, 60%, 50%, 40%, 30%, 20%, or 10% of the urine output rate) for a given range of urine output rates (e.g., from 0 mL/hr to 1000 mL/hr). Optionally, the percentage can be higher for certain parts of the range (e.g., for the lower end of the range to reduce the likelihood of hypotension) and/or lower for other parts of the range (e.g., for the higher end of the range to increase net fluid loss). As another example, the hydration rate can substantially match the urine output rate (e.g., 100% of the urine output rate) for an initial amount of urine output by the patient (e.g., at least the initial 150 mL, 200 mL, or 250 mL), for an initial time period (e.g., the first hour, 2 hours, or 3 hours), for an initial time period during hydration fluid and/or diuretic dose finding, and/or until the patient's urine output rate reaches a predetermined threshold. Subsequently, the hydration rate can be adjusted to be less than the urine output rate. In a further example, the hydration rate may be determined based on whether the urine output rate is above or below one or more different thresholds, with the difference between the urine output rate and hydration fluid rate increasing as the urine output rate increases. In such embodiments, the difference between the urine output rate and the hydration fluid rate can increase (with the urine rate being higher than the hydration fluid rate) as the urine output rate increases, and thus the net fluid loss from the patient can increase as the urine output rate increases.

At block 208, the method 200 can include adjusting at least one of the dosage rate of the diuretic or the hydration rate of the hydration fluid, thereby causing net fluid loss from the patient. For example, the (i) diuretic dosage rate can be adjusted, (ii) the hydration rate can be adjusted, or (iii) the diuretic dosage rate and the hydration rate can both be adjusted. In some embodiments, the diuretic dosage rate is adjusted after the dosage determining phase of the treatment procedure is complete. As discussed above in block 204, the dosage determining phase can end when (i) a predetermined amount of time has elapsed since the initial diuretic administration, and/or (ii) the urine output rate is or becomes greater than or equal to a predetermined threshold rate. The treatment procedure can then switch to a phase in which the diuretic dosage rate is adjusted to a dosage rate configured to maintain the patient's urine output rate at or above a desired output rate to cause net fluid loss (also known as a "continuous delivery phase" or "fluid reduction phase").

The adjusted diuretic dosage rate can be the initial dosage rate for the fluid reduction phase, and can be determined in many different ways. For example, the adjusted diuretic dosage rate can be based on the outcome of the dosage determining phase (e.g., the dosage rate when the patient's urine output reaches or exceeds the target threshold). In representative embodiments, the diuretic dosage rate is decreased, e.g., to maintain the patient's urine output rate at a predetermined rate and/or within a predetermined range (e.g., no more than 5%, 10%, or 20% variability from a predetermined rate). Decreasing the diuretic dosage rate can decrease the rate of increase in urine output rate (e.g., cause the patient's urine output to approach a constant or substantially constant rate) but without actually decreasing the urine output rate itself.

In some embodiments, the adjusted diuretic dosage rate is a predetermined percentage or fraction of the current dosage rate (e.g., the dosage rate at the end of the dosage determining phase) or a predetermined percentage of the cumulative diuretic dosage amount (e.g., the cumulative amount delivered during the dosage determining phase). For example, the adjusted dosage rate can be a predetermined percentage (e.g., 10%, 15%, 20%, 25%, 30%, or within a range of 10-30%) of a value of the total amount of diuretic delivered to the patient at that time. For example, if the total amount delivered is 100 mg, and the predetermined percentage is 25%, then the adjusted dosage rate can be 25 mg/hr. In some embodiments, the percentage used to calculate the adjusted diuretic dosage rate is based on a pharmacokinetic characteristic of the particular diuretic being infused. For example, the percentage can be 20% for furosemide, such that if 50 mg of furosemide is infused in 60 minutes, then the adjusted diuretic dosage rate can be 10 mg/hr.

In some embodiments, block 208 includes delivering the diuretic at the adjusted diuretic dosage rate until the fluid reduction phase is complete, e.g., until a predetermined period of time has elapsed, the patient's urine output drops below a low urine output threshold, and/or until a target net fluid loss volume is achieved. During the fluid reduction phase, the diuretic dosage rate can be constant or substantially constant (e.g., no more than 5%, 10%, or 20% variability from the initially determined adjusted diuretic dosage rate). In other embodiments, however, block 208 can include making additional adjustments to the diuretic dosage rate during the treatment procedure (e.g., increasing and/or decreasing the diuretic dosage rate). The adjustments can be based on whether one or more of a predetermined set of conditions is met, such as whether the urine output rate is too high (e.g., which can indicate that the patient has a high and/or increasing serum level of diuretic). The set of conditions can include (i) an average urine rate being greater than a predetermined rate for a period of time, (ii) an average rate of change of the urine rate being greater than a predetermined rate of change, and/or (iii) a diuretic dosage rate being greater than a predetermined dosage rate. If some (e.g., two) or all of the conditions are met, the diuretic dosage rate can be decreased (e.g., by a predetermined amount or percentage), also referred to herein as "down-titration."

In some embodiments, a down-titration is performed only if all or a majority of the above conditions are met, which can avoid unnecessarily decreasing the diuretic dosage rate, thereby allowing urine output rates to remain high and avoiding unnecessary interruptions to the treatment procedure. For example, whereas other methodologies may interrupt fluid therapy and decrease the diuretic dosage rate (e.g., to zero mg/hr) only when the urine rate too high, the process described herein may only decrease the dosage rate (e.g., to a non-zero or zero dosage rate) when one or more factors are met, such as when the urine output rate is both high and continuing to increase. Stated differently, the process herein can prevent the diuretic dosage rate from being unnecessarily decreased when urine rates are temporarily high (e.g., above the predetermined rate), but are trending downward. This approach can prevent or inhibit over-diuresis, excess fluid loss and/or electrolyte loss, as well limit unnecessary exposure of the patient to additional diuretic. Additionally, because the diuretic dosage rate can be down-titrated, rather than stopping the diuretic entirely, the fluid therapy can continue (albeit at lower urine output rates) without needing to completely restart the procedure.

As another example, the additional adjustments to the diuretic dosage rate in block 208 can include increasing the diuretic dosage rate, also referred to herein as "re-ramping" or "up-titration." In some embodiments, re-ramping is performed if urine output rates are too low, as determined based on a set of conditions. The set of conditions can include (i) the average urine rate being below a predetermined threshold rate for a predetermined period of time, and/or (ii) more than a predetermined amount of debt has accumulated over the predetermined period of time. "Debt" can be defined as the area on a plot between the urine output rate and a set rate (e.g., 325 mL/hr), and can represent how much of and for how long the urine output rate has been below the set rate. If some or all of the conditions are met, re-ramping can be performed by incrementally increasing the diuretic dosage rate until (i) a predetermined amount of time has elapsed, and/or (ii) the urine output rate is or becomes greater than or equal to a predetermined threshold rate. The re-ramp process can be identical or generally similar to the dosage determining process previously described in block 204. In representative embodiments, the dosage rate or "ramp" can start at any dosage identified during the dosage determining process, such as the current dosage rate, a previously determined dosage rate, or another suitable dosage rate (e.g., not at the beginning of the dosage).

The re-ramping process can be performed automatically, semi-automatically, or manually. In some embodiments, re-ramping is a semi-automatic or manual process requiring user approval, e.g., for regulatory and/or safety reasons. In such embodiments, the system can output a notification to the user (e.g., via the display 150 of FIG. 1) instructing the user to confirm that re-ramping should be initiated. Optionally, the system can implement a pre-approval procedure in which the user can allow the system to automatically perform re-ramping under certain conditions (e.g., within a specific time period, until a certain urine output volume and/or rate is achieved, for a maximum diuretic amount and/or dosage rate, and/or combinations thereof). This approach can allow for automatic re-ramping under limited circumstances, which can reduce the amount of human intervention during the treatment procedure and improve the responsiveness of the system to the patient's current state. Once the pre-approval conditions have elapsed, the user may need to provide re-approval before additional automatic re-ramping is allowed.

In some embodiments, block 208 also includes adjusting the diuretic dosage rate in response to a potential and/or detected blockage (e.g., an air lock, a kink in a fluid line, other blockages, and/or combinations thereof) in the urine collection system. For example, an air lock can be any partial or complete obstruction of fluid flow due to trapped gas (e.g., air) within a fluid system. Air locks may produce an artificial drop in urine output rates, which can affect the determination of the diuretic dosage rate (e.g., result in a diuretic dosage rate that is too high). In some embodiments, the presence of an air lock is detected based on a period of little or no urine output (due to the air lock blocking urine flow), followed by a sudden large bolus of urine output (due to built-up pressure in the fluid line clearing the air lock). When the system detects that an air lock or other blockage was or is present, the system can compensate by adjusting the diuretic dosage rate to the dosage rate that should have been used if the air lock or other blockage had not occurred. The appropriate dosage rate can be determined based on historical data for the patient receiving the fluid therapy and/or one or more other patients (e.g., the diuretic dosage rate before the air lock occurred, a diuretic dosage rate calculated from the patient's urine output rate before the air lock occurred, and/or combinations thereof).

Alternatively, or in combination, block 208 can include adjusting the hydration rate, e.g., by increasing or decreasing the hydration rate based on the patient's urine output rate to drive net fluid loss from the patient. For example, as previously described, the hydration rate can initially match the patient's urine output rate for a set of initial conditions (e.g., certain time period, initial urine output amount, and/or initial urine output rate). Once the initial conditions have elapsed, the hydration rate can be maintained at a rate lower than the urine output rate (e.g., a percentage of the urine output rate) so the patient exhibits net fluid loss during the fluid reduction phase. The hydration rate can be determined in various ways, such as a percentage or fraction of the patient's urine output rate, based on whether the urine output rate is above or below a number of different thresholds (e.g., with the difference between the urine output rate and hydration rate increasing as the urine output rate increases), and/or any other suitable approach.

Optionally, the diuretic dosage rate and/or hydration rate can be adjusted based on factors other than patient's urine output rate. For example, as described in greater detail below with reference to at least FIGS. 5A and 5B, in some embodiments the diuretic dosage rate and/or hydration rate can be adjusted based at least in part on the patient's adjusted urine output rate. In these and/or other embodiments, the diuretic dosage rate and/or hydration rate can be adjusted based on the patient's urine conductivity, urine sodium concentration, urine chloride concentration, urine temperature, urine oxygen levels, and/or combinations thereof, in addition to or in lieu of the urine output rate and/or the adjusted urine output rate. In some embodiments, the diuretic dosage rate and/or hydration rate can be adjusted based on the patient's blood pressure in order to avoid placing the patient in a hypotensive state. In some embodiments, if the patient's blood pressure level is too low (e.g., below a threshold value or range), the system can avoid increasing the diuretic dosage rate and/or can decrease the diuretic dosage rate for a certain period of time. Alternatively, or in combination, the system can increase the hydration rate (e.g., to the maximum allowable hydration rate and/or to provide a desired fluid replacement profile (e.g., a 100% match to the patient's urine output rate)) for a certain period of time if low blood pressure levels are detected. The system can also output an alert indicating that the patient's blood pressure level is low so a user can check on the patient's status. Optionally, the system can take both blood pressure levels and urine output rates into account, e.g., the system can generate alerts and/or can adjust the diuretic dosage rate and/or hydration rate if the patient's blood pressure is low and the patient's urine output rate drops. This approach can improve patient safety and control over the treatment procedure.

In some embodiments, some or all of the blocks of the method 200 are performed as part of a medical procedure for treating the patient for a fluid overload condition. The method 200 can be used as a primary, standalone therapy for treating fluid overload, or can be used in combination with other therapies (e.g., as a post-primary therapy to reduce the likelihood of re-hospitalization). The method 200 can be performed in any suitable setting, such as an inpatient setting or an outpatient setting. In embodiments where the method 200 is performed as an outpatient therapy, the overall duration of the method 200 can be reduced (e.g., to no more than 10 hours, 5 hours, 4 hours, 3 hours, 2 hours, or 1 hour).

The method 200 illustrated in FIG. 2 can be modified in many different ways. For example, any of the blocks of the method 200 can be omitted, such as blocks 204 or 206. In some embodiments, block 204 is omitted so that the method 200 controls hydration fluid infusion but not diuretic delivery, or so that the method 200 does not involve any diuretic delivery at all. Similarly, block 206 can be omitted so that the method 200 controls diuretic delivery but not hydration fluid infusion, or so that the method 200 does not involve any hydration fluid infusion at all. As another example, some or all of the blocks 200 of the method 200 can be performed in a different order and/or repeated (e.g., any of blocks 202, 204, 206, and/or 208). In a further example, the method 200 can optionally include additional blocks not shown in FIG. 2 (e.g., causing delivery of additional medications, obtaining parameters other than urine output rate, and/or combinations thereof).

The present technology can provide many advantages for treating fluid overload and/or managing patient fluid levels. For example, embodiments of the present technology have been shown to consistently reduce the fluid volume in patients faster and safer than conventional treatment systems and methods. For example, whereas conventional methods can typically take at least five days to remove 4-5 L of net fluid volume, embodiments of the present technology have been shown to remove 4-5 L liters of net fluid volume in no more than 24 hours. Additionally, embodiments of the present technology have also been shown to remove significant amounts of salt via high sodium urine from patients. This can reduce the likelihood of the patient reaccumulating fluid after discharge, which can lead to reductions in rehospitalization rates. Moreover, embodiments of the present technology can automatically and continuously monitor urine output, hydration fluid infusion, urine sodium concentration, and/or diuretic delivery to mitigate patient safety concerns (e.g., over-diuresis and/or hypotension) during the treatment procedure.

Embodiments of the present technology can provide various benefits, such as any of the following: (i) optimizing net fluid volume removal; (ii) reducing the time needed to achieve desired net fluid removal by allowing physicians to use higher diuretic dosages and/or dosage rates earlier in treatment compared to conventional treatments; (iii) avoiding or reducing risk of adverse events such as over-diuresis, dehydration, and/or intravascular depletion; (iv) quickly assessing if a patient is diuretic resistant; and (v) providing a record of treatment data. Embodiments of the present technology may obtain an average net fluid removal rate (e.g., average urine output rate minus average hydration fluid infusion rate) of at least 225 mL/hr, which provides 3.4 L per day of net fluid volume removal based on introducing 2 L of fluid per day orally or through IV infusion. This rate of fluid removal, while replacing sodium, may reduce the overall length of stay and/or provide enhanced decongestion.

Various aspects of one or more embodiments of the present technology can be based at least partially on one or more models ("model(s)"), such as artificial intelligence (AI) and/or machine learning (ML) models. Individual ones of these models can be trained using historical treatment data from one or more other patients and configured to determine and/or predict information about the patient receiving treatment, and/or otherwise inform the system's and/or the user's decisions regarding the patient's therapy. For example, in some embodiments the model(s) are configured to determine and/or predict information associated with diuretic delivery during fluid therapy. Individual ones of the model(s) can be configured to (i) predict the diuretic dose to elicit the desired urine output response from the patient, (ii) predict the occurrence of therapy re-ramps and/or automatically re-ramp the patient's therapy, and/or (iii) identify and/or select the diuretic(s) most likely to elicit the desired fluid removal response. Additionally, or alternatively, the model(s) are configured to determine and/or predict information associated with hydration fluid delivery during fluid therapy. For example, the model(s) can be configured to (i) predict the risk of the patient tolerating/not tolerating a given hydration fluid delivery rate, (ii) predict the likelihood of the patient's urine output exceeding a threshold value (e.g., falling below a threshold value), and/or (iii) adjust the patient hydration fluid delivery rate to improve the patient's urine output. In these and other embodiments, the model(s) are configured to determine and/or predict information associated with altering the patient's fluid therapy, including one or more steps, blocks, and/or protocols associated therewith. For example, the model(s) can be configured to (i) determine information associated with a decision to stop the patient's fluid therapy to guide a user's decision regarding the same, (ii) predict a readmission risk for the patient once the patient's fluid therapy has ended, (iii) recommend and/or determine oral diuretic dosage information associated with the patient, and/or (iv) identify patients not expected to respond to fluid therapy. In further embodiments, one or more of the model(s) are configured to determine, before beginning and/or during fluid therapy, a likelihood of the patient experiencing one or more adverse events during the fluid therapy. In some embodiments, the model(s) are configured to determine a time until a hydration fluid source and/or a diuretic source is expected to be empty and/or a time until a urine collection container is expected to be full.

Generally, the model(s) are expected to improve the effectiveness of the fluid therapy steps/blocks/protocols described herein. In some embodiments, the model(s) are expected to improve a specific patient's response to the fluid therapy steps/blocks/protocols described herein. In further embodiments, the model(s) are expected to optimize (e.g., maximize) a patient's response to the fluid therapy steps/blocks/protocols described herein in real-time, for example, based on data received from the patient associated with the patient's response to the fluid therapy.

As described in greater detail below with reference to FIGS. 5A and 5B, in some embodiments the method 200 further includes obtaining an adjusted urine output rate, e.g., based at least in part on the obtained urine output rate and a sodium excretion level of the patient. The method 200 can use the adjusted urine output rate in an at least generally similar or identical manner as the obtained urine output rate (block 202), and is expected to provide all, or at least a portion, of the advantages described herein. Moreover, as described below, embodiments of the present technology that use the adjusted urine output rate are expected to improve or optimize net fluid loss, e.g., compared to embodiments that use the obtained urine output rate.

III. FLUID THERAPY BASED ON AN ADJUSTED URINE OUTPUT RATE

The algorithm used in at least some fluid therapy systems is designed based on the expectation that, in the setting of a loop diuretic induced diuresis, urine sodium concentration is directly proportional to urine flow. Thus, with high urine flow rates observed during therapy, a patient's urine sodium concentration is expected to be high (e.g., an average patient urine sodium excretion of about 140 mmol/L). If the average patient urine sodium concentration stays close to this expected value, urine flow rate can be used as a proxy for urine sodium concentration, and the amount and/or rate of saline and diuretic infusion can rely on this assumption with a goal of producing a net negative sodium balance. At least some patients, however, have sodium excretion levels lower than the expected concentration. For example, a patient may instead have an average urine sodium concentration during the first 24 hours of therapy of only 108 mmol/L, lower than the expected 140 mmol/L. The outcome of fluid therapy for these patients, including net sodium removal, performed based on the (incorrect) assumption that the patient's urine sodium concentration is 140 mmol/L, can vary quite considerably due to this difference.

Figure 3:
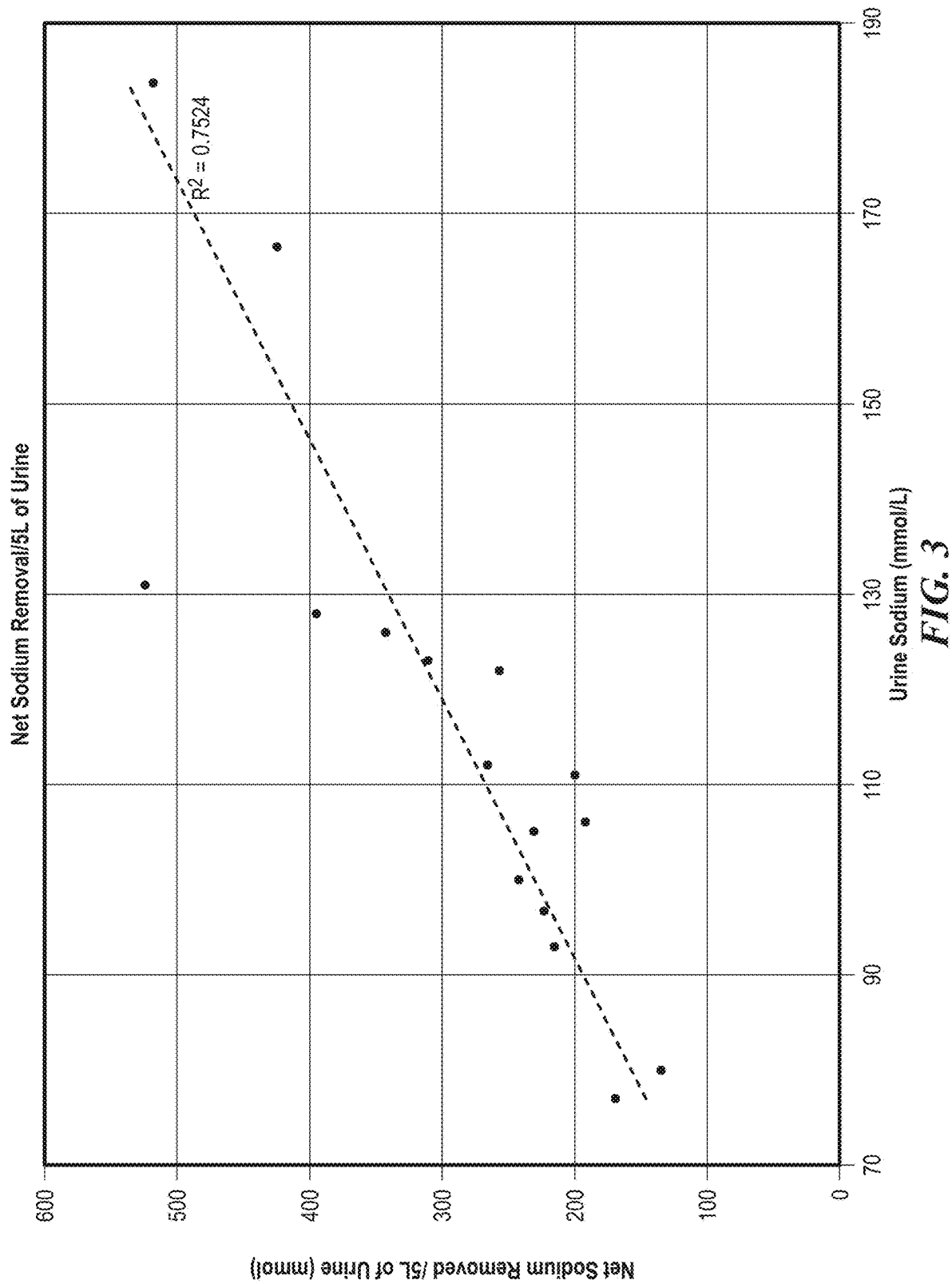
FIG. 3 is a graph of patient clinical data showing net sodium removed per five liters of urine collected versus the patient's urine sodium concentration in the first 24 hours of urine collection.
Figure 4:
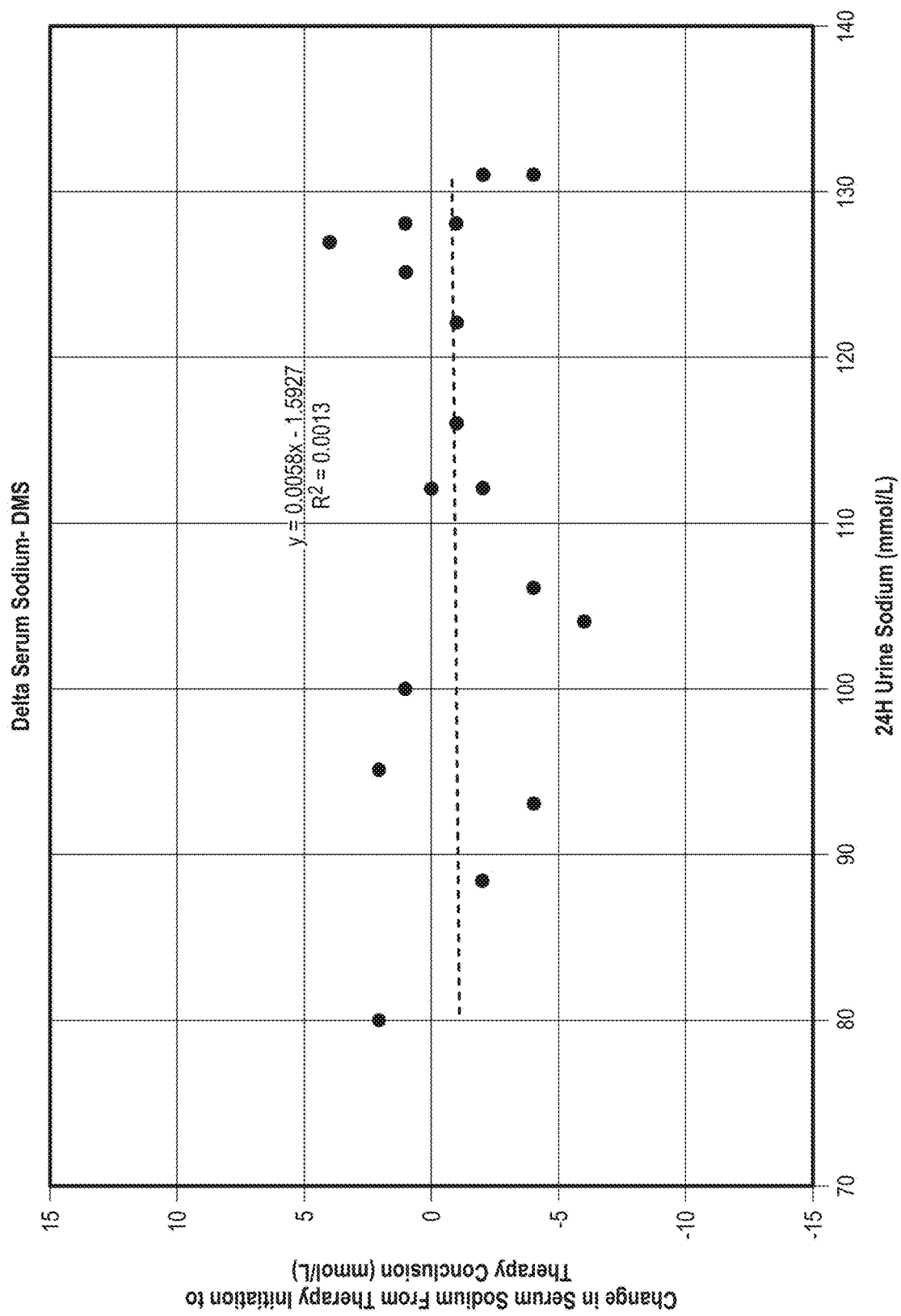
FIG. 4 is a graph of patient clinical data showing a change in patient serum sodium during therapy versus patient urine sodium concentration in the first 24 hours of urine collection.

FIG. 3, for example, is a chart of clinical patient data showing the net sodium removed per five liters of urine collected versus the patient's urine sodium concentration in the first 24 hours of urine collection. Each data point corresponds to a unique patient undergoing standard diuretic therapy. As shown in FIG. 3, the net sodium removed differs for different urine sodium concentrations, with patients having lower urine sodium concentrations losing less sodium per liter of urine output than patients with higher urine sodium concentrations. FIG. 4 is another chart of clinical patient data showing the change in serum sodium versus the patient's average urine sodium concentration in the first 24 hours of urine collection, and illustrates that the serum sodium concentrations for these patients (i.e., the same patients represented in FIG. 3) was stable (e.g., did not change by a clinically significant amount) for this period. Accordingly, the difference in the urine sodium concentration between patients shown in FIG. 3 can be attributed, at least in part, to varying fluid intake by these patients (e.g., with some patients likely exceeding the fluid intake restriction specified in the treatment protocol). Patients that consume excess fluid can increase their urine volume and in doing so reduce (e.g., dilute) the concentration of sodium in their urine. This excess fluid intake can also lead to an increased urine output rate that can inhibit, or even prevent, fluid therapy from reaching the diuretic infusion rates required to reach a desired (e.g., optimal) level of sodium excretion. That is, when the actual urine sodium concentration for these patients is not taken into account (e.g., measured or otherwise obtained) during fluid therapy, and instead these patients are treated based on a measured urine output rate, then patients with different urine sodium concentrations who have the same urine output rate will receive the same amount of infused saline (and thus sodium). This results in patients with lower-than-expected urine sodium receiving excess amounts of hydration fluid (including, e.g., sodium) and, in turn, exhibiting a lower net negative sodium balance than desired (e.g., because sodium lost in urine is replaced by sodium infused as hydration fluid). The net negative sodium balance in these patients can be increased or optimized when their fluid therapy is based on an adjusted urine output rate that takes into account both the patients' measured urine output rates and their specific urine sodium concentrations.

FIG. 5A is a flow diagram of a method 500 for treating a patient based on an adjusted urine output rate, in accordance with embodiments of the present technology. In some embodiments, the method 500 is used to treat the patient for fluid overload by removing fluid from the patient to produce a negative fluid balance (e.g., a net fluid loss). The method 500 can be performed by the embodiments of the systems and devices described herein, such as the system 100 of FIG. 1. In some embodiments, some or all of the blocks of the method 500 are performed by a system or device including one or more processors and a memory storing instructions that, when executed by the one or more processors, cause the system or device to perform one or more of the blocks described herein. For example, the method 500 can be performed by the controller 140 of the system 100 of FIG. 1 and/or another suitable processor. Optionally, some or all of the blocks of the method 500 can performed automatically or semi-automatically, with little or no human intervention.

The method 500 can begin at block 502 with obtaining a sodium excretion input for a patient. The sodium excretion input can include a level, an amount, a concentration, or combinations thereof, of sodium in the urine excreted from the patient. In at least some embodiments, for example, the sodium excretion input includes a sodium output rate and/or a measured concentration of sodium in a predetermined quantity of urine (e.g., up to 1 L, 2 L, 3 L, 4 L, 5 L, etc.) obtained from the patient. In some embodiments, obtaining the sodium excretion input can include performing one or more tests to determine a sodium concentration or excretion level of urine in one or more of the containers 112 (FIG. 1), e.g., after individual ones of the containers 112 have been filled and/or removed from the system 100 (FIG. 1). For example, when the patient fills one of the containers 112, and/or whenever the user chooses to empty one of the containers 112, the user can obtain a sample of the urine within the container 112 prior to emptying the bag. This sample can be sent to a local hospital lab or other testing facility so that the urine sodium concentration (mmol/L) in the sample can be measured. When the user receives the result, or the result is otherwise determined and/or obtained, the user, a practitioner or other user can input the result (e.g., an amount of sodium excreted by the patient via urine or other sodium excretion input) into the system 100, e.g., via the display 150 and/or another suitable input device. In some embodiments, this result is provided to the system within a predetermined amount of time (e.g., up to 10 minutes, 20 minutes, 30 minutes, 1 hour, 2 hours, 3 hours, etc.) following sample collection. Additionally, or alternatively, the sodium excretion input can be obtained via one or more of the sensors 114 (FIG. 1), e.g., using any of the devices and/or techniques described herein, in U.S. Pub. No. 2022/0339622, filed Apr. 26, 2022, titled "MEASURING AND/OR DETECTING ANALYTES IN URINE, AND ASSOCI-ATED SYSTEMS, DEVICES, AND METHODS," and/or in U.S. application Ser. No. 18/434,540, filed Feb. 6, 2024, and titled "OBTAINING URINE CHARACTERISTICS TO PROVIDE FLUID THERAPY, AND ASSOCIATED SYSTEMS, DEVICES, AND METHODS," both of which are hereby incorporated by reference herein.

At block 504, the method 500 can include obtaining a urine output rate of the patient. Block 504 can be at least generally similar or identical to block 202 of the method 200, described with reference to FIG. 2.

At block 506, the method 500 can include determining an adjusted urine output rate for the patient based, at least in part, on the obtained sodium excretion input (block 502) and the urine output rate (block 504). The adjusted urine output rate can be based on the expected sodium excretion input (e.g., an ideal sodium excretion input). In some embodiments, for example, determining the adjusted urine output rate includes determining the adjusted urine output rate by dividing the sodium excretion input by the expected sodium excretion level and multiplying by the urine output rate, as shown in the following formula:

$$\text{Adjusted Urine Output Rate} = \left(\frac{\text{Sodium Excretion Input}}{\text{Expected Sodium Excretion Level}}\right) \text{Urine Output Rate} \quad \text{Eq. 1}$$

The expected sodium excretion input can be a predetermined urine sodium concentration for a single patient or for a group of patients. The single patient or group of patients can be an actual group, e.g., based on clinical data, or an estimated group, a modeled group, a simulated group, a historical group, a subset of a patient population, and/or combinations thereof. The single patient or group of patients can be selected based, at least in part, on a profile of the single patient or group of patients, including factors such as gender, height, weight, body mass index (BMI), history of diuretic resistance, and/or combinations thereof. In these and/or other embodiments, the expected sodium excretion input can be a concentration of between about 10 millimoles per liter (mmol/L) and about 200 mmol/L, such as no more than 20 mmol/L, 30 mmol/L, 40 mmol/L, 50 mmol/L, 60 mmol/L, 70 mmol/L, 80 mmol/L, 90 mmol/L, 100 mmol/L, 110 mmol/L, 120 mmol/L, 130 mmol/L, 140 mmol/L, 150 mmol/L, 160 mmol/L, 170 mmol/L, 180 mmol/L, 190 mmol/L, or another suitable concentration. At least some embodiments use 140 mmol/L as the expected sodium excretion input, a value that can be determined based on an average concentration of sodium in urine obtained from fluid therapy patients in a clinical study.

As described further below, adjusting the patient's measured urine output rate based on the patient's actual sodium output allows the system to adjust saline infusion and/or other aspects of fluid therapy based on the patient's rate of sodium output and not simply, e.g., the patient's urine output. Without this adjustment, a patient with excessive oral fluid intake and thus low urine sodium concentration might cause the system to replace sodium-poor urine output with sodium rich saline, blunting the net sodium removal of the system. By adjusting for urine sodium concentration, the system optimizes not only net fluid removal but also net sodium removal. In some embodiments, prior to obtaining the first sodium excretion input (block 502), the system uses a default urine sodium concentration of 140 mmol/L to calculate the sodium-adjusted urine output rate.

At block 508, the method 500 can include providing fluid therapy based, at least in part, on the adjusted urine output rate (block 506). In some embodiments, block 508 includes causing a diuretic to be provided to the patient at a dosage rate, e.g., as described previously herein with reference to block 204 of the method 200 (FIG. 2). Additionally, or alternatively, block 508 can include causing a hydration fluid to be provided to the patient at a hydration rate, e.g., as described previously herein with reference to block 206 of the method 200 (FIG. 2). In these and/or other embodiments, block 508 can include adjusting at least one of the dosage rate of the diuretic or the hydration rate of the hydration fluid, e.g., as described previously herein with reference to block 208 of the method 200 (FIG. 2). The adjustment to the dosage rate of the diuretic and/or the hydration rate of the hydration fluid can be adjustments to an initial dosage rate of the diuretic and/or an initial hydration rate of the hydration fluid administered to the patient, e.g., at the start of therapy and/or to induce fluid loss before the patient has produced sufficient urine to obtain a sodium excretion input (block 502). Each of the hydration rate, the diuretic dosage rate, the adjustment to the hydration rate, and the adjustment to the diuretic dosage rate can be determined as described previously herein with reference to the corresponding portions of the method 200, but with the determination based on the adjusted urine output rate (block 506) instead of the urine output rate (block 202). As described previously herein, basing fluid therapy on the adjusted urine output rate (block 506) is expected to account for, or at least partially account for, variations in the sodium excretion level of the patient and, in turn, increase or optimize the patient's urine output. The increased or optimized efficacy of fluid therapy (e.g., as measured by patient weight and/or fluid loss) is not expected to have a negative effect on (i.e., increase in) the patient's creatine levels.

In some embodiments, providing fluid therapy can include determining one or more therapy thresholds, e.g., associated with diuretic delivery, hydration fluid delivery, therapy escalation, therapy stopping, and/or combinations thereof. For example, providing fluid therapy can include determining (e.g., during a "dose finding" phase) a urine rate threshold, a low urine rate threshold, and/or a high urine rate threshold, each of which is described further below with reference to Table 2 and one of FIGS. 6-8. Additionally, or alternatively, providing fluid therapy can include determining a desired target sodium excretion rate for the patient, as described in further detail below with reference to FIG. 9.

Figure 5B:
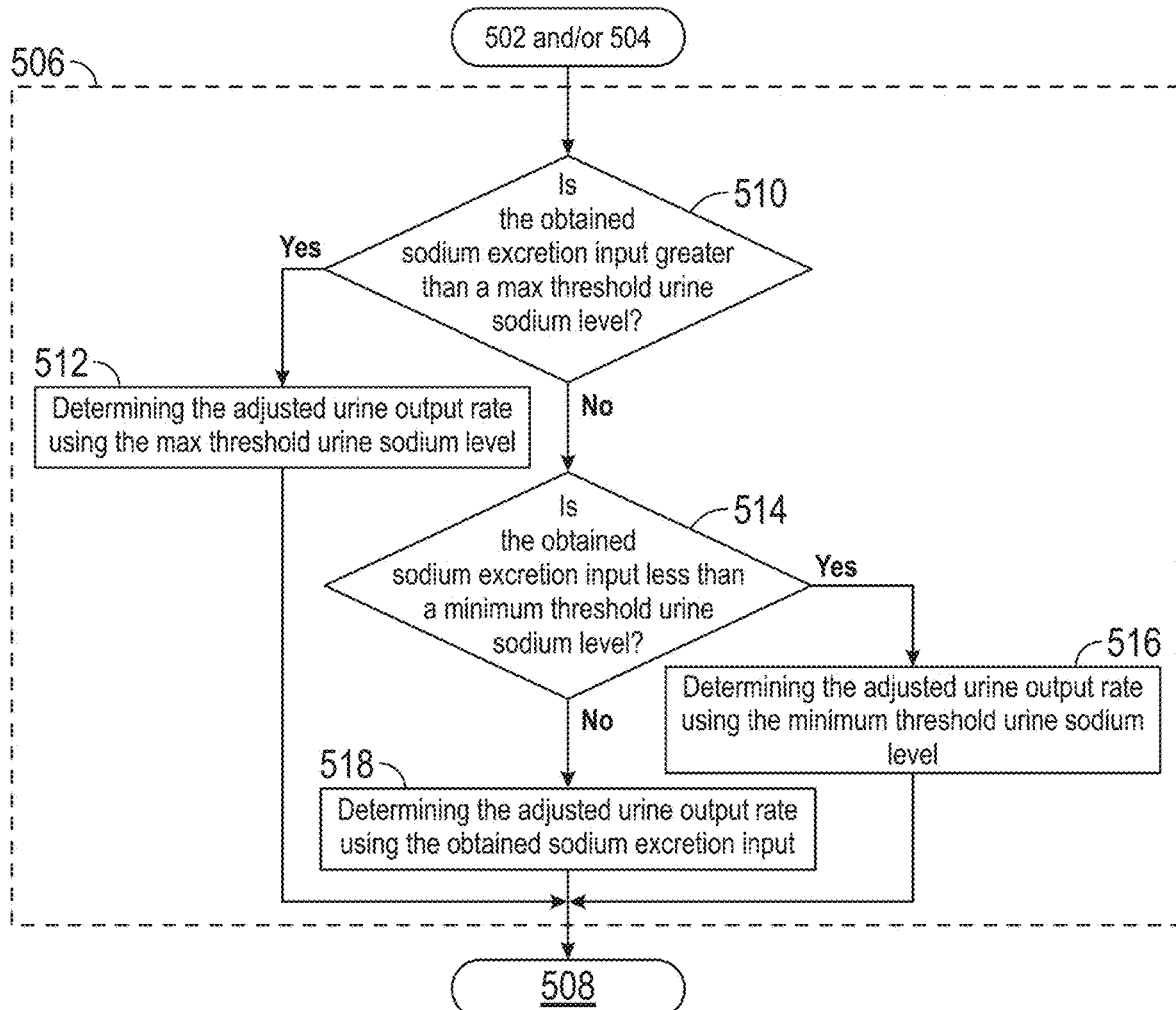
FIG. 5B is a flow diagram showing process portions for one block of the method of FIG. 5A, configured in accordance with embodiments of the present technology.

FIG. 5B is a flow diagram showing process portions for block 506 of the method 500 of FIG. 5A, in accordance with embodiments of the present technology. At process portion 510, the block 506 can include determining whether the obtained sodium excretion input (block 502, FIG. 5A) is greater than a max threshold urine sodium level. The max threshold urine sodium level can correspond to a concentration of sodium in urine associated with patients having hypertonic urine. In some embodiments, the max threshold urine sodium level is at least generally similar or identical to the expected urine sodium level, e.g., described above with reference to block 506 (FIG. 5A). For example, the max threshold urine sodium level can be a concentration of sodium in urine of about 140 mmol/L. If the obtained sodium excretion input is greater than the max threshold urine sodium level (process portion 510, YES), then, in process portion 512, block 506 can include determining the adjusted urine output rate using the max threshold urine sodium level, e.g., instead of the obtained sodium excretion input (block 502, FIG. 5A). If, however, the obtained sodium excretion input is less than the max threshold urine sodium level (process portion 510, NO), then block 506 can continue to process portion 514.

In process portion 514, block 506 can include determining whether the obtained sodium excretion input is less than a minimum threshold urine sodium level. The minimum threshold urine sodium level is less than the max threshold urine sodium level, and can correspond to a concentration of sodium in urine associated with patients having hypotonic urine. In at least some embodiments, for example, the minimum threshold urine sodium level can be a concentration of between about 10 mmol/L and about 200 mmol/L, such as no more than 20 mmol/L, 30 mmol/L, 40 mmol/L, 50 mmol/L mmol/L, 60 mmol/L, 70 mmol/L, 80 mmol/L, 90 mmol/L, 100 mmol/L, 110 mmol/L, 120 mmol/L, 130 mmol/L, 140 mmol/L, 150 mmol/L, 160 mmol/L, 170 mmol/L, 180 mmol/L, 190 mmol/L, or another suitable concentration. If the obtained sodium excretion input is less than the minimum threshold urine sodium level (process portion 514, YES), then, in process portion 516, block 506 can include determining the adjusted urine output rate using the minimum threshold urine sodium level, e.g., instead of the obtained sodium excretion input (block 502, FIG. 5A). If, however, the obtained sodium excretion input is not less than the minimum threshold urine sodium level (process portion 512, NO), then block 506 can continue to process portion 518 by determining the adjusted urine output rate using the obtained sodium excretion input (block 502, FIG. 5A).

A. Saline Infusion

One goal of the present technology is to maintain and/or maximize the rate of sodium removal from the patient independent of the patient's sodium excretion level (e.g., the sodium excretion input obtained for a given patient). As such, embodiments of the present technology can utilize a patient's specific sodium excretion level to reduce the amount of hydration fluid infused into patients. In doing so, the therapy provided to the patient can be based on the actual concentration of sodium in these patients' urine and, in turn, improve net fluid loss rates and/or treatment outcomes. To illustrate this, a theoretical model of the sodium excretion rates, based on an expected urine sodium concentration of 140 mmol/L, is shown below in Table 1 for two example patients. One patient (Patient 1) has an actual urine sodium concentration of 140 mmol/L (e.g., equal to the expected urine sodium concentration), while the other patient (Patient 2) has an actual urine sodium concentration of 108 mmol/L, lower than the expected urine sodium concentration. Both patients have a urine output of 525 milliliters per hour (mL/hr) but, because Patient 2 has a lower urine sodium concentration, they excrete a reduced amount of sodium in their urine (−56.7 mmol/hr) compared to Patient 1 (−73.5 mmol/hr). The table below illustrates how these patients respond to fluid therapy based on the obtained urine output rate versus fluid therapy based on the adjusted urine output rate:

TABLE 1

|  | Fluid Therapy based on Obtained Urine Output Rate | | Fluid Therapy based on Adjusted Urine Output Rate | |
| --- | --- | --- | --- | --- |
|  | Patient 1 | Patient 2 | Patient 1 | Patient 2 |
| Urine Output: | | | | |
| Measured Urine Output Rate (ml/hr) | 525 | 525 | 525 | 525 |
| Urine Sodium Concentration (mmol/L) | 140 | 108 | 140 | 108 |
| Sodium Excreted as Urine (mmol/hr) | −73.5 | −56.7 | −73.5 | −56.7 |
| Saline Infusion: | | | | |
| Adjusted Urine Output Rate (ml/hr) | n/a | n/a | 525 | 405 |
| Saline Infusion Rate (ml/hr) | 250 | 250 | 250 | 180 |
| Saline Sodium Concentration (fixed for normal saline), (mmol/L) | 154 | 154 | 154 | 154 |
| Sodium Infused as Saline (mmol/hr) | 38.5 | 38.5 | 38.5 | 27.7 |
| Results: | | | | |
| Net Fluid Loss Rate* (ml/hr) | −275 | −275 | −275 | −345 |
| Sodium Loss Rate** (mmol/hr) | −35.0 | −18.2 | −35.0 | −29.0 |

The net fluid loss rate is the difference between the measured urine output rate and the saline infusion rate. The sodium loss rate is the theoretical amount of sodium removed per hour and is the difference between the sodium infused as normal saline (e.g., at a concentration of 154 mmol/l), and the sodium excreted in the urine (at the concentrations shown in Table 1).

For fluid therapy based on the obtained urine output rate (which, as described previously herein, assumes that Patient 1 and Patient 2 have the same urine sodium concentration because both patients have the same measured urine output rate), Patient 1, with a urine sodium concentration of 140 mmol/L, will see a net sodium loss of 35 mmol/hr. However, Patient 2, with an average urine sodium concentration of 108 mmol/L, but receiving the same 38.5 mmol/L infusion of saline as Patient 1, will see the same net fluid loss as Patient 1 but only a net sodium loss of 18.2 mmol/hr.

For embodiments of the present technology in which fluid therapy is based on the adjusted urine output rate, Patient 1 will have an adjusted urine output rate equal to their measured urine output rate (e.g., because the adjusted urine output rate is based on an expected urine sodium concentration of 140 mmol/L, which is the same as Patient 1's actual urine sodium concentration). Patient 1 will therefore see the same net sodium loss of 35 mmol/L and net fluid loss rate of 275 mmol/hr whether they receive fluid therapy based on their actual or adjusted urine output rate. However, because Patient 2 has a lower-than-expected urine sodium concentration, Patient 2 will have an adjusted urine output rate of 405 mL/hr, lower than their measured urine output rate of 525 mL/hr. Based on this lower adjusted urine output rate, Patient 2 will receive a reduced saline infusion rate of 27.7 mmol/hr and will also see an increased net fluid loss rate of 345 mmol/L and a greater sodium loss rate of 29 mmol/hr. Accordingly, using the adjusted urine output rate can reduce the amount of saline infused into Patient 2 and improve or even optimize Patient 2's net fluid loss rate and the sodium loss rate, without or substantially without changing the therapy outcome for Patient 1. Additionally, it will be appreciated that, while the specific examples described with respect to Table 1 (and, e.g., elsewhere herein) are based on an expected urine sodium concentration of 140 mmol/L, embodiments of the present technology are equally applicable to situations in which patients have other expected urine sodium concentrations. For example, as described above with reference to block 506, the expected urine sodium concentration can be between about 10 mmol/L and about 200 mmol/L, any concentration therebetween, and/or one or more other concentrations including those described elsewhere herein.

B. Diuretic Infusion

For fluid therapy based on the measured/obtained urine output rate, the thresholds for the dose finding mode, diuretic down-titration, and/or therapy escalation were based solely on urine output. As discussed previously, this was based on the assumption that urine sodium concentration was constant and near isotonic (e.g., at an expected urine sodium concentration of 140 mmol/L). For fluid therapy based on the adjusted urine output rate, however, these thresholds are adjusted based on a patient's obtained sodium excretion rate, rather than only the urine output rate. Personalizing these thresholds can lead to only the amount of diuretic necessary for improved or optimal sodium excretion being administered to the patient. For example, patients with sufficiently high sodium excretion can receive reduced amounts of diuretic and/or hydration fluid while patient's with low or sub-optimal sodium excretion can receive an amount of diuretic and/or hydration fluid that is expected to increase the patient's sodium excretion, e.g., to a target or optimal level. To illustrate this, two examples are shown below in Table 2, again for the Patients 1 and 2 described above with reference to Table 1:

TABLE 2

|  | Fluid Therapy based on Obtained Urine Output Rate | | Fluid Therapy based on Adjusted Urine Output Rate | |
| --- | --- | --- | --- | --- |
|  | Patient 1 | Patient 2 | Patient 1 | Patient 2 |
| Urine Sodium Concentration (mmol/L) | 140 | 108 | 140 | 108 |
| Dose Finding: | | | | |
| Dose Finding Urine Rate Threshold (ml/hr) | 525 | 525 | 525 | 681 |
| Sodium Excretion at Dose Finding Threshold (mmol/hr) | −73.5 | −56.7 | −73.5 | −73.5 |
| Therapy Escalation: | | | | |
| Low Urine Rate Threshold (ml/hr) | 325 | 325 | 325 | 421 |
| Sodium Excretion at Low Urine Rate Threshold (mmol/hr) | −45.5 | −35.1 | −45.5 | −45.5 |

TABLE 2-continued

| | Fluid Therapy based on Obtained Urine Output Rate | | Fluid Therapy based on Adjusted Urine Output Rate | |
|---|---|---|---|---|
| | Patient 1 | Patient 2 | Patient 1 | Patient 2 |
| Diuretic Down Titration: | | | | |
| High Urine Rate Threshold (ml/hr) | 1025 | 1025 | 1025 | 1329 |
| Sodium Excretion at High Urine Rate Threshold (mmol/hr) | −143.5 | −110.7 | −143.5 | −143.5 | i. Dose Finding Urine Rate Threshold

Referring to Table 2 (above), the dose finding urine rate threshold is the urine output rate where diuretic dose finding stops. When the measured urine rate exceeds this value during dose finding mode, the system 100 (FIG. 1) stops increasing the diuretic dose and begins continuous diuretic infusion based on the diuretic dose required to reach this level. Additional details regarding the dose finding urine rate threshold can be found in U.S. Pat. No. 11,357,446, filed Dec. 4, 2020, titled "MANAGING FLUID LEVELS IN A PATIENT AND ASSOCIATED DEVICES, SYSTEMS, AND METHODS," which is incorporated by reference herein in its entirety.

For embodiments of the present technology, in which fluid therapy is based on the measured/obtained urine output rate, the dose finding urine rate threshold is fixed and does not change for different urine sodium concentrations. Patient 1 has a high urine sodium concentration (shown here as 140 mmol/L), and accordingly the dose finding mode will end when the patient's urine output rate reaches 525 ml/hr, which is equivalent to a sodium excretion rate of 73.5 mmol/hr. Despite the fact that Patient 2 has a lower urine sodium concentration (shown here as 108 mmol/L), the dose finding mode will end when the patient's urine output rate reaches 525 ml/hr, the same threshold as for Patient 1. However, because Patient 2 has a lower urine sodium concentration than Patient 1, the 525 ml/hr rate for Patient 2 is equivalent to a lower sodium excretion rate of 56.7 mmol/hr (and not, e.g., the 73.5 mmol/hr sodium excretion rate for Patient 1). Thus, when fluid therapy for Patient 2 is based on Patient 2's measured/obtained urine output rate, the dose finding mode will stop at a lower sodium excretion rate, meaning that Patient 2 is expected to have reduced sodium loss at the end of the dose finding mode compared to Patient 1.

For fluid therapy based on the adjusted urine output rate, the dose finding urine rate threshold is personalized to each patient so that the sodium excretion rate at this threshold is the same for all urine sodium concentrations. In the example shown in Table 2, the dose finding urine rate threshold for Patient 1 is unchanged, e.g., because Patient's 1 adjusted urine output rate is the same as their measured/obtained urine output rate. However, because Patient 2 has a lower urine sodium concentration of 108 mmol/L, the dose finding urine rate threshold for Patient 2 is now 681 ml/hr, an increase from the 525 ml/hr rate threshold determined for Patient 2 based on their expected, rather than actual, urine sodium concentration. This, in turn, results in the same sodium excretion of 73.5 mmol/hr for both Patient 1 and Patient 2 at the dose finding urine rate threshold. The 681 ml/hr dose finding urine rate threshold for Patient 2 represents an increase over the 525 ml/hr dose finding urine rate threshold that is associated with (e.g., proportional too) the percent difference between Patient 2's actual and expected urine sodium concentrations (108 mmol/L is ~77.1% of the 140 mmol/L expected urine sodium concentration, and 681 ml/hr is approximately 525 ml/hr/0.771).

Figure 6:
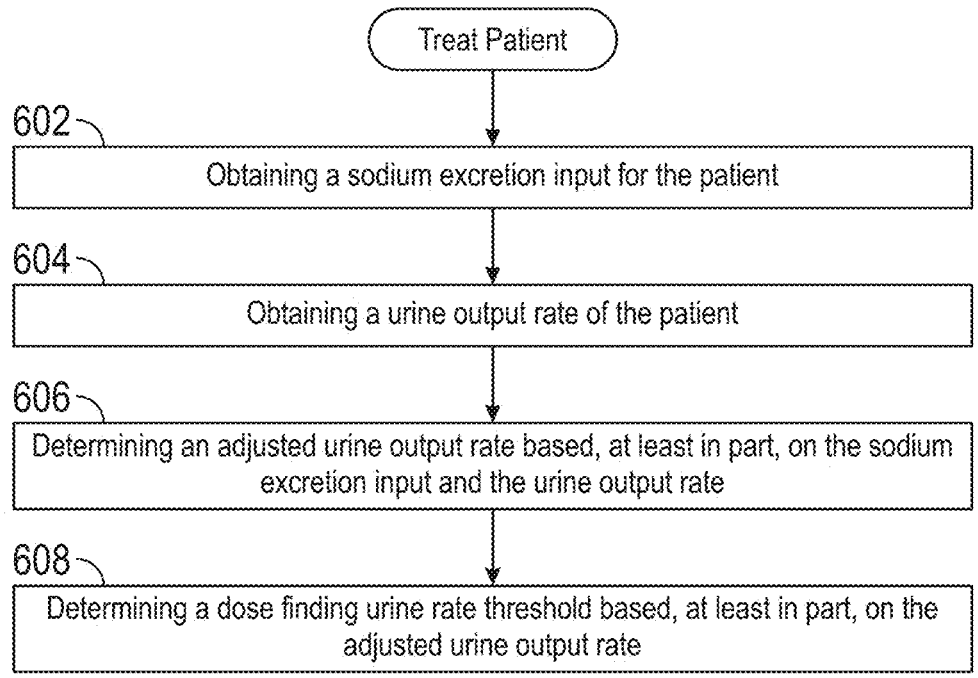
FIGS. 6-9 are flow diagrams of respective methods for treating a patient based on an adjusted urine output rate, each configured in accordance with embodiments of the present technology.

FIG. 6 is a flow diagram of a method 600 for treating a patient, in accordance with embodiments of the present technology. In some embodiments, the method 600 is used to treat the patient for fluid overload by removing fluid from the patient to produce a negative fluid balance (net fluid loss). The method 600 can be performed by any embodiment of the systems and devices described herein, such as the system 100 of FIG. 1. In some embodiments, some or all of the blocks of the method 600 are performed by a system or device including one or more processors and a memory storing instructions that, when executed by the one or more processors, cause the system or device to perform one or more of the blocks described herein. For example, the method 600 can be performed by the controller 140 of the system 100 of FIG. 1 and/or another suitable processor. Optionally, some or all of the blocks of the method 600 can performed automatically or semi-automatically, with little or no human intervention.

The method 600 can begin at block 602 with obtaining a sodium excretion input of a patient. Block 602 can be at least generally similar or identical to block 502 of the method 500, described with reference to FIG. 5A.

At block 604, the method 600 can include obtaining a urine output rate of the patient. Block 604 can be at least generally similar or identical to block 202 of the method 200, described with reference to FIG. 2.

At block 606, the method 600 can include determining an adjusted urine output rate for the patient based, at least in part, on the obtained sodium excretion input (block 602) and the urine output rate (block 606). Block 606 can be at least generally similar or identical to block 506 of FIG. 5A and/or FIG. 5B.

At block 608, the method 600 can include determining a dose finding urine rate threshold based, at least in part, on the adjusted urine output rate. Determining the dose finding urine rate threshold can include adjusting a predetermined dose finding urine rate threshold (e.g., 525 ml/hr) based, at least in part, on a difference (e.g., a ratio) of the patient's actual and adjusted urine output rates. For example, using the data for Patient 2 described previously, the Patient 2's adjusted urine output rate (405 ml/hr) is ~77.1% of Patient 2's measured urine output rate (525 ml/hr). Accordingly, the dose finding urine rate threshold for Patient 2, accounting for Patient 2's adjusted urine output rate, can be ~681 ml/hr (i.e., 525/0.771). As set forth above, the dose finding urine rate threshold is the (adjusted) urine output rate used to determine when diuretic dose finding and/or increases in diuretic doses stops. For example, before the adjusted urine output rate is equal to or greater than the dose finding urine rate threshold, a dosage rate at which diuretic is infused into the patient can be increased from a first dosage rate to a second dosage rate, from a second dosage rate to a third dosage rate, and/or combinations thereof. Once the adjusted urine output rate is equal to or greater than the dose finding urine rate threshold, the diuretic dosage rate can be adjusted to a third or continuous diuretic dosage rate based, at least in part, on the diuretic dosage rate administered to the patient when the adjusted urine output rate equaled or exceeded the dose finding urine rate threshold.

In some embodiments, the method 600 can further include providing fluid therapy to the patient based, at least in part, on the determined dose finding urine rate threshold (block 608). For example, as noted above the dose finding urine rate threshold is the urine output rate where diuretic dose finding stops. Accordingly, providing fluid therapy can include causing a diuretic to be administered to a patient at increasing rates unless or until the patient's adjusted urine output rate exceeds the determined dose finding urine rate threshold (block 608). At this point, the system 100 (FIG. 1) can stop increasing the diuretic dose and begins continuous diuretic infusion based on the diuretic dose required to reach this level.

ii. Low Urine Rate Threshold

Referring again to Table 2 (above), the low urine rate threshold is the urine output rate below which the system 100 (FIG. 1) considers to be low urine output and at which a therapy escalation is suggested to the user. Additional details regarding the dose finding urine rate threshold can be found in U.S. Pat. No. 11,357,446, filed Dec. 4, 2020, titled "MANAGING FLUID LEVELS IN A PATIENT AND ASSOCIATED DEVICES, SYSTEMS, AND METHODS," which is incorporated by reference herein.

For fluid therapy based on the measured/obtained urine output rate, the low urine rate threshold is fixed and does not change for different urine sodium concentrations. Accordingly, for a patient with high urine sodium (e.g., Patient 1, with a urine sodium excretion rate of 140 mmol/L), if the patient's urine output rate drops below 325 ml/hr, equivalent to a sodium excretion rate of 45.5 mmol/hr, the system 100 will suggest that dose finding be restarted, or if the max diuretic rate has been reached, a therapy escalation is recommended. For patients with lower urine sodium levels (e.g., Patient 2, with a urine sodium excretion rate of 108 mmol/L), these patients' urine output rates also have to drop below 325 ml/hr before the system 100 suggests a restart of the dose finding mode or therapy escalation. However, because Patient 2 began therapy with lower urine sodium levels than Patient 1, the equivalent sodium excretion rate for Patient 2 when their urine output rate reaches 325 ml/hr (i.e., 35.1 mmol/L) is now considerably lower compared than the equivalent sodium excretion rate for Patient 1 (i.e., 45.5 mmol/L). This will result in Patient 2 losing less net sodium for a longer period of time, e.g., compared to Patient 1.

For embodiments of the present technology, in which fluid therapy is based on the adjusted urine output rate, the low urine rate threshold is personalized to each patient so that the sodium excretion rate at this threshold is the same for all urine sodium concentrations. In the example shown in Table 2, the low urine rate threshold for Patient 1 is unchanged. However, because Patient 2 has a lower urine sodium concentration of 108 mmol/L, the low urine rate threshold for Patient 1 is now 421 ml/hr (instead of the 325 ml/hr low urine rate threshold determined for Patient 2 based on their expected, rather than actual, urine sodium concentration), and this results in a sodium excretion of 45.5 mmol/hr at the low urine rate threshold, the same as for Patient 1. The 421 ml/hr low urine rate threshold for Patient 2 represents an increase over the 325 ml/hr low urine rate threshold that is associated with (e.g., proportional too) the percent difference between Patient 2's actual and expected urine sodium concentrations (108 mmol/L is ~77.1% of the 140 mmol/L expected urine sodium concentration, and 421 ml/hr is approximately 325 ml/hr/0.771).

Figure 7:
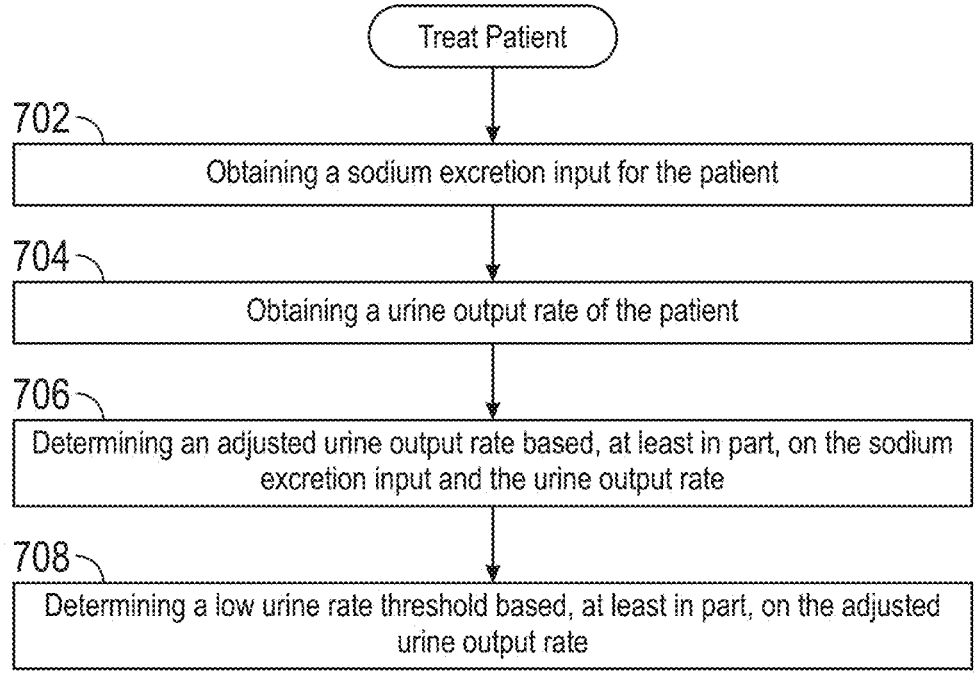

FIG. 7 is a flow diagram of a method 700 for treating a patient, in accordance with embodiments of the present technology. In some embodiments, the method 700 is used to treat the patient for fluid overload by removing fluid from the patient to produce a negative fluid balance (net fluid loss). The method 700 can be performed by any embodiment of the systems and devices described herein, such as the system 100 of FIG. 1. In some embodiments, some or all of the blocks of the method 700 are performed by a system or device including one or more processors and a memory storing instructions that, when executed by the one or more processors, cause the system or device to perform one or more of the blocks described herein. For example, the method 700 can be performed by the controller 140 of the system 100 of FIG. 1 and/or another suitable processor. Optionally, some or all of the blocks of the method 700 can performed automatically or semi-automatically, with little or no human intervention.

The method 700 can begin at block 702 with obtaining a sodium excretion input of a patient. Block 702 can be at least generally similar or identical to block 502 of the method 500, described with reference to FIG. 5A At block 704, the method 700 can include obtaining a urine output rate of the patient. Block 704 can be at least generally similar or identical to block 202 of the method 200, described with reference to FIG. 2.

At block 706, the method 700 can include determining an adjusted urine output rate for the patient based, at least in part, on the obtained sodium excretion input (block 702) and the urine output rate (block 706). Block 706 can be at least generally similar or identical to block 506 of FIG. 5A and/or FIG. 5B.

At block 708, the method 700 can include determining a low urine rate threshold based, at least in part, on the adjusted urine output rate. Determining the low urine rate threshold can include adjusting a predetermined low urine rate threshold (e.g., 325 ml/hr) based, at least in part, on a difference (e.g., a ratio) of the patient's actual and adjusted urine output rates. For example, using the data for Patient 2 described previously, the Patient 2's adjusted urine output rate (405 ml/hr) is ~77.1% of Patient 2's measured urine output rate (525 ml/hr). Accordingly, the low urine rate threshold for Patient 2, accounting for Patient 2's adjusted urine output rate, can be ~421 ml/hr (i.e., 325/0.771). As set forth above, the low urine rate threshold is the urine output rate below which the system 100 (FIG. 1) considers to be low urine output and at which a therapy escalation is suggested to the user. For example, before the adjusted urine output rate is less than or equal to the low urine rate threshold, diuretic can be administered to the patient at a first or continuous infusion rate. Once the adjusted urine output rate is less than or equal to the low urine rate threshold, the diuretic dosage rate can be adjusted to a second or increasing diuretic dosage rate, e.g., to cause or increase fluid loss from the patient.

In some embodiments, the method 700 can further include providing fluid therapy to the patient based, at least in part, on the determined low urine rate threshold (block 708). As noted above, the low urine rate threshold is the urine output rate below which the system 100 (FIG. 1) considers to be low urine output and at which a therapy escalation is suggested to the user. Accordingly, providing fluid therapy to the patient can include suggesting and/or automatically causing a therapy escalation when the patient's adjusted urine output equals or drops below the determined low urine rate threshold (block 708).

iii. High Urine Rate Threshold

Referring again to Table 2 (above), the high urine rate threshold is the urine output rate above which the system 100 (FIG. 1) considers to be high urine output and if this high rate persists for a sustained period, a diuretic infusion rate down-titration is automatically performed. Additional details regarding the dose finding urine rate threshold can be found in U.S. Pat. No. 11,357,446, filed Dec. 4, 2020, titled "MANAGING FLUID LEVELS IN A PATIENT AND ASSOCIATED DEVICES, SYSTEMS, AND METHODS," which is incorporated by reference herein.

For fluid therapy based on the measured/obtained urine output rate, the high urine rate threshold is fixed and does not change for different urine sodium concentrations. In a patient with high urine sodium (e.g., Patient 1, with a urine sodium concentration of 140 mmol/L), if the patient's urine output rate rises above 1025 ml/hr, equivalent to a sodium excretion rate of 143.5 mmol/hr, for a sustained period of time, the system 100 can automatically down-titrate the patient's diuretic infusion rate. Likewise, in a patient with lower urine sodium (e.g., Patient 2, with a urine sodium concentration of 108 mmol/L), the patient's urine output rate also has to rise above 1025 ml/hr for a sustained period of time before the system 100 automatically down-titrates the diuretic infusion rate. However, the equivalent sodium excretion rate at the 1025 ml/hr high urine rate threshold for Patient 2 (i.e., 110.7 mmol/L) is considerably lower than the equivalent sodium excretion rate at the 1025 ml/hr high urine rate threshold for Patient 1 (i.e., 143.5 mmol/L). This will result in Patient 2's diuretic infusion rate being down-titrated at a lower sodium excretion rate than Patient 1's, which is expected to reduce Patient 2's net fluid loss compared to Patient 1.

For embodiments of the present technology, in which fluid therapy is based on the adjusted urine output rate, the high urine rate threshold is personalized to each patient so that the sodium excretion rate at this threshold is the same for all urine sodium concentrations. In the example shown in Table 2, the high urine rate threshold for Patient 1 is unchanged. However, because Patient 2 has a lower urine sodium concentration of 108 mmol/L, the high urine rate threshold for Patient 2 is now 1329 ml/hr (instead of the 1025 ml/hr high urine rate threshold determined for Patient 2 based on their expected, rather than actual, urine sodium concentration). This, in turn, is expected to result in Patient 2 having the same sodium excretion at the high urine rate threshold (i.e., 143.5 mmol/hr) as Patient 1. The 1329 ml/hr high urine rate threshold for Patient 2 represents an increase over the 1025 ml/hr high urine rate threshold that is associated with (e.g., proportional too) the percent difference between Patient 2's actual and expected urine sodium concentrations (108 mmol/L is ~77.1% of the 140 mmol/L expected urine sodium concentration, and 1329 ml/hr is approximately 1025 ml/hr/0.771).

Figure 8:
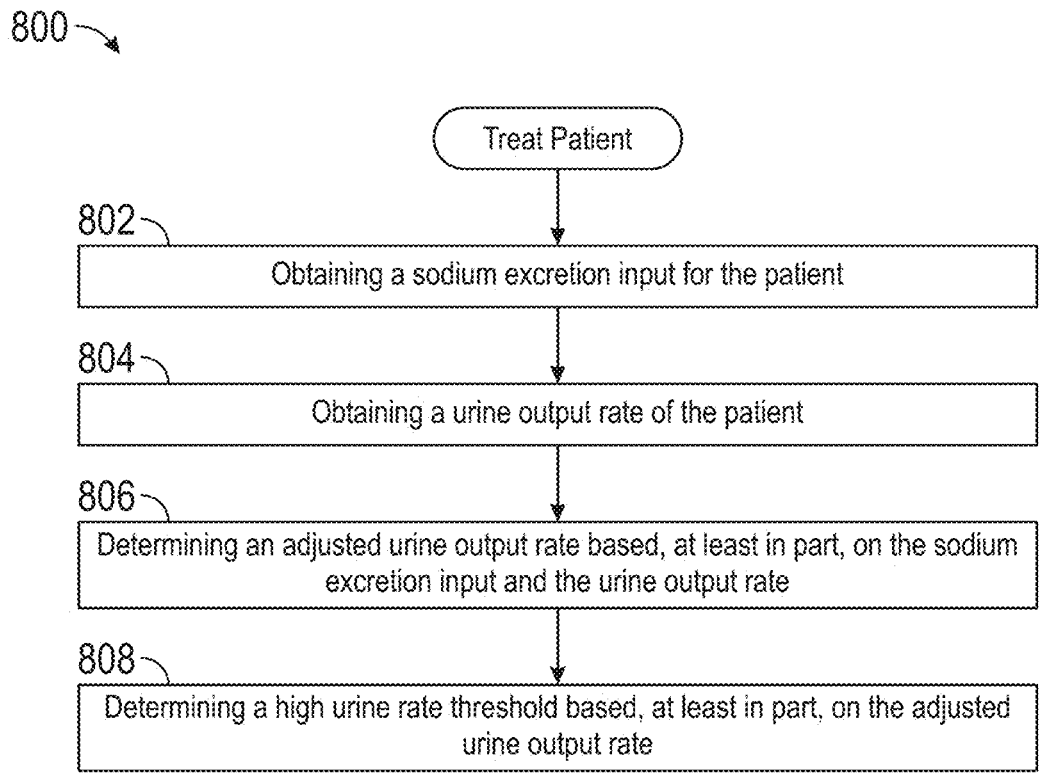

FIG. 8 is a flow diagram of a method 800 for treating a patient, in accordance with embodiments of the present technology. In some embodiments, the method 800 is used to treat the patient for fluid overload by removing fluid from the patient to produce a negative fluid balance (net fluid loss). The method 800 can be performed by any embodiment of the systems and devices described herein, such as the system 100 of FIG. 1. In some embodiments, some or all of the blocks of the method 800 are performed by a system or device including one or more processors and a memory storing instructions that, when executed by the one or more processors, cause the system or device to perform one or more of the blocks described herein. For example, the method 800 can be performed by the controller 140 of the system 100 of FIG. 1 and/or another suitable processor. Optionally, some or all of the blocks of the method 800 can performed automatically or semi-automatically, with little or no human intervention.

The method 800 can begin at block 802 with obtaining a sodium excretion input of a patient. Block 802 can be at least generally similar or identical to block 502 of the method 500, described with reference to FIG. 5A.

At block 804, the method 800 can include obtaining a urine output rate of the patient. Block 804 can be at least generally similar or identical to block 202 of the method 200, described with reference to FIG. 2.

At block 806, the method 800 can include determining an adjusted urine output rate for the patient based, at least in part, on the obtained sodium excretion input (block 802) and the urine output rate (block 806). Block 806 can be at least generally similar or identical to block 506 of FIG. 5A and/or FIG. 5B.

At block 808, the method 800 can include determining a high urine rate threshold based, at least in part, on the adjusted urine output rate. Determining the high urine rate threshold can include adjusting a predetermined high urine rate threshold (e.g., 1025 ml/hr) based, at least in part, on a difference (e.g., a ratio) of the patient's actual and adjusted urine output rates. For example, using the data for Patient 2 described previously, the Patient 2's adjusted urine output rate (405 ml/hr) is ~77.1% of Patient 2's measured urine output rate (525 ml/hr). Accordingly, the high urine rate threshold for Patient 2, accounting for Patient 2's adjusted urine output rate, can be ~1329 ml/hr (i.e., 1025/0.771). As set forth above, the high urine rate threshold is the urine output rate above which the system 100 (FIG. 1) considers to be high urine output and if this high rate persists for a sustained period, a diuretic infusion rate down-titration is automatically performed. For example, before the adjusted urine output rate is equal to or greater than the high urine rate threshold, diuretic can be administered to the patient at a first or continuous infusion rate. Once the adjusted urine output rate is equal to or greater than the high urine rate threshold, the diuretic dosage rate can be decreased to a second or decreasing diuretic dosage rate, e.g., to cause or decrease fluid loss from the patient.

In some embodiments, the method 800 further includes providing fluid therapy based, at least in part, on the determined high urine rate threshold (block 808). As noted above, the high urine rate threshold is the urine output rate above which the system 100 (FIG. 1) considers to be high urine output and, if this high rate persists for a sustained period, a diuretic infusion rate down-titration is suggested and/or automatically performed. Accordingly, providing fluid therapy can include causing a diuretic to be administered to the patient and, when the patient's adjusted urine output rate equals or exceeds the determined high urine rate threshold (block 808), suggesting or automatically causing a down-titration to the patient's diuretic infusion rate.

iv. Sodium Excretion Rate

Figure 9:
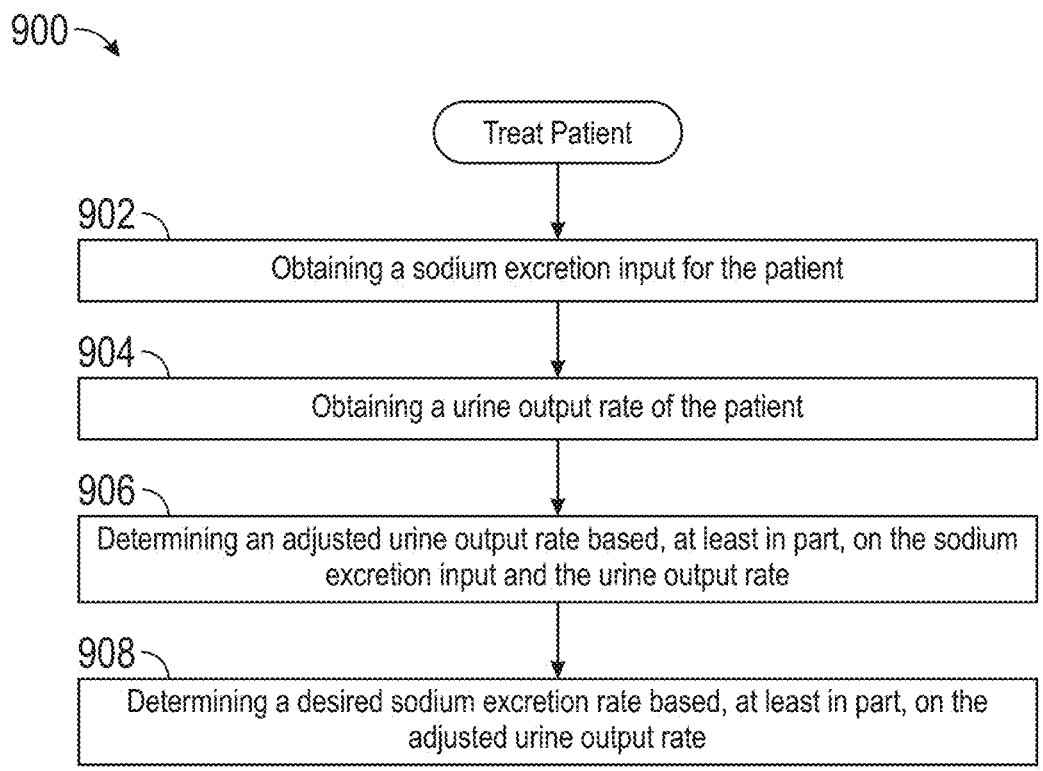

FIG. 9 is a flow diagram of a method 900 for treating a patient, in accordance with embodiments of the present technology. In some embodiments, the method 900 is used to treat the patient for fluid overload by removing fluid from the patient to produce a negative fluid balance (e.g., a net fluid loss). The method 900 can be performed by any embodiment of the systems and devices described herein, such as the system 100 of FIG. 1. In some embodiments, some or all of the blocks of the method 900 are performed by a system or device including one or more processors and a memory storing instructions that, when executed by the one or more processors, cause the system or device to perform one or more of the blocks described herein. For example, the method 900 can be performed by the controller 140 of the system 100 of FIG. 1 and/or another suitable processor. Optionally, some or all of the blocks of the method 900 can performed automatically or semi-automatically, with little or no human intervention.

The method 900 can begin at block 902 with obtaining a sodium excretion input of a patient. Block 902 can be at least generally similar or identical to block 502 of the method 500, described with reference to FIG. 5A.

At block 904, the method 900 can include obtaining a urine output rate of the patient. Block 904 can be at least generally similar or identical to block 202 of the method 200, described with reference to FIG. 2.

At block 906, the method 900 can include determining an adjusted urine output rate for the patient based, at least in part, on the obtained sodium excretion input (block 902) and the urine output rate (block 906). Block 906 can be at least generally similar or identical to block 506 of FIG. 5A and/or FIG. 5B.

At block 908, the method 900 can include determining a desired sodium excretion rate based, at least in part, on the adjusted urine output rate. The desired sodium excretion rate can be a minimum or target sodium excretion rate associated with a net fluid loss goal for the patient, a minimum or target sodium excretion rate at the dose finding diuretic rate threshold, a minimum or target sodium excretion rate at the low urine rate threshold, and/or a minimum or target sodium excretion rate at the high urine rate threshold.

In some embodiments, the method 900 can further include providing fluid therapy to the patient based, at least in part, on the desired sodium excretion rate. The desired sodium excretion rate can include a target sodium excretion rate for the patient at a dose finding diuretic rate threshold (FIG. 6), at the low urine rate threshold (FIG. 7), and/or at a high urine rate threshold (FIG. 8). Accordingly, providing fluid therapy can include causing one or more adjustments to the diuretic infusion rate, as described previously with reference to the method 600, 700, and/or 800, but based or further based on a comparison of the patient's actual sodium excretion rate and the desired sodium excretion rate.

C. Therapy Adjustments to Promote Net Fluid Loss

Figure 10:
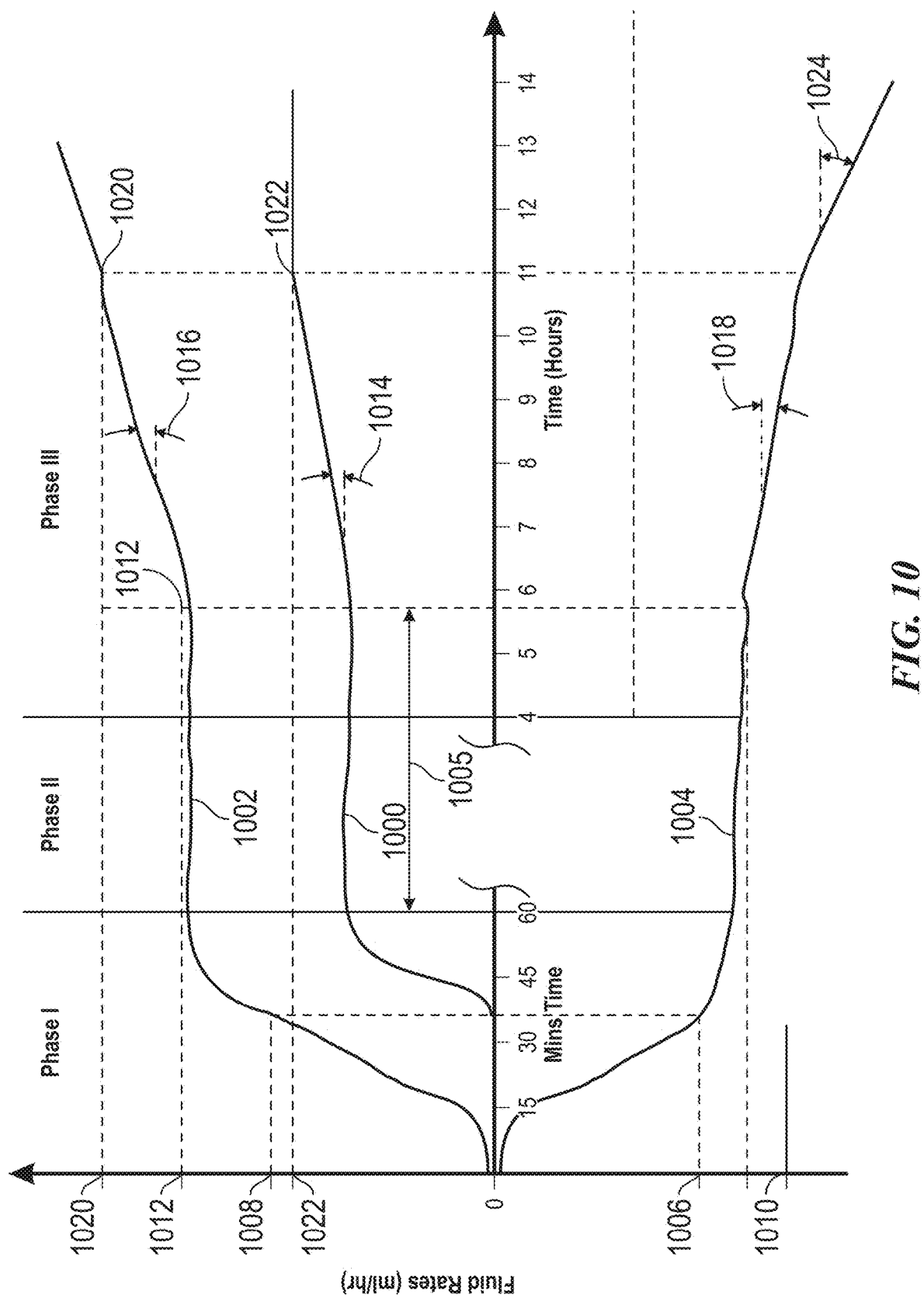
FIG. 10 is a graphical representation showing a relationship between adjusted urine output, hydration fluid infusion, and net fluid loss, in accordance with embodiments of the present technology.

FIG. 10 is a graphical representation showing a relationship between adjusted urine output, hydration fluid infusion, and net fluid loss, in accordance with embodiments of the present technology. Stated differently, FIG. 10 illustrates an exemplary representation for how embodiments of the present technology automatically control the hydration fluid infusion rate 1000 based on the adjusted urine output rate 1002 to achieve a net fluid change (e.g., reduction) rate 1004 in a patient. The control of the hydration fluid infusion rate 1000 can be performed simultaneously to the control of diuretic dosage during Phases I, II and/or III, as shown in FIG. 10.

The adjusted urine output rate 1002 is expected to initially increase during Phase I and thereby result in an increase in the net fluid reduction rate. In some embodiments, the hydration fluid infusion rate 1000 can match the adjusted urine output rate 1002 until a predetermined volume (e.g., at least 150 ml, 200 ml, 250 ml, 300 ml, 400 ml, 500 ml, or within a range of 150-500 ml) of urine has been measured, or a particular period of time (e.g., at least 60 minutes) has elapsed. In some embodiments, the net fluid reduction rate 1004 may substantially equal the adjusted urine output rate 1002 until hydration fluid is infused into the patient. The system 100 (FIG. 1) may determine that hydration fluid is to be added if and when the net fluid reduction rate 1004 falls below a threshold minimum value 1006 or the adjusted urine output rate 1002 exceeds a threshold urine output rate 1008. These threshold values may be received by the controller 140 (FIG. 1) via user input or stored (e.g., as defaults) in the system 100 (e.g., in a memory associated with the controller 140) and/or can be stored in a separate device (e.g., a remote computing device). These threshold values need not occur simultaneously as shown in FIG. 10, but are related and thus are likely to happen at approximately the same time. Alternatively, the system 100 may cause hydration fluid to be infused at near the same time that the diuretic begins to be infused, including when Phase I or a diuretic dosage determining phase is implemented (e.g., reimplemented). Once one or both of the threshold values 1006, 1008 are reached, the system 100 may automatically initiate the infusion of hydration fluid 1000 by actuating an infusion pump (e.g., the hydration fluid infusion pump 126; FIG. 1) to pump hydration fluid from a fluid source (e.g., the fluid source 122; FIG. 1) into the patient. The rate of hydration fluid 1000 infusion may be calculated or determined by the system 100 based on, for example, a difference between the current adjusted urine output rate and a desired net fluid balance rate 1010. For example, if the desired net fluid reduction rate is 200 (ml/hr) and the adjusted urine output rate is 400 ml/hr, then the system 100 may automatically control the infusion of the hydration fluid at a rate of 200 ml/hr.

The system 100 may adjust the infusion rate 1000 of the hydration fluid to maintain a desired net fluid reduction rate 1004, such as a net fluid balance that is constant, between a particular range, or below (i.e., more negative than) a threshold. During an initial phase or period 1005, the hydration fluid may be infused for an hour or until a predetermined amount (e.g., at least 500 ml) of hydration fluid is infused, whichever event occurs first. During the initial phase 1005, the system 100 may match the rate of increase in adjusted urine output rate 1002 with the rate of increase in the hydration fluid infusion 1000. Increasing the hydration fluid at the same rate of increase of the adjusted urine output infuses into the vascular system a substantial amount of hydration fluid. Hydration fluid includes a relatively high concentration of sodium and/or chloride as compared to the typical respective sodium and chloride concentration in urine, and thus infusing hydration fluid into the vascular system increases the sodium and/or chloride level in the blood, even as the patient is excreting urine. Similarly, the hydration fluid may add potassium to the blood at rates greater than the discharge of potassium from urine. In doing so, the initial phase 1005 allows the sodium, chloride, and/or potassium levels in the blood to be artificially increased which provides a safeguard against sodium, chloride, and/or potassium depletion in the patient if the blood volume drops to relatively low levels during the treatment.

After the initial phase 1005, the system 100 may increase the hydration fluid rate 1000 at a rate 1014 less than the current rate increase 1016 of the adjusted urine output rate 1002 (e.g., a proportion of the current rate increase 1016 of about 10%, 20%, 30%, 40%, 50%, 60%, 70%, 80%, 90%, 95%, or within a range of 10%-95%). Alternatively, the system 100 may reduce the rate of increase 1014 for the hydration fluid in response to the adjusted urine output rate 1002 exceeding a first threshold value 1012 (e.g., 400 ml/hr, 420 ml/hr, 440 ml/hr, or within a range of 400-440 ml/hr), above which hydration fluid rate 1000 is not further increased. If and while the adjusted urine output rate 1002 exceeds a first threshold 1012, the system 100 may reduce further the rate of increase 1014 in the hydration fluid 1000 to significantly less than the current rate of increase 1016 of the adjusted urine output rate 1002. For example, while the adjusted urine output rate 1002 is above the first threshold 1012, a further rate of increase 1016 in the adjusted urine output rate 1002 will be matched by a further rate of increase 1014 in the hydration fluid infusion rate 1000, which is increased at only one-half, or in a range of one quarter to three-fourths, the rate of increase 1016 of the adjusted urine output rate 1002. Simultaneously, the rate of decrease 1018 of net fluid reduction 1004 increases due to the greater rate of increase of the adjusted urine output as compared to the lower rate of increase of hydration fluid. As described elsewhere herein, adjusting (e.g., increasing or decreasing) the hydration fluid rate (or rate of increase of the hydration fluid rate) less than that of the adjusted urine output rate can cause net fluid removal of salt within the patient, as well as net fluid loss.

If the adjusted urine output rate 1002 continues to increase and exceeds a second threshold 1020 (e.g., at least 500 ml/hr, 1020 ml/hr, or a range of 500-1020 ml/hr), the system 100 may automatically cease further increases in the hydration fluid rate 1000. While the adjusted urine output rate 1002 is above the second threshold 1020, the system 100 may maintain the hydration fluid rate 1000 at a constant rate 1022 (e.g., 200 ml/hr) regardless of further increases in the adjusted urine output rate 1002. Moreover, the increase in the net fluid reduction rate 1004 has an advantage of reducing the period needed to reach a desired total net fluid reduction. The rate 1024 of net fluid reduction increases due to the increase in the adjusted urine output rate 1002 and the constant hydration fluid rate 1000.

Setting the threshold 1020 for a maximum adjusted urine output beyond which hydration fluid is not further increased is based, in part, on a desire to avoid excessive sodium levels in the patient. The sodium concentration in urine may change throughout the treatment as the physiological state of the patient changes but is nonetheless expected to remain less than (e.g., approximately one-half) the sodium concentration of a saline solution that is expected to be used as the hydration fluid. At high infusion rates of the hydration fluid, the net sodium increase to the patient may become excessive over the course of an hour or more of treatment. To reduce the sodium added to the patient, an upper limit 1022 is applied to the hydration fluid rate 1000. This limit may be indirectly imposed by setting a threshold maximum adjusted urine output rate 1020 beyond which the hydration fluid rate 1000 is not increased as the adjusted urine rate increases beyond the threshold 1020.

As mentioned above, the system 100 may automatically act to reduce high adjusted urine output rates, such as above thresholds 1012 and/or 1020, by reducing the diuretic dosage. The diuretic dosage rate may be increased to dosage levels previously considered inappropriate for fluid reduction treatments. Embodiments of the present technology can administer diuretic at these high levels due to (i) the automatic reduction in the diuretic dosage in response to the adjusted urine output rate 1002 exceeding threshold levels 1012, 1020, and/or (ii) hydration fluid infusion directly into the vascular system of a patient. The infusion of the hydration fluid reduces the risk that the blood volume in the patient will become too low due to a high diuretic dosage. Thus, the diuretic dosage levels 64, 70, 76 described with reference to FIG. 2 may be substantially greater than maximum dosage levels conventionally viewed as appropriate and approved.

The system 100 may store certain limits on the treatment, such as a default fluid balance rate and a maximum net fluid loss. The default net fluid balance rate may be a negative 220 ml/hr or in a range of 150 ml/hr to 260 ml/hr. The maximum net fluid loss limit may be 5 liters (5,000 ml), at which point the system 100 issues a report or alarm, and may stop injecting the diuretic, at least temporarily. An operator may respond to the alarm by entering higher maximum net fluid loss limit, such as in increments of 1 liter. In response to the higher maximum net fluid loss limit, the system 100 may resume Phase III.

A clinical study utilizing embodiments of the present technology consistently reduced the fluid volume in patients faster than conventional standards of care. In previous studies of this patient population, only 47% of patients receiving standard of care achieve a goal of removing four to five liters of fluid volume and it typically takes five days of hospitalization to achieve. In comparison, embodiments of the present technology resulted in removing a net of four to five liters of fluid volume in 24 hours or less. The urine sodium data from this study confirms that embodiments of the present technology also remove significant amounts of salt via high-sodium urine from the patients in addition to net decrease in fluid volume. The urine of patients receiving the conventional standard of care remove substantially only hypotonic urine (e.g., 60-70 mmol sodium). The greater removal of salt achieved via embodiments of the present technology may result in less drive for the patient to reaccumulate fluid after discharge and result in a significant reduction in rehospitalization rates.

In addition to automating delivery of diuretic and hydration fluids based on adjusted urine output, embodiments of the present technology may optimize net fluid volume removal; reduce time needed to achieve desired net fluid removal by allowing physicians to use higher doses or dosage rates of diuretics earlier in treatment compared to the standard of care; avoid or reduce risk of adverse events such as over-diuresis, dehydration, or intravascular depletion; quickly assess if a patient is diuretic resistant; and provide a record of treatment data. Embodiments of the present technology aim to obtain an average net fluid removal rate (average adjusted rate of urine released minus average rate of hydration fluid introduced) of at least 225 ml/hr, which provides 3.4 liters per day of net fluid volume removal based on introducing 2 liters of fluid per day orally or through IV infusion. This rate of fluid removal while replacing sodium may allow a reduction in length of stay (LOS), as well as enable enhanced decongestion.

To achieve these objectives, embodiments of the present technology have a short diuretic dosage determining phase to determine an appropriate continuous diuretic infusion rate, which is then used in a fluid reduction phase during which urine output is continuously monitored and used to assess if the diuretic infusion rate continues to be suitable and to adjust the diuretic infusion rate accordingly. Concurrently, the algorithm controls infusion of hydration fluid to replace a portion of the sodium and fluid removed. The rate of infusion of hydration fluid is at least in part a function of the adjusted rate of urine output.

Figure 11:
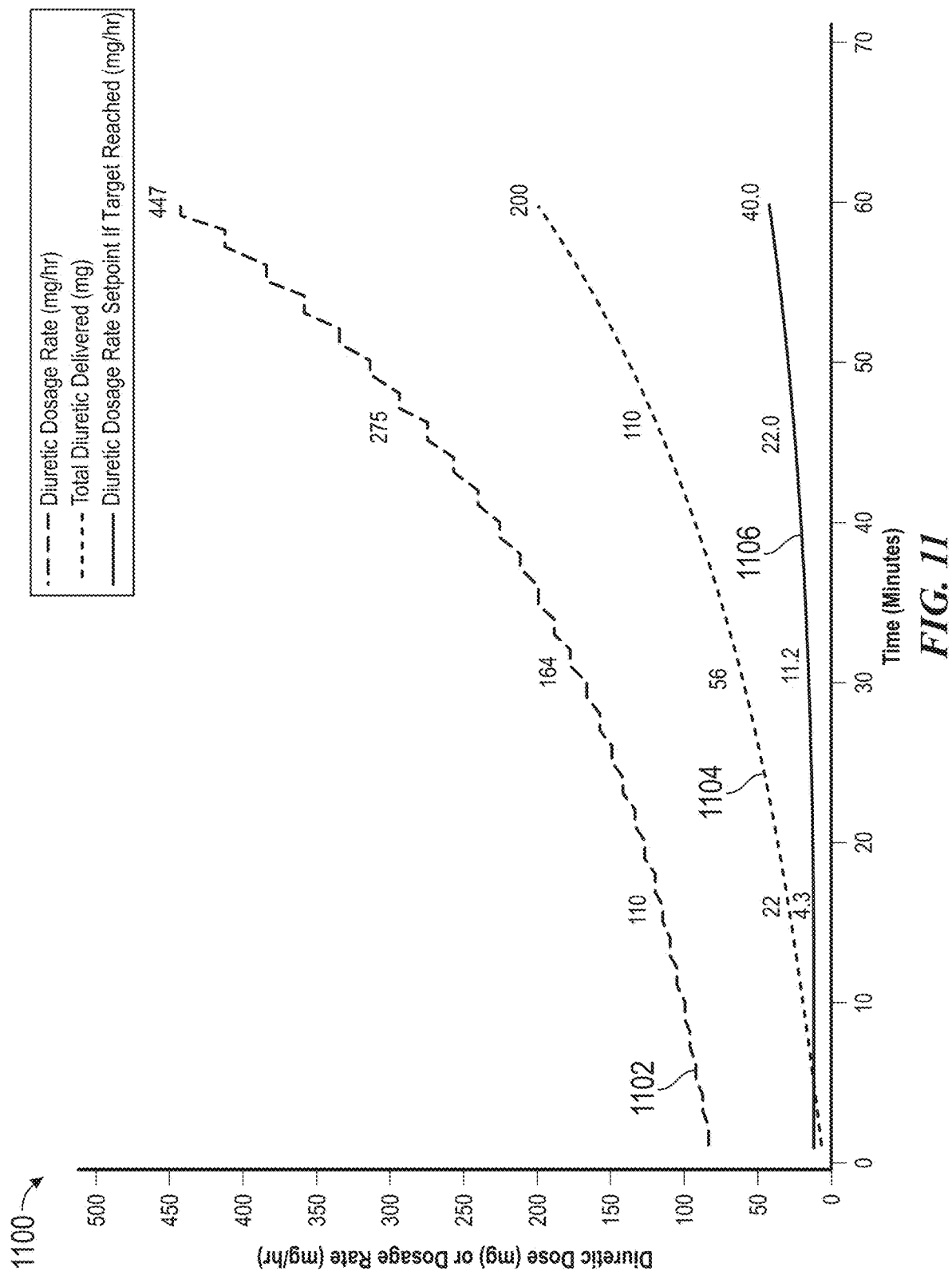
FIG. 11 is a graphical representation showing a relationship between diuretic dosage rate and total diuretic delivered, in accordance with embodiments of the present technology.

FIG. 11 is a graphical representation 1100 showing a relationship between diuretic dosage rate 1102 and total diuretic delivered 1104, in accordance with embodiments of the present technology. The concepts shown and described in FIG. 11 can apply to other aspects of the present technology that relate to the diuretic dosage determining phase, diuretic ramp, and associated features. As shown in FIG. 11, the diuretic dosage rate 1102 can be ramped from an initial rate of about 75 mg/hr to a final rate of about 447 mg/hr within a time period of 60 minutes. As such, the diuretic dosage rate 1102 can increase by about 500% over the time period. As also shown, the diuretic dosage rate 1102 can effectively double within a time period of about 20 minutes.

The total diuretic delivered 1104 (in mg) corresponds to the cumulative amount of diuretic that has been delivered up to that point in time. As previously described, a value of the total diuretic delivered 1104 can be used to determine the value or set point for the diuretic after the adjusted urine output rate of the patient reaches a predetermined threshold. For example, once the adjusted urine output rate reaches the predetermined threshold (e.g., 400 ml/hour, 450 ml/hour, 500 ml/hour, 525 ml/hour, 550 ml/hour, or within a range of 400-550 ml/hour), a value of the diuretic dosage rate may be set to be a percentage (e.g., 20%) of a value of the total diuretic delivered 1104 up to that point in time. As shown in FIG. 11, the diuretic dosage rate setpoint 1106 corresponds to 20% of the value of the total diuretic delivered 1104. It is noted that the values shown in FIG. 11 may be used for a furosemide diuretic. Use of other diuretics may require different dosage rates, but similar general principles as those described herein would apply.

i. Reramp or Rapid Increase of Diuretic Dosage Rate

Figure 12:
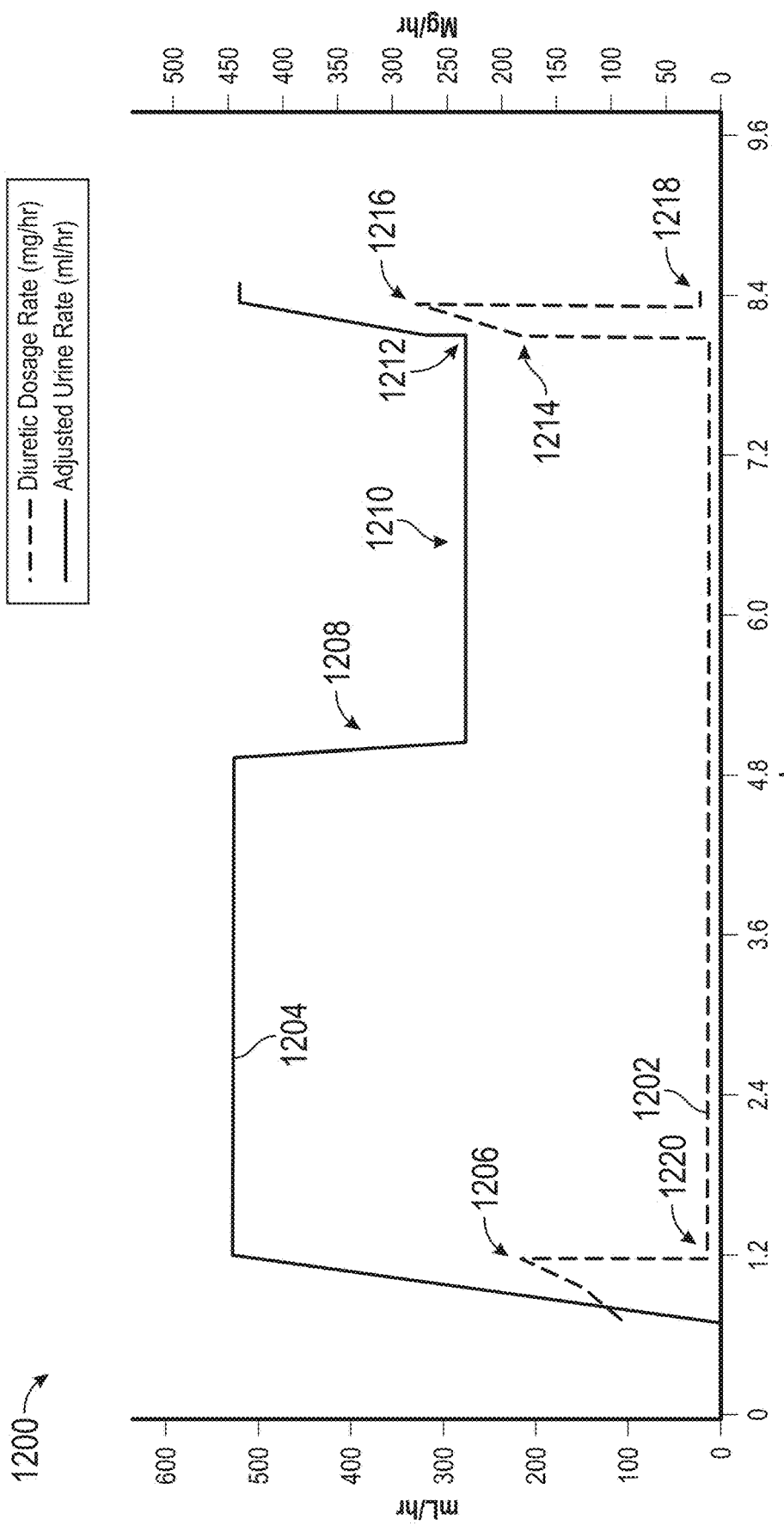
FIG. 12 is a graphical representation of diuretic dosage rate and corresponding adjusted urine output rate, in accordance with embodiments of the present technology.

FIG. 12 is a graphical representation 1200 of diuretic dosage rate 1202 and corresponding adjusted urine output rate 1204, in accordance with embodiments of the present technology. The graphical representation 1200 generally illustrates the continuous infusion and/or fluid reduction phase of fluid therapy described previously herein. Initially, the diuretic dosage rate 1202 is increased or ramped until the adjusted urine rate 1204 reaches a predetermined threshold, which in this instance is approximately 525 ml/hr. Once the predetermined threshold is reached, the ramp of the diuretic dosage rate 1202 ceases (e.g., at point 1206), and the diuretic dosage rate 1202 is set to a percentage (e.g., 10%, 15%, 20%, 25%, 30%, or within a range of 10-30%) of the total diuretic dose delivered to the patient up to that point in time. For the embodiment illustrated in FIG. 12, the ramp of the diuretic dosage rate 1202 completes at the point 1206 after 50 mg of diuretic has been delivered, and the diuretic dosage rate 1202 is thereafter set to 10 mg/hr or 20% of the total diuretic infused up to that point. The decreased diuretic dosage rate 1202 can then be provided at the continuous rate of 10 mg/hr until the system causes the dosage rate 1202 to be adjusted, e.g., in response to the adjusted urine rate dropping and/or a regulatory limit being met.

As illustrated by line 1208, the adjusted urine rate 1204 may decrease to a lower adjusted urine rate, as illustrated by line 1210. This drop is adjusted urine rate 1204 may be due to a change in the patient's response to the diuretic or other condition. Though the adjusted urine rate after line 1208 is now below the predetermined threshold of 525 ml/hour, the diuretic dosage rate may not be immediately adjusted. Instead, as described elsewhere herein (e.g., with reference to FIGS. 1 and 2), the diuretic dosage rate 1202 may be adjusted only after (i) the adjusted urine rate is below another predetermined threshold (e.g., a second predetermined threshold) (e.g., 250 ml/hr, 300 ml/hr, 325 ml/hr, 350 ml/hr, 400 ml/hr, or 250-400 ml/hr) for a predetermined period of time (e.g., 2 hours, 2.5 hours, or 3 hours), or (ii) more than a predetermined amount (e.g., 100 ml, 125 ml, 150 ml, 175 ml) of debt has accumulated over the second predetermined period of time. Using these time-weighted average measurements of adjusted urine rate, as opposed to an instantaneous drop below the first predetermined threshold, to initiate a reramp of the diuretic dosage can prevent unnecessary reramps when, for example, the drop in adjusted urine rate 1204 is due merely to a blocked Foley catheter, temporary faulty sensor, or other related short-term measure. At point 1212, the system determines that the average adjusted urine rate has been below the second predetermined threshold for 3 hours. As a result, a reramp of the diuretic dosage rate 1202 is initialized and the dosage rate is set to the rate at which the previous ramp ceased (as shown at point 1214), in this instance approximately 180 mg/hr. The diuretic dosage rate 1202 is then ramped according to the same conditions described elsewhere herein (e.g., with reference to FIGS. 1 and 2). In some embodiments, the initial diuretic dosage rate 1202 for the reramp can be set to a rate below (e.g., 10%, 20%, 30%, or 10-30% below) the rate at which the previous ramp ceased. Once the adjusted urine output rate reaches the predetermined threshold, the ramp of the diuretic dosage rate 1202 ceases (i.e., at point 1216), and the diuretic dosage rate 1202 is set to a percentage, in this instance 20%, of the total diuretic dose delivered to the patient up to that point. For the embodiment illustrated in FIG. 12, the ramp of the diuretic dosage rate 1202 completes at the point 1218 after 50 mg of diuretic has been delivered via the second ramp or a total of 100 mg of diuretic (i.e., 50 mg from the second ramp and 50 mg previously delivered to the patient during the previous ramp ending at point 1220), and the diuretic dosage rate 1202 is thereafter set to 20 mg/hr or 20% of the total diuretic infused up to that point. The decreased diuretic dosage rate 1202 can then be provided at the continuous rate of 20 mg/hr until the system causes the dosage rate 1202 to be adjusted.

ii. Down-titration or Decrease of Diuretic Dosage Rate

Figure 13:
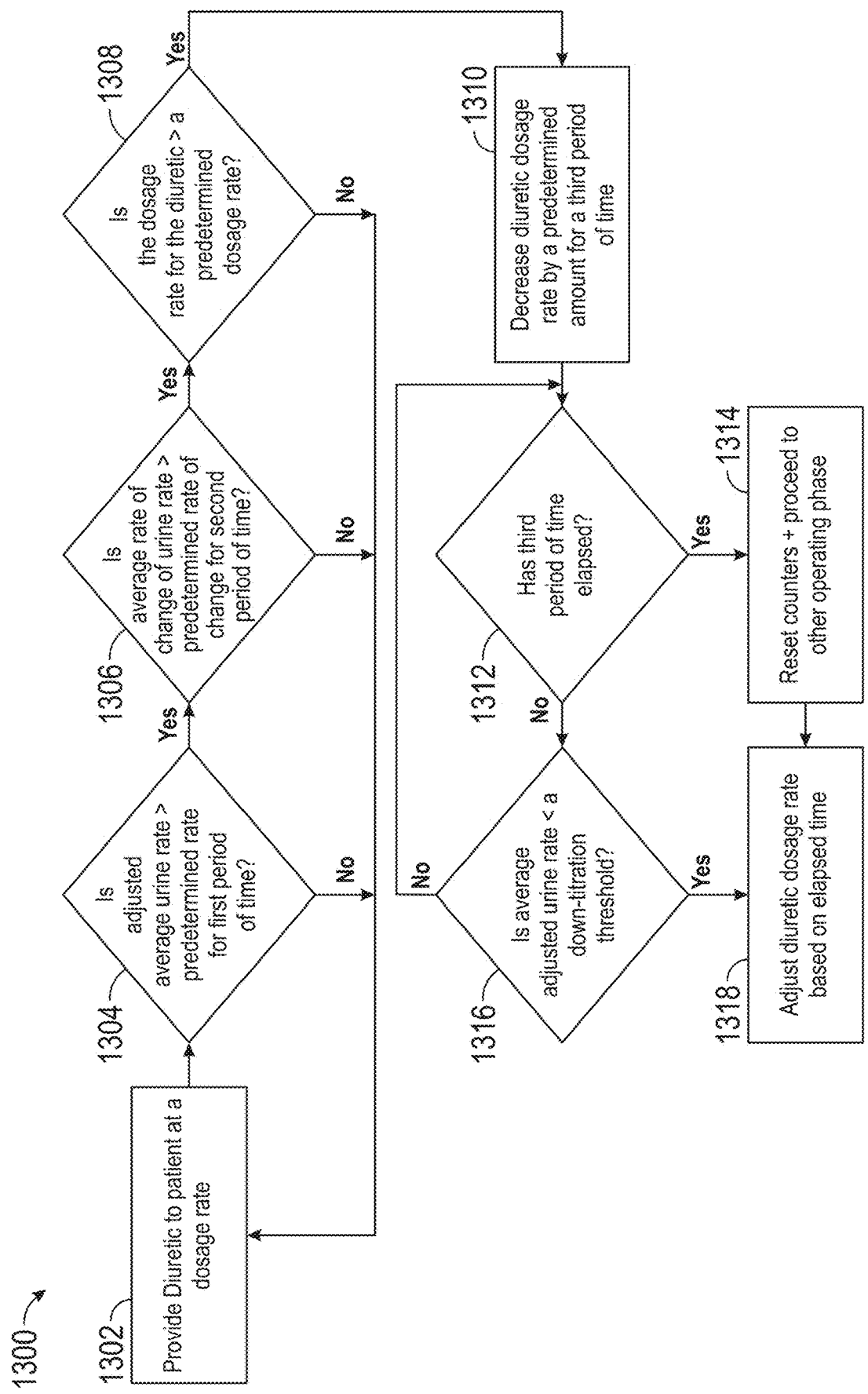
FIG. 13 is a flowchart illustrating down-titration or decrease of a diuretic dosage rate, in accordance with embodiments of the present technology.

FIG. 13 is a flowchart 1300 illustrating down-titration of a diuretic dosage rate, in accordance with embodiments of the present technology. Fluid removal from a patient can often lead to physiological changes, which may cause an increased response to a diuretic dosage. In such instances, the adjusted urine rate may remain higher than clinically desired, which when left untreated over long periods of time can cause electrolyte loss and/or hypotension. Additionally, in such instances, it may also be desired to not simply cease providing diuretic to the patient, as doing so could unnecessarily cause fluid therapy to have to be restarted and thus increase the overall time needed to remove a net amount of excess fluid. To mitigate such issues, embodiments of the present technology can include a methodology for down-titrating (i.e., reducing) the diuretic dosage without setting the diuretic dosage to zero.

As shown in FIG. 13, the flowchart 1300 begins by providing a diuretic to a patient at a dosage rate (process portion 1302), as described elsewhere herein. The system then determines whether each one of a set of conditions is met, and if so down-titrates the diuretic dosage. The set of conditions can include determining whether the average adjusted urine rate is greater than a predetermined rate for a first period of time (e.g., 2 hours, 3 hours, 4 hours, or within a range of 2-4 hours) (process portion 1304). The predetermined rate can be dependent on whether hydration fluid is being infused to the patient. If hydration fluid is being infused to the patient, the predetermined rate can be 900 ml/hr, 950 ml/hr, 1025 ml/h, 1100 ml/hr, or within a range of 900-1100 ml/hr. If no hydration fluid is being infused to the patient, the predetermined rate can be 400 ml/hr, 450 ml/hr, 525 ml/hr, 600 ml/hr, or within a range of 400-600 ml/hr. The set of conditions can further include determining whether an average rate of increase of the adjusted urine rate (e.g., a positive slope) is greater than a predetermined rate of change (e.g., 30 ml/hr$^2$, 40 ml/hr$^2$, 50 ml/hr$^2$, 60 ml/hr$^2$, 70 ml/hr$^2$, or within a range of 30-70 ml/hr$^2$) for a second period of time (e.g., 1 hour, 2 hours, 3 hours, or within a range of 1-3 hours) (process portion 1306). The set of conditions can further include determining whether the diuretic dosage rate is greater than a predetermined dosage rate (e.g., 8 mg/hr, 10 mg/hr, 12 mg/hr, or within a range of 8-12 mg/hr) (process portion 1308). In some embodiments, if any one of the set of conditions is not met, the system will not down-titrate the diuretic dosage and will revert to process portion 1302. If each one of the set of conditions is met, the system will proceed to decrease the diuretic dosage rate by a predetermined. In some embodiments, the system may proceed to decrease the diuretic dosage per process portion 1310 if two of the three conditions are met.

In some embodiments, by requiring all or a majority of the set of conditions to be met, the system avoids unnecessarily decreasing the diuretic dosage rate, thereby allowing adjusted urine rates to remain high and preventing fluid therapy from being unnecessarily interrupted. For example, whereas other methodologies may interrupt fluid therapy and decrease the diuretic dosage rate when the adjusted urine rate is merely above a predetermined threshold, embodiments of the present technology may only decrease the dosage rate (per process portion 1310) when the adjusted urine rate is both high and increasing. Stated differently, such a methodology can prevent the diuretic dosage rate from being unnecessarily decreased when adjusted urine rates are high (e.g., above the predetermined rate) temporarily but are trending downward to eventually be below the predetermined rate. In doing so, embodiments of the present technology can also prevent or inhibit over-diuresis or excess fluid loss and/or electrolyte loss, as well limit unnecessary exposure of the patient to additional medical agents. Additionally or alternatively, down-titrating the diuretic dosage rate, as opposed to ceasing the diuretic dosage can be beneficial, as fluid therapy can be continued (albeit at lower urine rates) without the need to restart completely. Additionally or alternatively, by mitigating the potential hazard of diuretic overshooting (e.g., when ramping the diuretic during the dosage determining phase) and limiting overexposure of the patient to the diuretic, there may be additional regulatory benefits to having the down-titration methodology.

If the set of conditions are met, the system can decrease the diuretic dosage rate by a predetermined percentage (e.g., 20%, 25%, 30%, or within a range of 20-30%) for a third period of time (e.g., 2 hours, 3, hours, 4 hours, or within a range of 2-4 hours) (process portion 1310). After decreasing the diuretic dosage, the system checks whether the third period of time has elapsed (process portion 1312), and if so, resets the counters associated with the set of conditions (process portion 1314). In such embodiments, the diuretic dosage rate can remain at the down-titrated levels or be adjusted based on the subsequent operating phase of therapy. If the third period of time has not elapsed, the system may determine whether the average adjusted urine rate is greater than a down-titration threshold (process portion 1318). The down-titration threshold may be based on the predetermined rate used in process portion 1304. For example, the down-titration threshold can be 100 ml/hr less than the predetermined rate. In such embodiments, the down-titration threshold can be 800 ml/hr, 850 ml/hr, 925 ml/h, 1000 ml/hr, or within a range of 800-1000 ml/hr when hydration fluid is being infused, and 300 ml/hr, 350 ml/hr, 425 ml/hr, 500 ml/hr, or within a range of 300-500 ml/hr if no hydration fluid is being infused. If the average adjusted urine rate is less that the down-titration threshold, the diuretic dosage rate can be adjusted (e.g., increased) based on the elapsed time at that moment in time. In some embodiments, the predetermined percentage that the diuretic dosage rate decreased per process portion 1310 is reduced by the fraction of the third period that has elapsed. For example, assuming the predetermined percentage was 25%, if the diuretic dosage rate drops below the down-titration threshold 90 minutes after the down-titration began (i.e., half of the third period of time of 180 minutes), the diuretic dosage rate would then be increased to be only half of the predetermined percentage, or 12.5%. After the diuretic dosage is adjusted per process portion 1318, the system can reset the counters associated with the set of conditions (process portion 1314), as previously described.

Figure 14:
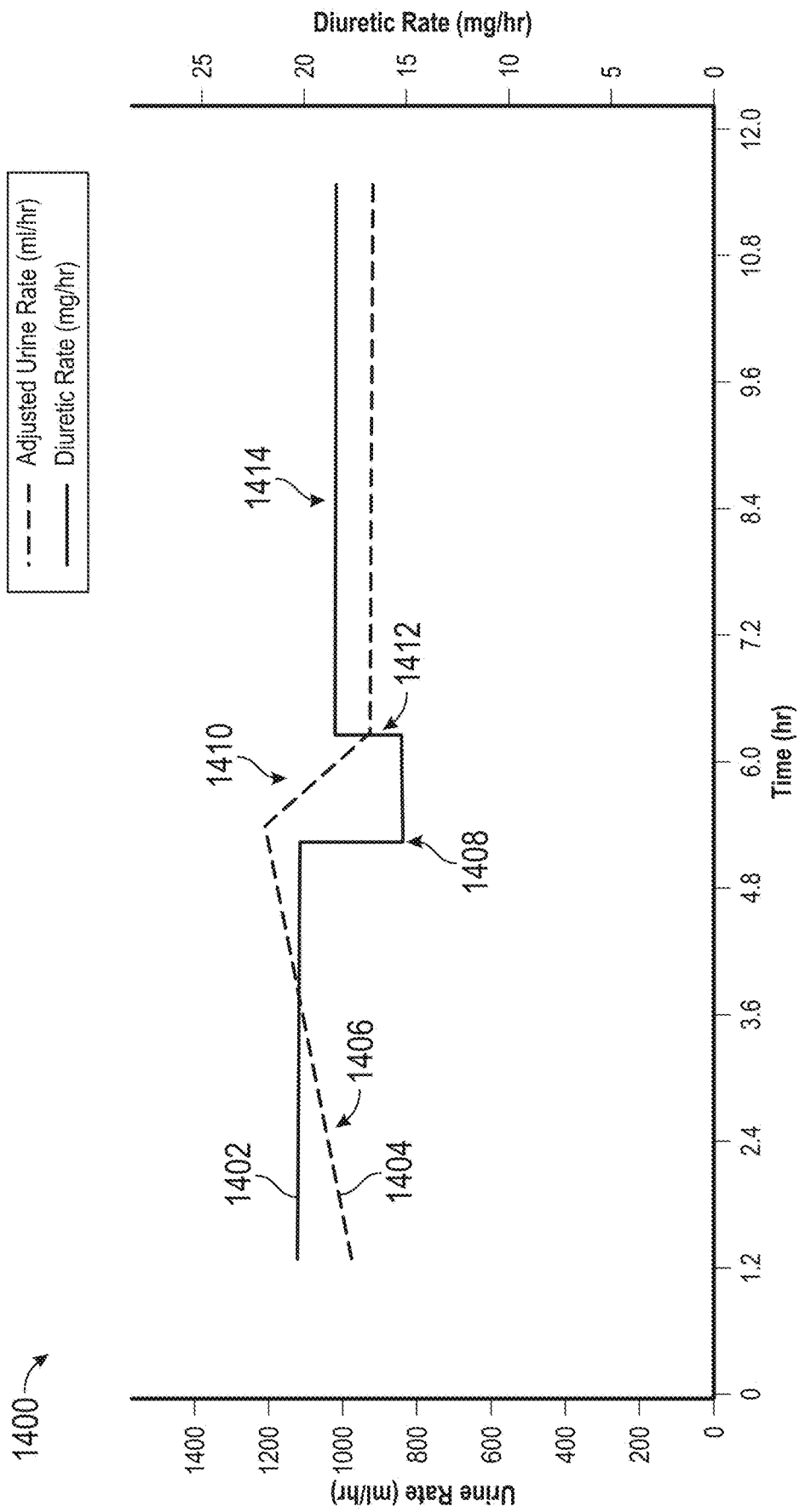
FIG. 14 is a graphical representation of down-titrating or decreasing a diuretic dosage rate, in accordance with embodiments of the present technology.

FIG. 14 is a graphical representation 1400 of down-titrating a diuretic dosage rate 1402, in accordance with embodiments of the present technology. The graphical representation 1400 generally illustrates the embodiments described with reference to FIG. 13. As shown in FIG. 14, the diuretic dosage rate 1402 is initially steady at a rate of approximately 20 mg/hour, and the adjusted urine rate 1404 is increasing at a rate greater than 50 ml/hr$^2$. Approximately at point 1406, the adjusted urine output exceeds 1025 ml/hr. At point 1408, each one of the set of conditions described with reference to FIG. 13 is met. That is, (i) the average adjusted urine rate 1404 has been above a predetermined rate of 1025 ml/hr for a first period of time of 3 hours, (ii) the average rate of change of the adjusted urine rate is above a predetermined rate of change of 50 ml/hr$^2$, and (iii) the diuretic dosage rate is above a predetermined dosage rate of 10 mg/hr. As such, the diuretic dosage rate at point 1408 is decreased by a predetermined percentage, in this instance 25%, from 20 mg/hr to 15 mg/hr for a period of time, in this instance 3 hours.

Decreasing the diuretic dosage rate 1402 causes the adjusted urine rate to drop, as illustrated by portion 1410. Once the adjusted urine output reaches a down-titration threshold of 925 ml/hr at point 1412, the diuretic dosage rate is increased. Since the down-titration threshold was reached one hour after the down-titration event (i.e. ⅓ of the 3 hour period of time), the diuretic dosage rate is subsequently set to be 1/3 (33%) of the original 25% reduction or 8.3% less than the original diuretic dosage rate of 20 mg/hr. Accordingly, the diuretic dosage rate is set to approximately 18.3 mg/hr. Point 1414 corresponds to 3 hours of elapsed time since the down-titration event, and thus at that time the down-titration check is re-engaged. Stated differently, the down-titration feature is disabled for a period of time, in this instance 3 hours, after a down-titration event occurs.

Figure 15:
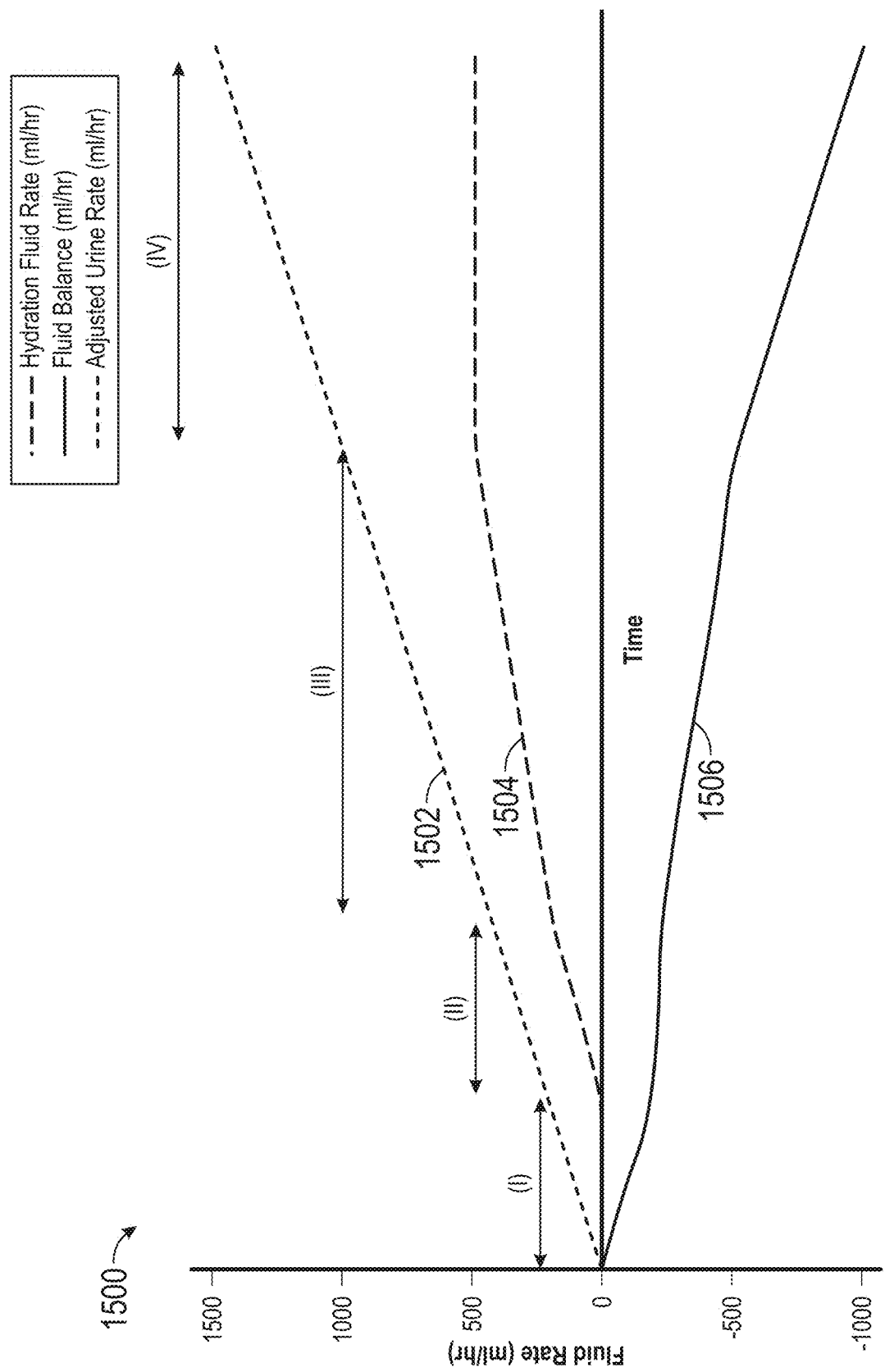
FIG. 15 is a graphical representation of the relationship between adjusted urine output rate, hydration fluid infusion rate, and net fluid balance, in accordance with embodiments of the present technology.

FIG. 15 is a graphical representation 1500 of the relationship between adjusted urine output rate 1502, hydration fluid infusion rate 1504, and net fluid balance 1506, in accordance with embodiments of the present technology. As described elsewhere herein, embodiments of the present technology enable the adjusted urine rate 1502 of a patient to be rapidly increased by increasing the diuretic dosage rate provided to the patient at a relatively fast rate, e.g., exponentially during the diuretic dosage determining phase (as described elsewhere herein). Simultaneously, hydration fluid can be infused at rates equal to or less than the diuretic dosage rates, to thereby enable net fluid balance over time. The hydration fluid infusion, e.g., during the diuretic dosage determining phase, may be done to "jumpstart" the patient's urination response. In some embodiments, the initial hydration fluid infusion can cause the patient to respond to the diuretic more quickly, and so, without being bound by theory, the initial hydration fluid may be infused in order to inhibit intravascular depletion, as well as inhibit drops in cardiac output and renal perfusion. As described elsewhere herein, in some embodiments the algorithm may control the hydration fluid infusion rate to substantially match (e.g., at least 90% or 100%) the adjusted urine output rate while administering the initial diuretic dosage (e.g., during the diuretic dosage ramp) for an initial amount (e.g., at least the initial 150 ml, 200 ml, 250 ml, 300 ml, 400 ml, 500 ml, or within a range of 150-500 ml) of adjusted urine output or for a first time period (e.g., the first hour, 2 hours, or 3 hours), whichever comes first. It is noted that the need for initial hydration fluid infusion may be determined more by the desire to achieve better patient response to the diuretic, as opposed to decreasing salt concentration of fluid levels, which may be the driving need for hydration fluid infusion in subsequent operating phases. For example, hydration fluid infusion during the fluid reduction phase or continuous infusion phase may be done to optimize net fluid removal while also avoiding safety risks, e.g., by maintaining a safe blood pressure and sodium level. That is, a goal of infusing hydration fluid is to maximize net fluid removal while avoiding adding too much sodium back and/or in any way increasing the likelihood of causing a hypotensive state.

As shown in FIG. 15, the adjusted urine rate may be classified into different regions, including a first region (I), a second region (II), a third region (III), and a fourth region (IV), with each subsequent region corresponding to a higher adjusted urine output rate 1502. The first region (I) can correspond to an adjusted urine rate below a first threshold (e.g., 175 ml/hr, 225 ml/hr, 275 ml/hr, or within a range of 175-275 ml/hr), the second region (II) can correspond to an adjusted urine rate between the first threshold and a second threshold (e.g., 375 ml/hr, 425 ml/hr, 500 ml/hr, or within a range of 375-500 ml/hr), the third region (III) can correspond to an adjusted urine rate between the second threshold and a third threshold (e.g., 975 ml/hr, 1025 ml/hr, 1100 ml/hr, or within a range of 975-1100 ml/hr), and the fourth region (IV) can correspond to a urine rate above the third threshold. As shown in FIG. 15, as the adjusted urine rate 1502 increases, the hydration rate 1504 generally increases as well, but at a rate less than that of the adjusted urine rate 1502. In doing so, the net fluid balance 1506 decreases (i.e., becomes more negative) and net fluid loss increases. The adjusted urine output rate is continuously calculated throughout the treatment so the algorithm can respond to changes quickly and/or adjust one or more of the treatment thresholds accordingly (e.g., as described previously with reference to FIGS. 5A-9). For example, flow, weight, volume, and/or other characteristics indicative of volumetric rate change of the urine may be measured every minute, and the adjusted urine output rate 1502 can be calculated every minute based on a previous time period (e.g., 5 minutes, 10 minutes, 20 minutes, or within a range of 5-20 minutes). Assessing how much hydration fluid to infuse may occur every minute.

As shown in FIG. 15, when the adjusted urine rate 1502 is in the first region (I) below the first threshold, the hydration fluid rate 1504 may be zero, or a minimum amount (e.g., 10 ml/hr), e.g., to keep the vein pressurized and open (referred to as a Keep Vein Open (KVO) rate). Since the adjusted urine output is low in the first region, rehydration is less or not necessary. Also, as a general goal is to maximize net fluid removal, no infusion of hydration fluid may be provided when the adjusted urine rate 1502 is in the first region (I). As previously described, in some embodiments, the hydration fluid rate 1504 may match the adjusted urine rate 1502 for a first period of time or until a minimum amount of hydration fluid is infused.

When the adjusted urine rate 1502 is in the second region (II), substantially all (e.g., at least 90% or 100%) of the urine volume in the second region (II) (i.e., between the first and second thresholds) is replaced by hydration fluid, e.g., to ensure the kidneys are getting enough fluid and salt, and to inhibit a hypotensive state.

When the adjusted urine rate 1502 is in the third region (III), substantially all (e.g., at least 90% or 100%) of the urine volume in the second region (II) between the first and second thresholds can be replaced by hydration fluid, and 40%, 45%, 50%, or a range of 40-50% of the urine volume above in the third region (III) and above the second threshold is replaced. By only replacing a portion of the adjusted urine rate above the second threshold, net fluid balance as well as salt concentration can be decreased. Urine typically has less sodium concentration than blood or normal saline, which is approximately 154 mmol/L. As such, replacing urine with an equal amount of hydration fluid may result in increased and undesirable sodium levels. In some embodiments, providing saline or hydration fluid at a rate of more than 50% of the adjusted urine rate can increase the risk of giving the patient more sodium than they are releasing. Accordingly, limiting the hydration fluid rate to 50% can protect patients having low sodium urine, while also enabling patients having higher sodium urine to experience faster net fluid and sodium removal. The adjusted urine output rate in the third region (III) can serve as an indication that the kidneys are functioning well and not in a hypotensive state, and so the reduced hydration fluid rate is more acceptable.

When the adjusted urine rate 1502 is the fourth region (IV), substantially all (e.g., at least 90% or 100%) of the urine volume in the second region (II) between the first and second thresholds can be replaced by hydration fluid, 40%, 45%, 50%, or a range of 40-50% of the adjusted urine volume in the third region (III) between the second and third thresholds can be replaced, and none of the adjusted urine volume in the fourth region (IV) above the third threshold is replaced. In doing so, the net fluid balance can be further decreased.

It was previously thought that removing high excess fluid amounts (e.g., greater than 5 L) within 24 hours with conventional therapy methods would be dangerous and could cause hypotension. However, embodiments of the present technology have shown that even at relatively high adjusted urine rates (e.g., at adjusted urine rates within the third or fourth regions), removing excess fluid amount (e.g., via infusing hydration fluid at 50% replacement) of at least 5 L per day can be safely done with limited or no risk of kidney failure.

In some embodiments, a net fluid loss limit may be set based on the adjusted urine rate at the time and/or region the adjusted urine rate is in, with the net fluid loss limit increasing for each subsequent region. For example, the net fluid loss limit for (i) the first region (I) can be 80 ml/hr, 90 ml/hr, 100 ml/hr, or within a range of 80-100 ml/hr, (ii) the second region (II) can be 100 ml/hr, 130 ml/hr, 160 ml/hr, or within a range of 100-160 ml/hr, (iii) the third region (III) can be 250 ml/hr, 400 ml/hr, 500 ml/hr, or within a range of 250-500 ml/hr, and (iv) the fourth region (IV) can be 500 ml/hr, 750 ml/hr, 900 ml/hr, or within a range of 500-1000 ml/hr.

IV. FLUID THERAPY BASED ON SODIUM OUTPUT RATE

Some embodiments described herein use the difference between a patient's actual and expected sodium excretion to determine an adjusted urine output rate for the patient and provide fluid therapy based on the adjusted urine output rate. This represents one approach to providing individualized fluid therapy that accounts for specific characteristics of the patient's urine to improve the patient's net sodium and/or fluid loss. In these and/or other embodiments, another approach to providing individualized fluid therapy can be based on the patient's sodium excretion or output rate. The patient's actual sodium excretion (e.g., sodium output rate) can be used to determine a sodium output rate for the patient using Equation 2 below:

$$\text{Sodium Output Rate}\left(\frac{\text{mmol}}{\text{hr}}\right) = \frac{\text{Sodium Excretion Input}\left(\frac{\text{mmol}}{\text{L}}\right) * \text{Urine Output Rate}\left(\frac{\text{ml}}{\text{hr}}\right)}{1000\left(\frac{\text{ml}}{\text{L}}\right)} \qquad \text{Eq. 2}$$

The sodium excretion input can include a measured sodium concentration in urine excreted by the patient. In some embodiments, the sodium excretion input can include a value based on a conductivity of the urine excreted by the patient. For example, a patient's urine conductivity can be used as or to calculate a surrogate for directly measuring the patient's urine sodium levels. Urine conductivity is correlated with urine sodium output and is thus a good surrogate for urine sodium detection. Additionally, measuring conductivity is less expensive and generally easier relative to measuring sodium concentration directly, provides a signal that can be more robust and/or less noisy, and unlikely sodium concentration can be measured in real-time. Moreover, sodium is not the only electrolyte present in urine so, relative to measuring urine sodium concentration, measuring urine conductivity can account for sodium and other electrolytes (e.g., potassium) in urine.

Providing fluid therapy based on the patient's sodium output rate is another way to address patient-to-patient variation in sodium excretion and provide patient-specific fluid therapy. In at least some aspects, providing fluid therapy based on the patient's sodium output rate can be mathematically equivalent to providing fluid therapy based on the patient's adjusted urine output rate. This is because the patient's sodium output rate is the same as the patient's adjusted urine output rate multiplied by the patient's expected sodium excretion level and divided by 1000. For example, using the data from Table 1 (above) for Patient 2, Patient 2 had an adjusted urine output rate of 405 mL/hr, an expected sodium excretion level of 140 mmol/L, and a sodium output rate of 56.7 mmol/hr. Multiplying 405 mL/hr by 140 mmol/L equals 56,700 (mL/hr) (mmol/L); dividing 56,700 (mL/hr) (mmol/L) by 1000 mL/L is 56.7 mmol/hr, the same as Patient 2's sodium output rate (calculated as: (urine rate of 525 ml/hr*urine sodium level of 108 mmol/L)/1000=56.7 mmol/hr sodium output rate). Thus, while the discussion of FIGS. 16-26B describe providing fluid therapy based on a patient's sodium output and/or sodium output rate, it will be appreciated that this discussion applies equally to providing fluid therapy based on adjusted urine output rate and/or other ways of expressing one or more of the inputs (e.g., urine output, urine output rate, urine sodium concentration) used to calculate these values.

In some embodiments, the system can begin providing fluid therapy based on measured urine output and, at some time later, switch to using the patient's sodium output rate as the primary input for fluid therapy. In at least some embodiments, for example, the initial ramp and initial fluid match can be based on (e.g., solely based on) a patient's measured urine output and/or urine output rate. While the system may begin calculating the patient's sodium output rate as soon as therapy starts, the system can wait to use sodium output rate as the primary input for fluid therapy until, e.g., a predetermined amount of time (e.g., up to 1 hour, 2 hours, 3 hours, 4 hours, 5 hours, or 6 hours) has passed and/or a predetermined quantity of sodium excretion input data (e.g., up to 1 hour, 2 hours, 3 hours, 4 hours, 5 hours, or 6 hours of sodium excretion input data) has accumulated. Before the predetermined amount of time has passed and/or the predetermined quantity of sodium excretion input data has accumulated, the system can assume that the patient's sodium excretion input is a predetermined amount (e.g., 140 mmol/L).

Figure 16:
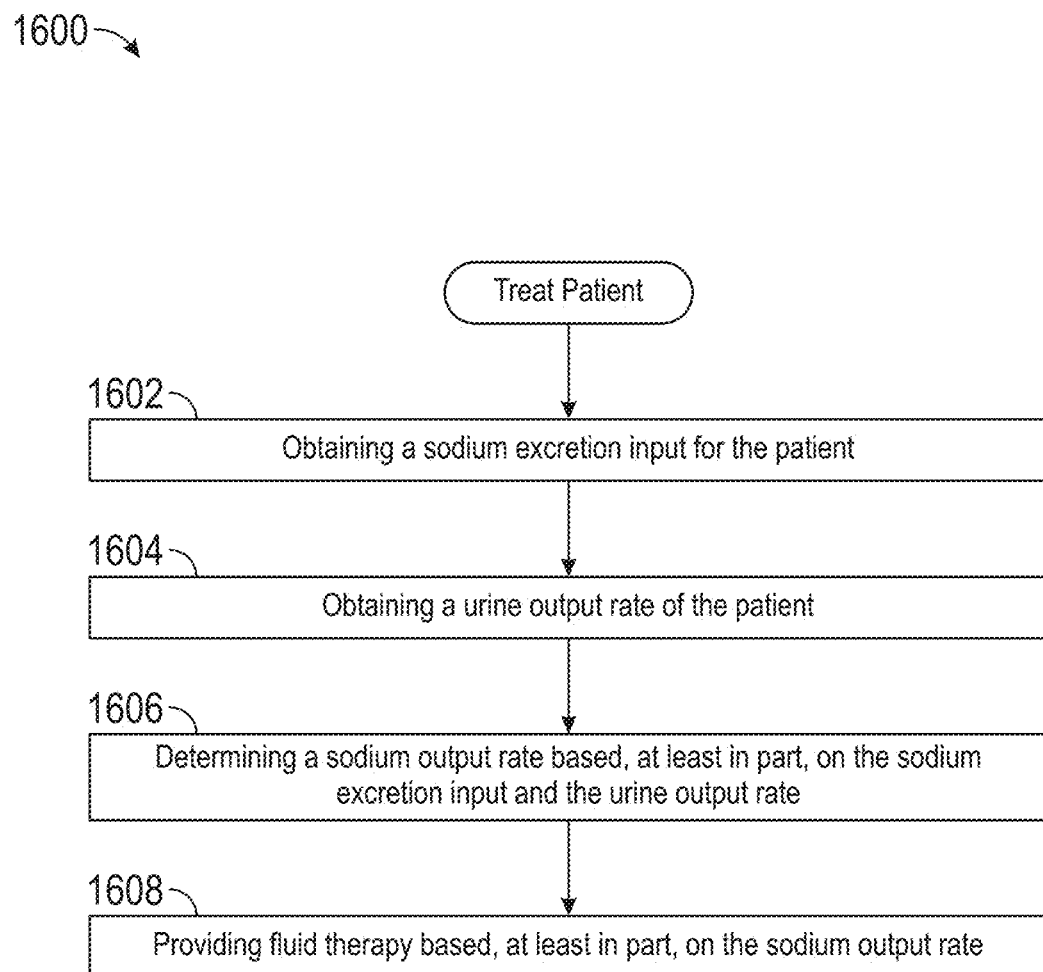
FIG. 16 is a flow diagram of a method for treating a patient based on a sodium output rate, in accordance with embodiments of the present technology.

FIG. 16 is a flow diagram of a method 1600 for treating a patient based on a sodium output rate, in accordance with embodiments of the present technology. In some embodiments, the method 1600 is used to treat the patient for fluid overload by removing fluid from the patient to produce a negative fluid balance (e.g., a net fluid loss) and/or a negative sodium balance (e.g. net sodium loss). The method 1600 can be performed by the embodiments of the systems and devices described herein, such as the system 100 of FIG. 1. In some embodiments, some or all of the blocks of the method 1600 are performed by a system or device including one or more processors and a memory storing instructions that, when executed by the one or more processors, cause the system or device to perform one or more of the blocks described herein. For example, the method 1600 can be performed by the controller 140 of the system 100 of FIG. 1 and/or another suitable processor. Optionally, some or all of the blocks of the method 1600 can performed automatically or semi-automatically, with little or no human intervention.

The method 1600 can begin at block 1602 with obtaining a sodium excretion input for the patient. Block 1602 can be at least generally similar or identical to block 502 of the method 500, described with reference to FIG. 5.

At block 1604, the method 1600 can include obtaining a urine output rate of the patient. Block 1604 can be at least generally similar or identical to block 202 of the method 200, described with reference to FIG. 2.

At block 1606, the method 1600 can include determining a sodium output rate for the patient based, at least in part, on the obtained sodium excretion input (block 602) and the urine output rate (block 1604). The sodium output rate can be based on the expected sodium excretion input. In some embodiments, for example, determining the sodium output rate includes determining the sodium output rate by multiplying the sodium excretion input by the urine output rate and dividing by 1000, as shown in Equation 2 (above). In some embodiments, determining the sodium output rate can include determining or measuring the sodium output rate without obtaining the urine output rate (block 1604).

At block 1608, the method 1600 can include providing fluid therapy based, at least in part, on the sodium output rate (block 1606). In some embodiments, block 1608 includes causing a diuretic to be provided to the patient at a dosage rate, e.g., as described previously herein with reference to block 204 of the method 200 (FIG. 2). Additionally, or alternatively, block 1608 can include causing a hydration fluid to be provided to the patient at a hydration rate, e.g., as described previously herein with reference to block 1606 of the method 200 (FIG. 2). In these and/or other embodiments, block 1608 can include adjusting at least one of the dosage rate of the diuretic or the hydration rate of the hydration fluid, e.g., as described previously herein with reference to block 208 of the method 200 (FIG. 2). The adjustment to the dosage rate of the diuretic and/or the hydration rate of the hydration fluid can be adjustments to an initial dosage rate of the diuretic and/or an initial hydration rate of the hydration fluid administered to the patient, e.g., at the start of therapy and/or to induce fluid loss before the patient has produced sufficient urine to obtain a sodium excretion input (block 502). Each of the hydration rate, the diuretic dosage rate, the adjustment to the hydration rate, and the adjustment to the diuretic dosage rate can be determined as described previously herein with reference to the corresponding portions of the method 200, but with the determination based on the sodium output rate (block 1606) instead of the urine output rate (block 202). For example, the various thresholds and/or rates described previously herein with reference to the patient's urine output and/or urine output rate can be converted to sodium output and/or sodium output rates using, e.g., Equation 2 (above). As described previously herein, basing fluid therapy on the sodium output rate (block 1606) is expected to account for, or at least partially account for, variations in the sodium excretion level of the patient and, in turn, increase or optimize the patient's urine output. For example, because Equation 2 relies on the patient's (actual) sodium excretion input, patient-to-patient variation in sodium excretion levels are automatically accounted for when determining the patient's sodium output rate and/or one or more of the rates and/or thresholds associated with the patient's fluid therapy. The increased or optimized efficacy of fluid therapy (e.g., as measured by patient weight and/or fluid loss) maintains a similar renal safety profile to therapy based on urine volume alone.

Figure 17:
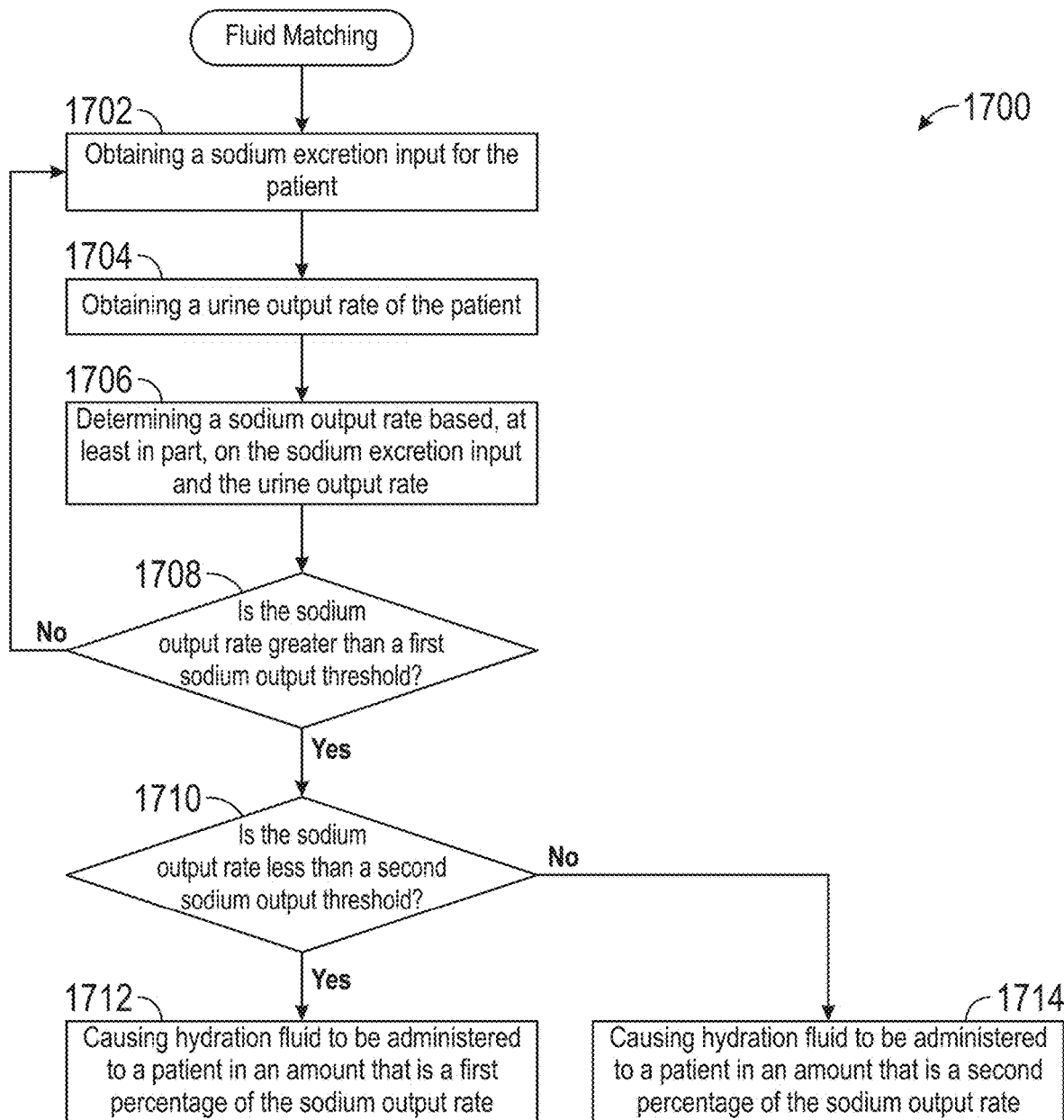
FIG. 17 is a flow diagram of a method for matching urine output with hydration fluid based on a sodium output rate, in accordance with embodiments of the present technology.

FIG. 17 is a flow diagram of a method 1700 for matching urine output with hydration fluid based on a sodium output rate, in accordance with embodiments of the present technology. The method 1700 can be performed by the embodiments of the systems and devices described herein, such as the system 100 of FIG. 1. In some embodiments, some or all of the blocks of the method 1700 are performed by a system or device including one or more processors and a memory storing instructions that, when executed by the one or more processors, cause the system or device to perform one or more of the blocks described herein. For example, the method 1700 can be performed by the controller 140 of the system 100 of FIG. 1 and/or another suitable processor. Optionally, some or all of the blocks of the method 1700 can be performed automatically or semi-automatically, with little or no human intervention.

The method 1700 can begin at block 1702 with obtaining a sodium excretion input for the patient. Block 1702 can be at least generally similar or identical to block 502 of the method 500, described with reference to FIG. 5. In some embodiments, before the patient has output 1 L of urine, block 1706 can include assuming that the sodium excretion input is a predetermined or expected sodium excretion level (e.g., 140 mmol/L).

At block 1704, the method 1700 can include obtaining a urine output rate of the patient. Block 1704 can be at least generally similar or identical to block 202 of the method 200, described with reference to FIG. 2.

At block 1706, the method 1700 can include determining a sodium output rate for the patient based, at least in part, on the obtained sodium excretion input (block 1702) and the urine output rate (block 1704). Block 1706 can be at least generally similar or identical to block 1606 of the method 1600, described with reference to FIG. 16.

At block 1708, the method 1700 can include determining whether the sodium output rate (block 1706) is greater than a first sodium output threshold. In some embodiments, the first sodium output threshold is a sodium output rate equivalent to a urine output rate of up to 225 ml/hr, which may be based on a given sodium excretion input (e.g., a sodium output rate of 31.5 mmol/hr,). In these and/or other embodiments, the first sodium output threshold is a sodium output rate that, for a given urine sodium concentration, is equivalent to a urine output rate of up to 175 ml/hr, 275 ml/hr, or within a range of 175-275 ml/hr. If the sodium output rate is not greater than the first sodium output threshold (e.g., block 1708, NO), then the method 1700 can include repeating one or more of blocks 1702-1706, e.g., without adjusting or causing an adjustment to hydration fluid administration. If, on the other hand, the sodium output rate is greater than the first sodium output threshold (e.g., block 1708, YES), the method can continue to block 1710.

At block 1710, the method 1700 can include determining whether the sodium output rate (block 1706) is less than a second sodium output threshold. The second sodium output threshold can include a sodium output rate that, for a given urine sodium concentration, is equivalent to a urine output rate of up to 375 ml/hr, 425 ml/hr, 500 ml/hr, or within a range of 375-500 ml/hr (e.g., a sodium output rate of 52.5-59.5 mmol/L). As If the sodium output rate is less than the first sodium output rate threshold (e.g., block 1710, YES), then the method 1700 can continue to block 1712. If, on the other hand, the sodium output rate is not less than the second sodium output threshold (e.g., block 1710, NO), the method can continue to block 1714.

At block 1712, the method 1700 can include causing hydration fluid to be administered to the patient in an amount that is a first percentage of the sodium output rate (block 1706). The first percentage can be at least 50%, 60%, 70%, 80%, 90% (or any percentage therebetween, such as 64%), up to 100% of the sodium output rate. Accordingly, block 1712 can include causing hydration fluid to be administered to the patient at a rate that is at least 50%, 60%, 70%, 80%, 90% (or any percentage therebetween), up to 100% of the sodium output rate.

At block 1714, the method 1700 can include causing hydration fluid to be administered to the patient in an amount that is a second percentage of the sodium output rate. The second percentage can be up to 10%, 20%, 30%, 40%, or 50% (or any percentage therebetween, such as 37%) of the sodium output rate. Accordingly, block 1714 can include causing hydration fluid to be administered to the patient at a rate that is up to 10%, 20%, 30%, 40%, or 50% of the sodium output rate.

In some embodiments, if the patient's sodium output rate (block 1706) exceeds a third sodium output threshold, there is not a corresponding change in the hydration fluid administration. The third sodium output threshold can include a sodium output rate that, for a given urine sodium concentration, is equivalent to a urine output rate of at least or up to 975 ml/hr, 1025 ml/hr, 1075 ml/hr, 1125 ml/hr, 1175 ml/hr, 1225 ml/hr, 1275 ml/hr, 1325 ml/hr, 1375 ml/hr, 1425 ml/hr, 1475 ml/hr, 1525 ml/hr, 1575 ml/hr, 1625 ml/hr, 1675 ml/hr, 1725 ml/hr, 1775 ml/hr, 1825 ml/hr, 1875 ml/hr, 1925 ml/hr, 1975 ml/hr, 2025 ml/hr, 2075 ml/hr, or within a range of 975-2075 ml/hr. If the patient's sodium output rate exceeds the third threshold, the method 1700 can include continuing to cause hydration fluid to be administered to the patient without, e.g., adjusting the hydration fluid infusion rate to account for this increase in the patient's sodium output rate.

Table 3 below illustrates a relationship between urine sodium (mmol/L), sodium output (mmol/hr) (also referred to herein as sodium excretion input), and urine rate (mL/hr) (also referred to herein as urine output rate) for a given urine rate (mL/hr). For example, a patient having a urine sodium of 130 mmol/L will need to have a urine rate of 242 mL/hr to achieve a sodium output rate of 31.5 mmol/hr.

TABLE 3

| | | Urine Sodium (mmol/L) | | | | | | | |
|---|---|---|---|---|---|---|---|---|---|
| Urine Sodium (mmol/L) 140 | Sodium Output Rate (mmol/hr) | 140 | 130 | 120 | 110 | 100 | 90 | 80 | 70 |
| Minimum Infusion Rate (mL/hr) | 10 | Urine Rate (mL/hr) | | | | | | | |
| Desired fluid balance (mL/hr) 225 | 31.5 | 225 | 242 | 263 | 286 | 315 | 350 | 394 | 450 |
| Full match range (mL/hr) 425 | 59.5 | 425 | 458 | 496 | 541 | 595 | 661 | 744 | 850 |
| Max balance (mL/hr) 1025 | 143.5 | 1025 | 1104 | 1196 | 1305 | 1435 | 1594 | 1794 | 2050 |

Figure 18:
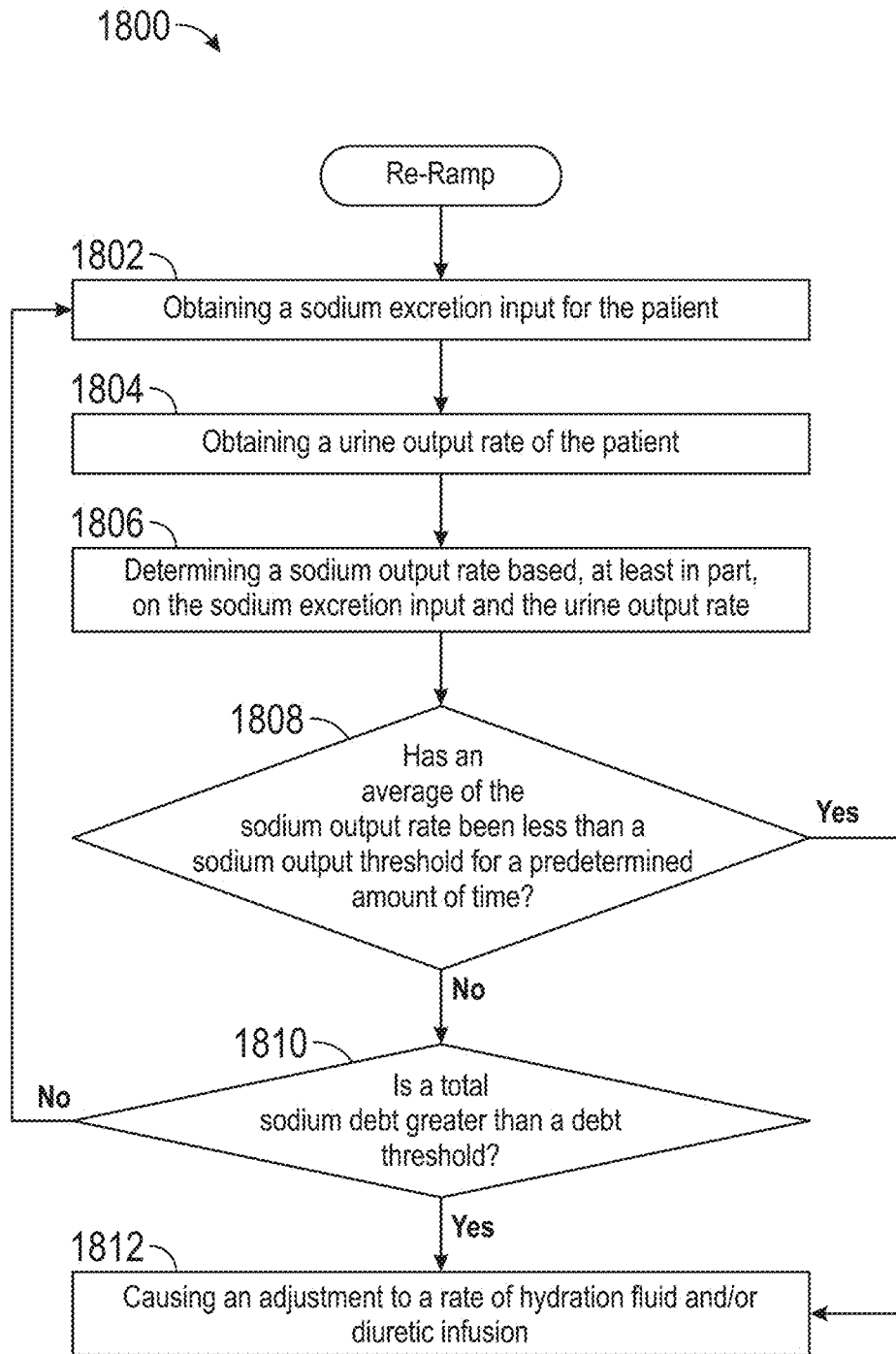
FIG. 18 is a flow diagram of a method for re-ramping a patient's fluid therapy based at least in part on the patient's sodium output rate, in accordance with embodiments of the present technology.

FIG. 18 is a flow diagram of a method 1800 for re-ramping a patient's fluid therapy based at least in part on the patient's sodium output rate, in accordance with embodiments of the present technology. The method 1800 can be performed by the embodiments of the systems and devices described herein, such as the system 100 of FIG. 1. In some embodiments, some or all of the blocks of the method 1800 are performed by a system or device including one or more processors and a memory storing instructions that, when executed by the one or more processors, cause the system or device to perform one or more of the blocks described herein. For example, the method 1800 can be performed by the controller 140 of the system 100 of FIG. 1 and/or another suitable processor. Optionally, some or all of the blocks of the method 1800 can performed automatically or semi-automatically, with little or no human intervention.

The method 1800 can begin at block 1802 with obtaining a sodium excretion input for the patient. Block 1802 can be at least generally similar or identical to block 502 of the method 500, described with reference to FIG. 5.

At block 1804, the method 1800 can include obtaining a urine output rate of the patient. Block 1804 can be at least generally similar or identical to block 202 of the method 200, described with reference to FIG. 2.

At block 1806, the method 1800 can include determining a sodium output rate for the patient based, at least in part, on the obtained sodium excretion input (block 1802) and the urine output rate (block 1804). Block 1806 can be at least generally similar or identical to block 1606 of the method 1600, described with reference to FIG. 16.

At block 1808, the method 1800 includes determining whether an average of the sodium output rate has been less than a sodium output rate threshold for a predetermined amount of time. The sodium output rate threshold can be a rate of sodium output that, for a given urine sodium concentration, is equivalent to a urine output rate of up to 250 ml/hr, 300 ml/hr, 325 ml/hr, 350 ml/hr, 400 ml/hr, or 250-400 ml/hr. The predetermined amount of time can be up to 2 hours, 2.5 hours, 3 hours, or 4 hours. If the average of the sodium output rate has been less than a sodium output rate threshold for the predetermined amount of time (block 1808, YES), the method 1808 can continue to block 1812. If not (block 1808, NO), the method 1808 can continue to block 1810.

At block 1810, the method 1800 can include determining whether a total sodium debt is greater than a debt threshold. Sodium "debt" can be defined as the area on a plot between the sodium output rate and a set rate (e.g., 45.5 mmol/hr, equivalent to a urine output rate of 325 mL/hr with a urine sodium concentration of 140 mmol/L), and can represent how much of and for how long the sodium output rate has been below the set rate. If, for example, the set rate is 45.5 mmol/hr and, after 1 hour, the patient's sodium output rate is 24.4 mmol/hr (meaning the patient has lost 24.4 mmol in 1 hour and not the expected 45.5 mmol/hr) then the patient has a sodium debt of 21.1 mmol. The debt threshold can be an amount of sodium that, for a given urine sodium concentration, is equivalent to a urine output of up to 100 mL, 125 mL, 150 mL, or 175 ml, for a given urine sodium concentration. For example, in at least some embodiments the debt threshold is 21 mmol, which is equivalent to 150 mL of urine having a sodium concentration of 140 mmol/L. If the total sodium debt is greater than the debt threshold (block 1810, YES), the method can continue to block 1812. If not (block 1810, NO), the method can end and/or return to block 1802 and/or repeat one or more of blocks 1802-1808.

At block 1812, the method 1800 can include causing an adjustment to a rate of hydration fluid and/or diuretic infusion. The adjustment can include re-ramping the patient's diuretic infusion rate, as described previously herein with reference to at least block 208 of the method 200.

Figure 19:
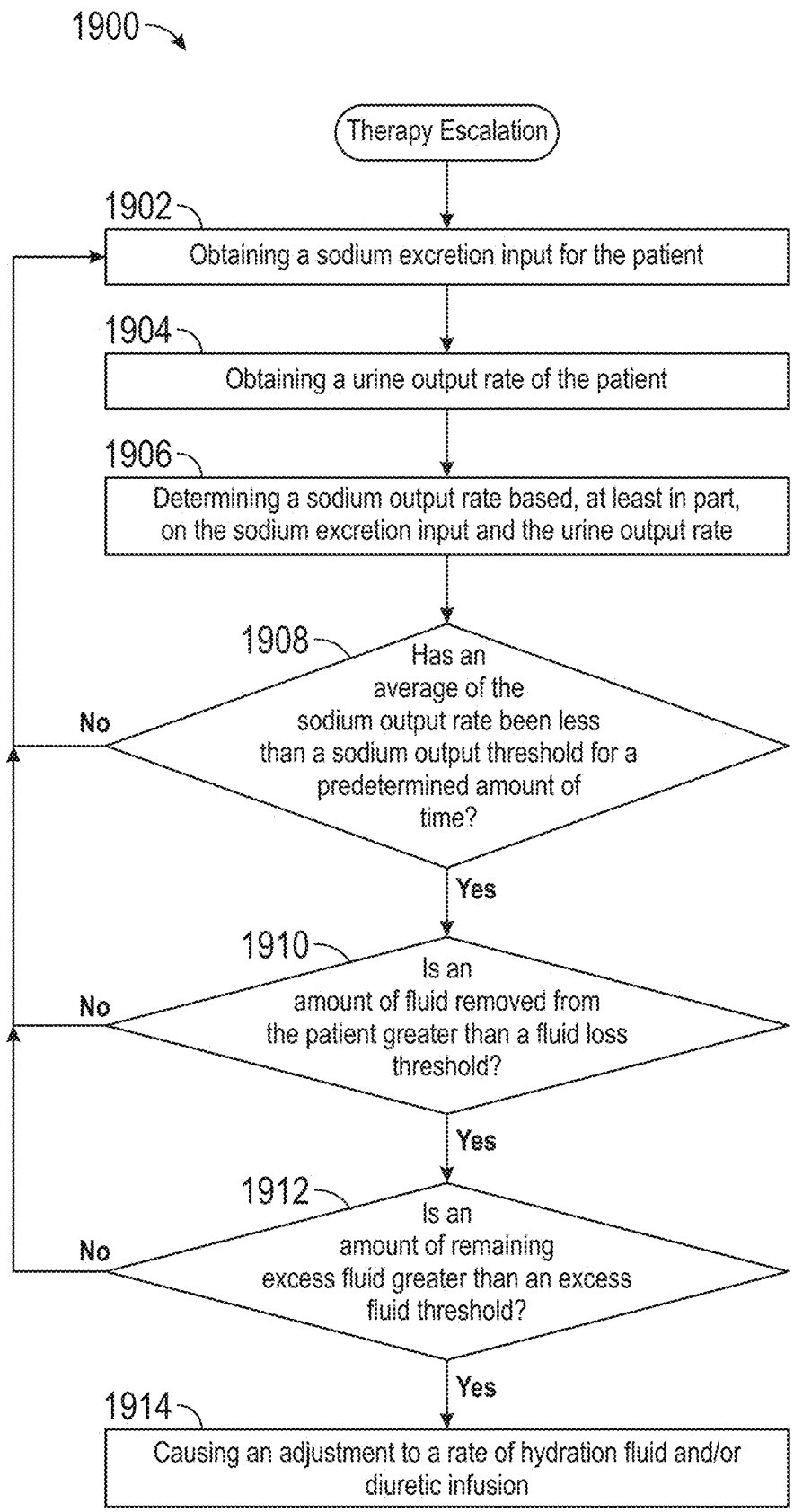
FIG. 19 is a flow diagram of a method for initiating a therapy escalation based at least in part on a patient's sodium output rate, in accordance with embodiments of the present technology.

FIG. 19 is a flow diagram of a method 1900 for initiating a therapy escalation based at least in part on a patient's sodium output rate, in accordance with embodiments of the present technology. The method 1900 can be performed by the embodiments of the systems and devices described herein, such as the system 100 of FIG. 1. In some embodiments, some or all of the blocks of the method 1900 are performed by a system or device including one or more processors and a memory storing instructions that, when executed by the one or more processors, cause the system or device to perform one or more of the blocks described herein. For example, the method 1900 can be performed by the controller 140 of the system 100 of FIG. 1 and/or another suitable processor. Optionally, some or all of the blocks of the method 1900 can performed automatically or semi-automatically, with little or no human intervention.

The method 1900 can begin at block 1902 with obtaining a sodium excretion input for the patient. Block 1902 can be at least generally similar or identical to block 502 of the method 500, described with reference to FIG. 5.

At block 1904, the method 1900 can include obtaining a urine output rate of the patient. Block 1904 can be at least generally similar or identical to block 202 of the method 200, described with reference to FIG. 2.

At block 1906, the method 1900 can include determining a sodium output rate for the patient based, at least in part, on the obtained sodium excretion input (block 1902) and the urine output rate (block 1904). Block 1906 can be at least generally similar or identical to block 1606 of the method 1600, described with reference to FIG. 16.

At block 1908, the method 1900 can include determining whether an average of the sodium output rate has been less than a sodium output rate threshold for a predetermined amount of time. Block 1908 can be at least generally similar or identical to block 1808 of the method 1800, described with reference to FIG. 18. If the average of the sodium output rate has been less than the sodium output rate threshold for the predetermined amount of time (block 1908, YES), the method 1900 can continue to block 1910. If not (block 1908, NO), the method 1900 can end and/or return to block 1902 and/or repeat one or more of blocks 1902-1908.

At block 1910, the method 1900 can include determining whether an amount of fluid removed from the patient is greater than a fluid loss threshold. The fluid loss threshold can be a percentage of an amount of estimated excess fluid to be removed from the patient and/or another fluid loss goal associated with the patient's fluid therapy. The percentage can be up to 30%, 40%, 50%, 60%, 70%, 80%, or 90%. In at least some embodiments, for example, the method 1900 includes determining whether the amount of fluid removed from the patient is greater than 80% of the amount of estimated excess fluid to be removed from the patient. If the amount of fluid removed from the patient is greater than the fluid loss threshold (block 1910, YES), the method 1900 can continue to block 1912. If not (block 1912, NO), the method 1900 can end and/or return to block 1902 and/or repeat one or more of blocks 1902-1910. Additionally or alternatively to using the volume of urine from the patient, in some embodiments a volume of sodium removed from the patient can be utilized.

At block 1912, the method 1900 can include determining whether an amount of remaining excess fluid within the patient is greater than an excess fluid threshold. The excess fluid threshold can be an amount of fluid (e.g., up to 500 mL, 750 mL, 1 L, 1.5 L, or 2 L) still to be removed from the patient. If the amount of remaining excess fluid is greater than the excess fluid threshold (block 1912, YES), the method can continue to block 1914. If not (block 1912, NO), the method 1900 can end and/or return to block 1902 and/or repeat one or more of blocks 1902-1212.

At block 1914, the method 1900 can include causing an adjustment to a rate of hydration fluid and/or diuretic infusion. In some embodiments, block 1914 includes causing a second or additional diuretic (e.g., thiazide, additional loop diuretic, or both) to be administered to the patient and/or temporarily increasing the hydration fluid infusion rate to, e.g., temporarily increase the matched amount of urine output. In these and/or other embodiments, block 1914 can include increasing or decreasing the rate of hydration fluid and/or diuretic infusion to promote fluid loss (e.g., increased fluid loss) from the patient. In some embodiments, the method 1900 includes causing the adjustment if (e.g., only if) the patient is receiving a maximum dose of diuretic.

Figure 20:
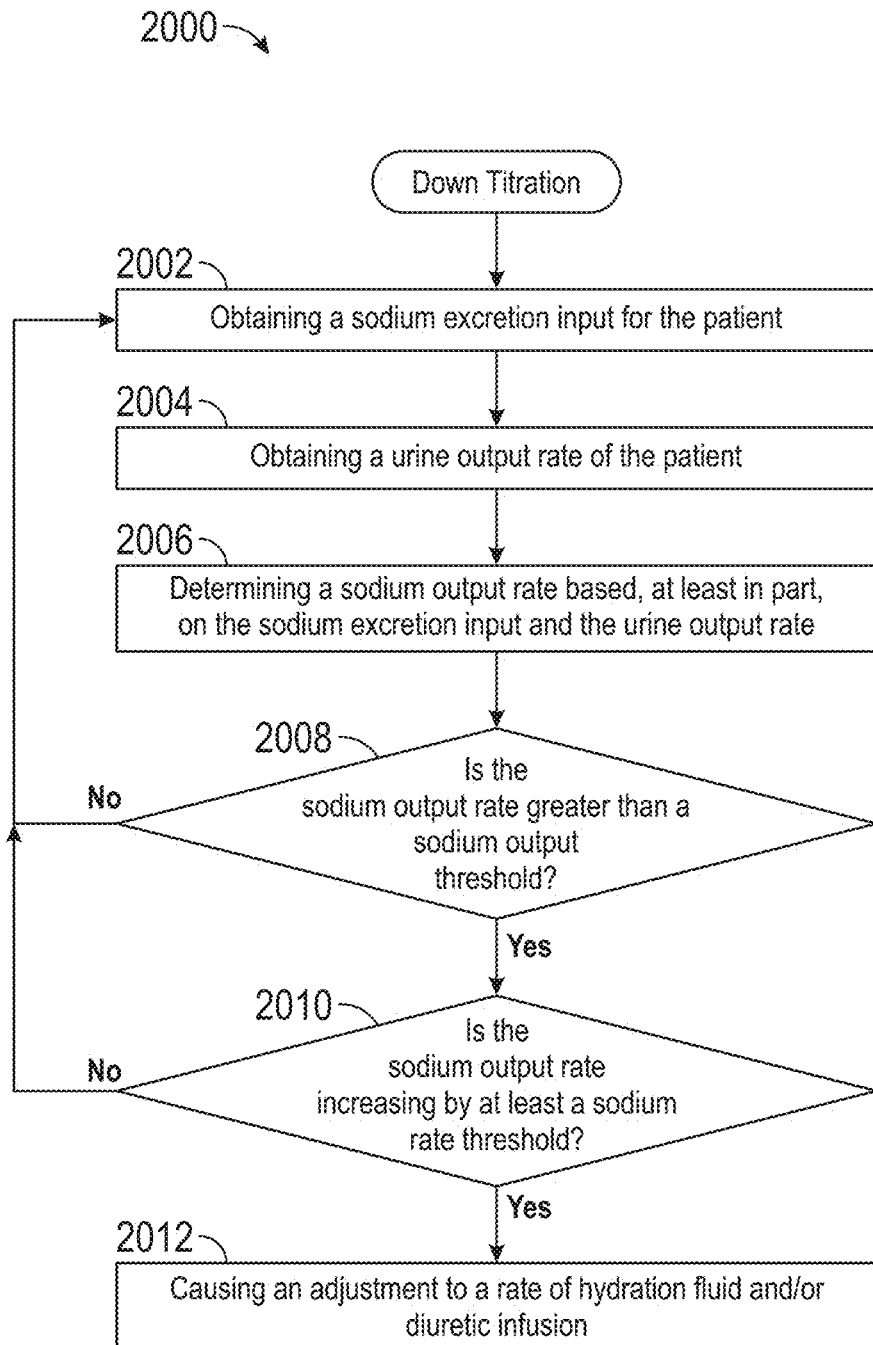
FIG. 20 is a flow diagram of a method for initiating a down titration based at least in part on a patient's sodium output rate, in accordance with embodiments of the present technology.

FIG. 20 is a flow diagram of a method 2000 for initiating a down titration based at least in part on a patient's sodium output rate, in accordance with embodiments of the present technology. The method 2000 can be performed by the embodiments of the systems and devices described herein, such as the system 100 of FIG. 1. In some embodiments, some or all of the blocks of the method 2000 are performed by a system or device including one or more processors and a memory storing instructions that, when executed by the one or more processors, cause the system or device to perform one or more of the blocks described herein. For example, the method 2000 can be performed by the controller 140 of the system 100 of FIG. 1 and/or another suitable processor. Optionally, some or all of the blocks of the method 2000 can performed automatically or semi-automatically, with little or no human intervention.

The method 2000 can begin at block 2002 with obtaining a sodium excretion input for the patient. Block 2002 can be at least generally similar or identical to block 502 of the method 500, described with reference to FIG. 5.

At block 2004, the method 2000 can include obtaining a urine output rate of the patient. Block 2004 can be at least generally similar or identical to block 202 of the method 200, described with reference to FIG. 2.

At block 2006, the method 2000 can include determining a sodium output rate for the patient based, at least in part, on the obtained sodium excretion input (block 2002) and the urine output rate (block 2004). Block 2006 can be at least generally similar or identical to block 1606 of the method 1600, described with reference to FIG. 16.

At block 2008, the method 2000 can include determining whether the sodium output rate (block 2006) is greater than a sodium output threshold. The sodium output threshold can be a rate of sodium output that, for a given urine sodium concentration, is equivalent to a urine output rate of at least or up to 975 ml/hr, 1025 ml/hr, 1075 ml/hr, 1125 ml/hr, 1175 ml/hr, 1225 ml/hr, 1275 ml/hr, 1325 ml/hr, 1375 ml/hr, 1425 ml/hr, 1475 ml/hr, 1525 ml/hr, 1575 ml/hr, 1625 ml/hr, 1675 ml/hr, 1725 ml/hr, 1775 ml/hr, 1825 ml/hr, 1875 ml/hr, 1925 ml/hr, 1975 ml/hr, 2025 ml/hr, 2075 ml/hr, or within a range of 975-2075 ml/hr, for a given urine sodium concentration. For example, the sodium output threshold can be a rate of 143.5 mmol/hr, which is equivalent to a urine output rate 1025 ml/hr with a urine sodium concentration of 140 mmol/L. If the sodium output rate is greater than the sodium output threshold (block 2008, YES), the method 2000 can continue to block 2010. If not (block 2008, NO), the method 200 can end and/or return to block 2002 and/or repeat one or more of blocks 2002-2008.

At block 2010, the method 2000 can include determining whether the sodium output rate is increasing by at least a sodium rate threshold. The sodium rate threshold can be an increase to the sodium output rate that, for a given urine sodium concentration, is equivalent to an increase in the urine output rate up to a 30 ml/hr$^2$, 40 ml/hr$^2$, 50 ml/hr$^2$, 60 ml/hr$^2$, 70 ml/hr$^2$, or within a range of 30-70 ml/hr$^2$, for a given urine sodium concentration. For example, the sodium output rate can be 7 mmol/hr$^2$, which is equivalent to an increase of 50 ml/hr$^2$ in the urine output rate at a urine sodium concentration of 140 mmol/L. If the sodium output rate is increasing by at least the sodium rate threshold (block 2010, YES), the method 2000 can continue to block 2012. If not (block 2010, NO), the method 2000 can end and/or return to block 2002 and/or repeat one or more of blocks 2002-2010.

At block 2012, the method 2000 can include causing an adjustment to a rate of hydration fluid and/or diuretic infusion. In at least some embodiments, block 2012 includes decreasing or otherwise down titrating the diuretic dosage rate, as described previously herein with reference to at least block 208 of the method 200.

Figure 21:
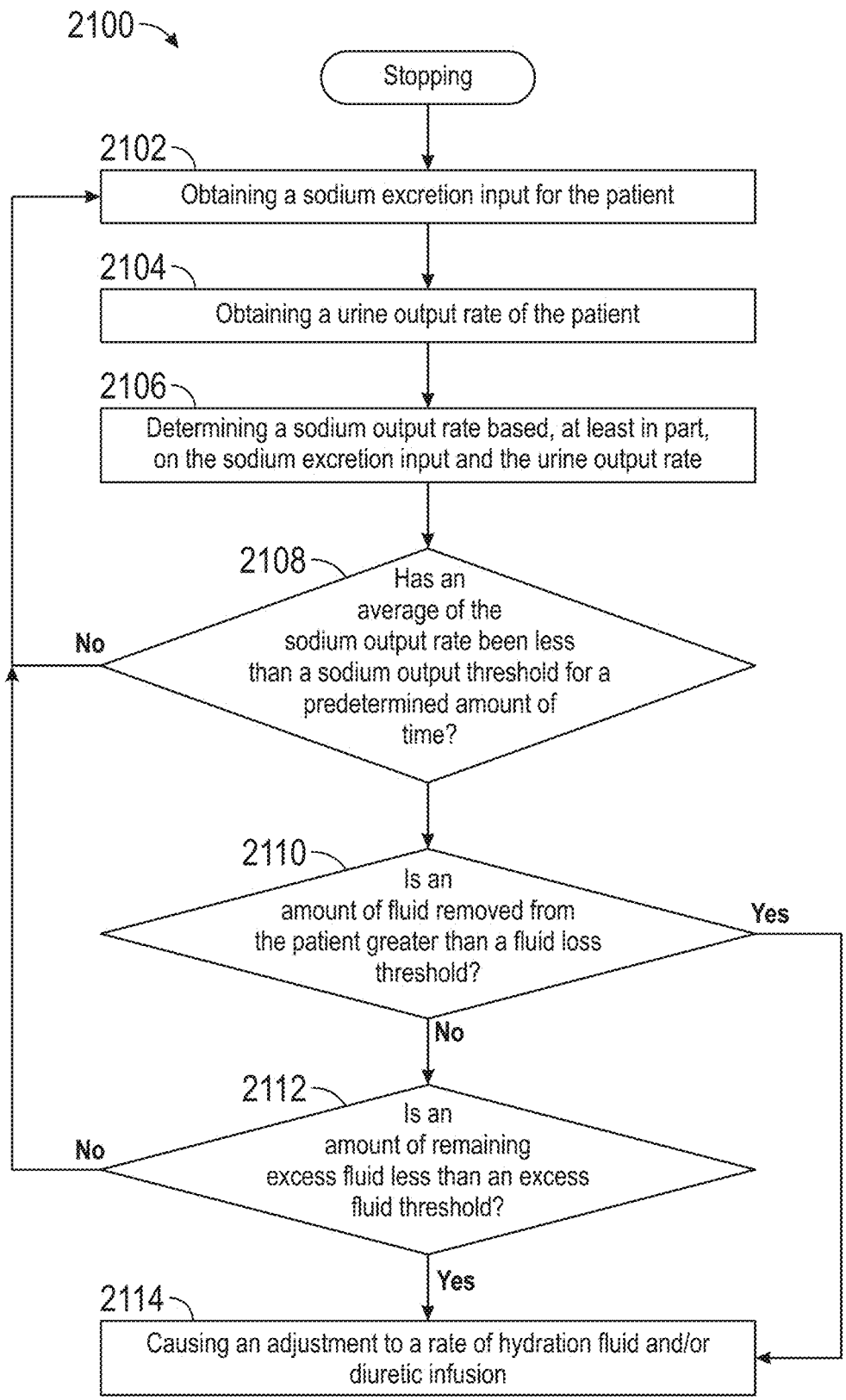
FIG. 21 is a flow diagram of a method for stopping fluid therapy based on a patient's sodium output rate, in accordance with embodiments of the present technology.

FIG. 21 is a flow diagram of a method 2100 for stopping fluid therapy based on a patient's sodium output rate, in accordance with embodiments of the present technology. The method 2100 can be performed by the embodiments of the systems and devices described herein, such as the system 100 of FIG. 1. In some embodiments, some or all of the blocks of the method 2100 are performed by a system or device including one or more processors and a memory storing instructions that, when executed by the one or more processors, cause the system or device to perform one or more of the blocks described herein. For example, the method 2100 can be performed by the controller 140 of the system 100 of FIG. 1 and/or another suitable processor. Optionally, some or all of the blocks of the method 2100 can performed automatically or semi-automatically, with little or no human intervention.

The method 2100 can begin at block 2102 with obtaining a sodium excretion input for the patient. Block 2102 can be at least generally similar or identical to block 502 of the method 500, described with reference to FIG. 5.

At block 2104, the method 2100 can include obtaining a urine output rate of the patient. Block 2104 can be at least generally similar or identical to block 202 of the method 200, described with reference to FIG. 2.

At block 2106, the method 2100 can include determining a sodium output rate for the patient based, at least in part, on the obtained sodium excretion input (block 2102) and the urine output rate (block 2104). Block 2106 can be at least generally similar or identical to block 1606 of the method 1600, described with reference to FIG. 16.

At block 2108, the method 2100 can include determining whether an average of the sodium output rate has been less than a sodium output rate threshold for a predetermined amount of time. Block 2108 can be at least generally similar or identical to block 1808 of the method 1800, described with reference to FIG. 18. If the average of the sodium output rate has been less than the sodium output rate threshold for the predetermined amount of time (block 2108, YES), the method 2100 can continue to block 2110. If not (block 2108, NO), the method 2100 can end and/or return to block 2102 and/or repeat one or more of blocks 2102-2108.

At block 2110, the method 2100 can include determining whether an amount of fluid removed from the patient is greater than a fluid loss threshold. Block 2110 can be at least generally similar to block 1910 of the method 1900, described with reference to FIG. 19. If the amount of fluid removed from the patient is greater than the fluid loss threshold (block 2110, YES), the method 2100 can continue to block 2112. If not (block 2112, NO), the method 2100 can end and/or return to block 2102 and/or repeat one or more of blocks 2102-2110.

At block 2112, the method 2100 can include determining whether an amount of remaining excess fluid within the patient is less than an excess fluid threshold. The excess fluid threshold can be at least generally similar or identical to the excess fluid threshold escribes previously with reference to block 1912 of the method 1900. If the amount of remaining excess fluid is less than the excess fluid threshold (block 2112, YES), the method can continue to block 1914. If not (block 2112, NO), the method 2100 can end and/or return to block 2102 and/or repeat one or more of blocks 2102-2112.

At block 2114, the method 2100 can include causing an adjustment to a rate of hydration fluid and/or diuretic infusion. In some embodiments, the adjustment can include stopping the administration of the hydration fluid and/or the diuretic. In some embodiments, causing the adjustment includes recommending the adjustment and, in response to a user input, stopping the administration of the hydration fluid and/or the diuretic.

V. EXPERIMENTAL RESULTS

The following discussion and associated figures include data obtained from patients that received fluid therapy in accordance with embodiments of the present technology. These materials are included to further describe some aspects of the present technology and should not be used to limit the scope of the invention.

As described previously herein, sodium naturally causes the body to retain water and, as such, one goal of fluid therapy is to reduce a patient's overall fluid balance by removing sodium via urine. During fluid therapy, a patient often receives hydration fluid, which includes sodium, in an amount that is based at least partially on the patient's urine output in order to prevent dehydration, hyponatremia, and/or other negative conditions. However, infusing excessive amounts of hydration fluid—and thus excessive amounts of sodium—can prevent or inhibit optimal therapy by causing sodium to be removed at sub-optimal rates and, in some instances, may even cause harm to the patient (by, e.g., inducing hypernatremia and/or other negative sequelae).

Figure 22A:
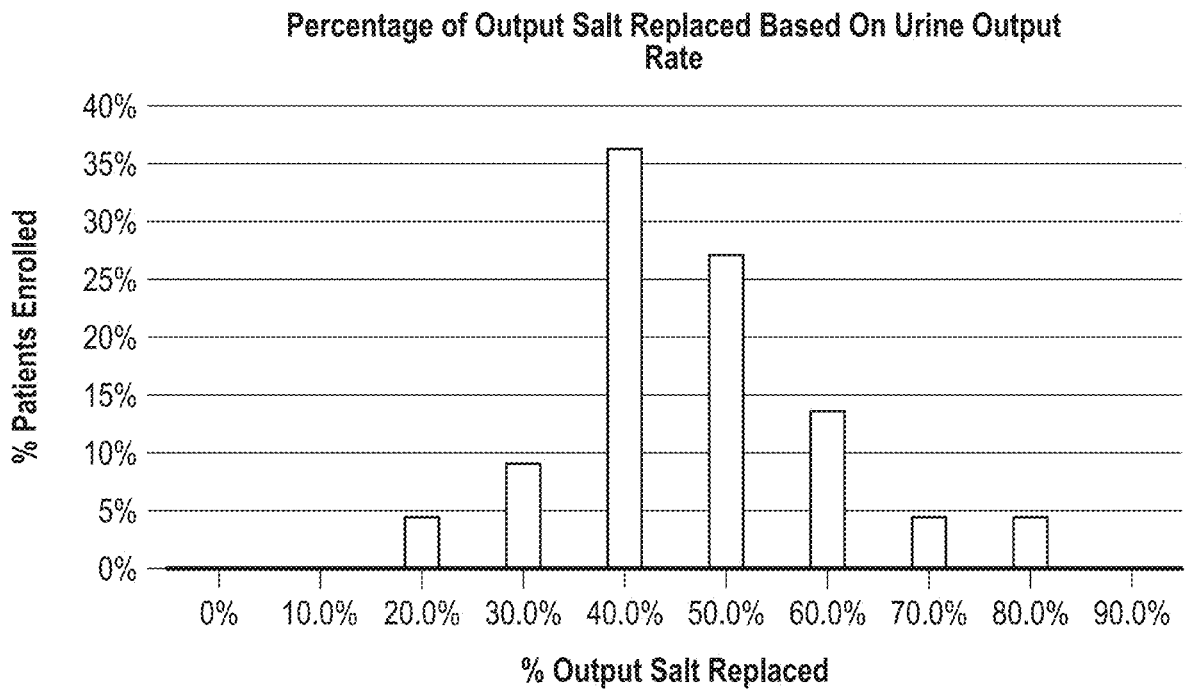
FIG. 22A is a chart of patient data showing the percentage of excreted sodium that was replaced during fluid therapy based on urine output rate.
Figure 22B:
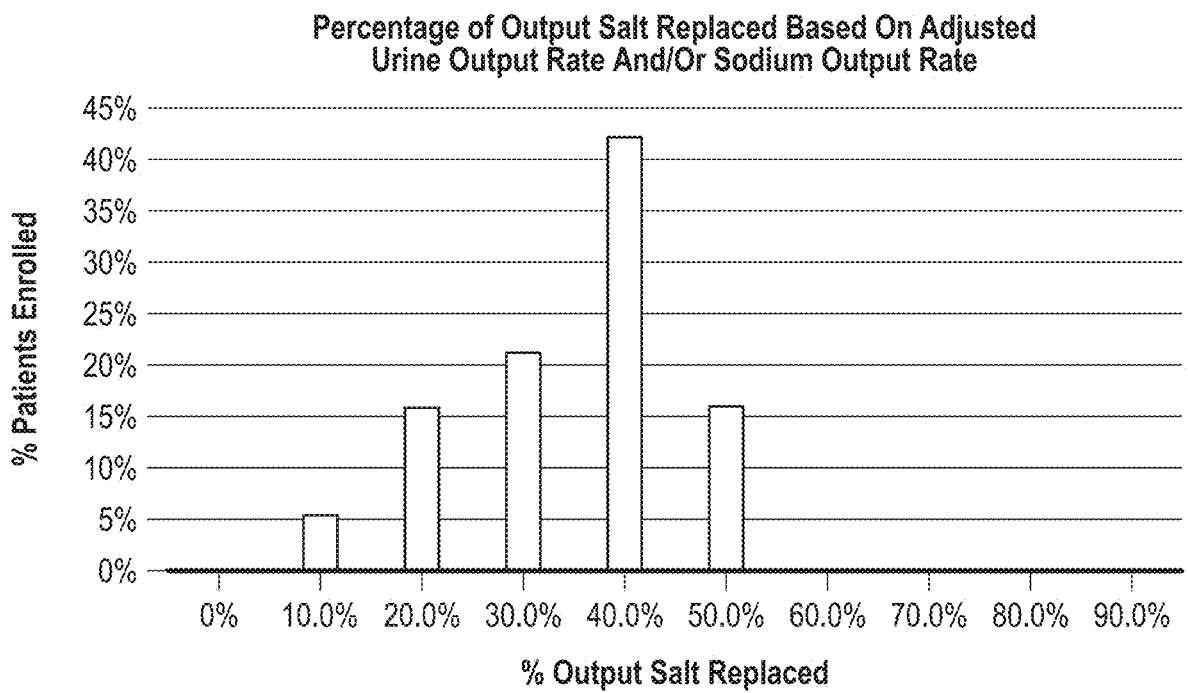
FIG. 22B is a chart of patient data showing the percentage of excreted sodium that was replaced during fluid therapy based on adjusted urine output rate and/or sodium output rate, in accordance with embodiments of the present technology.

FIG. 22A is a chart of patient data showing the percentage of output salt (e.g., excreted sodium) that was replaced during fluid therapy based on urine output rate, and FIG. 22B is a chart of patient data showing the percentage of output salt that was replaced during fluid therapy based on adjusted urine output rate and/or sodium output rate, in accordance with embodiments of the present technology. As shown in FIG. 22A, the majority of patients that received fluid therapy based on their urine output rate were administered sodium via a hydration fluid (e.g., saline) in an amount that was equal to or greater than 50% of their sodium output. Moreover, more than 20% of the patients enrolled had more than 60% of the output salt replaced. In comparison, as shown in FIG. 22B, the majority of patients that received fluid therapy based on their adjusted urine output rate and/or sodium output rate were administered sodium in an amount that was less than or equal to 40% of their sodium output, and no patients received more than 60% of their sodium output. Thus, patients that received fluid therapy based on their adjusted urine output rate and/or sodium output rate received, on average, had a reduced amount of sodium replaced compared to patients that received fluid therapy based on their (unadjusted) urine output rate. For example, in FIG. 22B only approximately 16% of patients received an amount of sodium equivalent to 50% of the sodium output, whereas in FIG. 22A approximately 26% of patients received that amount of sodium and approximately 24% of patients received an amount of sodium greater than 50% of their sodium output. As such, the patients that received fluid therapy based on their adjusted urine output rate and/or sodium output rate are expected to, on average, receive less sodium over the course of fluid therapy and, as a result, have increased sodium output, lower serum sodium levels, and/or increased net fluid loss compared to the patients that received fluid therapy based on their (unadjusted) urine output rate.

Figure 23A:
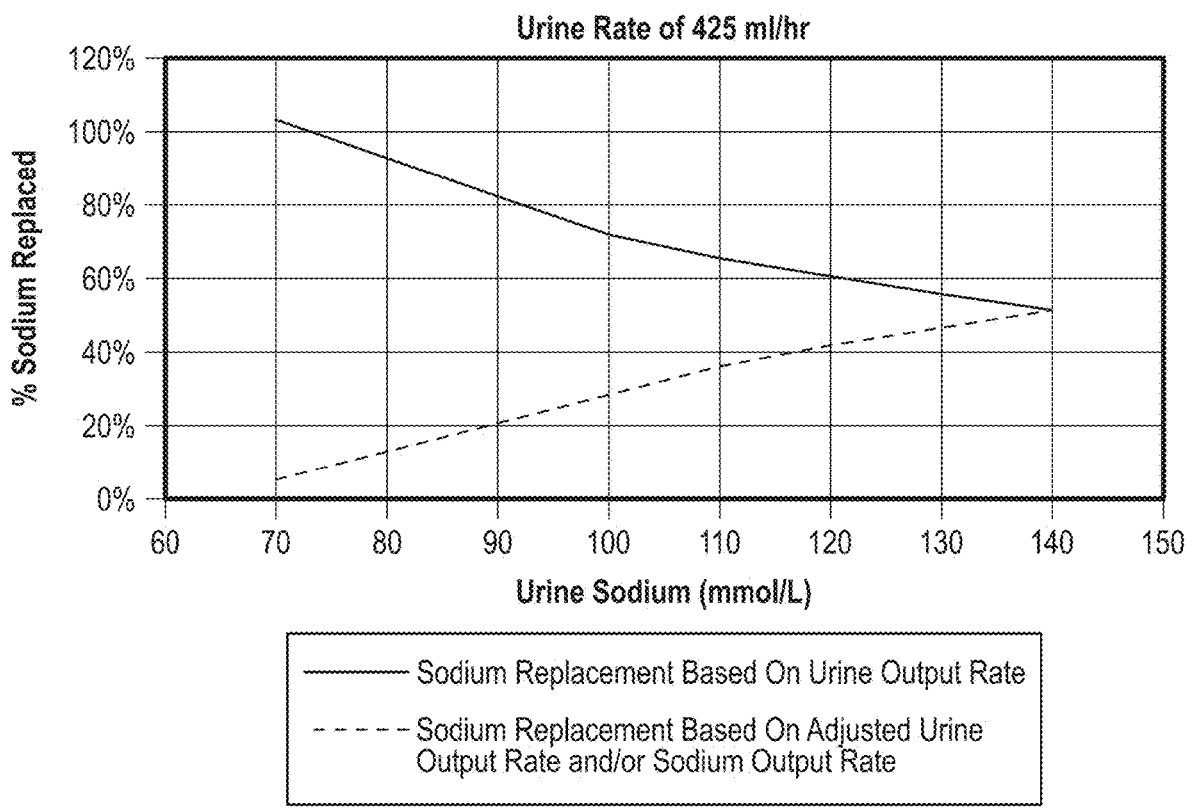
FIGS. 23A and 23B are plots comparing sodium replacement based on urine output rate with sodium replacement based on adjusted urine output rate and/or sodium output rate in accordance with embodiments of the present technology.
Figure 23B:
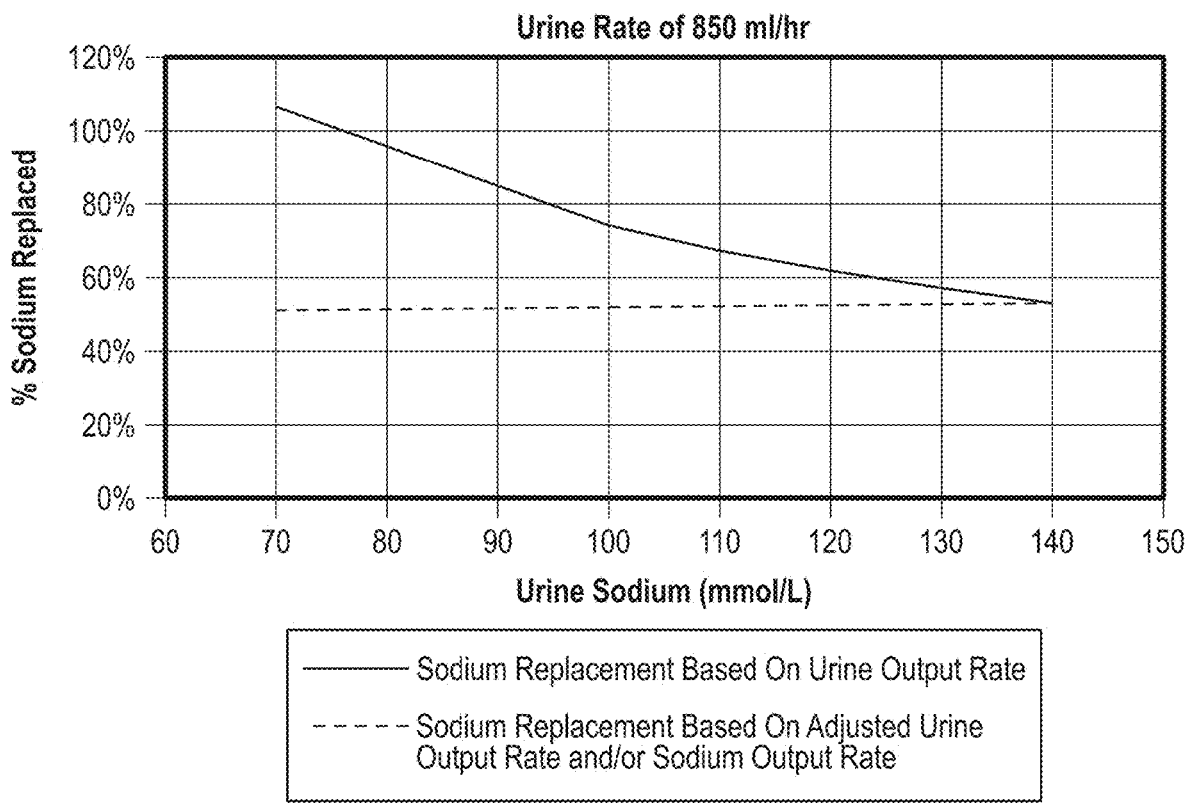

FIGS. 23A and 23B are plots comparing sodium replacement based on urine output rate with sodium replacement based on adjusted urine output rate and/or sodium output rate for different urine output rates. FIG. 23A shows sodium replacement for different urine sodium concentrations based on a urine output rate of 425 mL/hr which, as described herein with reference to at least FIG. 15, can be a urine output rate at or about which hydration fluid infusion begins. FIG. 23B shows sodium replacement for different urine sodium concentrations based on a urine output rate of 850 mL/hr which, as described herein with reference to at least FIGS. 13 and 15, can be a urine output rate at or about which the patient's diuretic dosage rates can be down-titrated. As shown in FIGS. 23A and 23B, at each of these urine output rates, the percent sodium replacement determined based at least in part on a patient's adjusted urine output rate and/or a sodium output rate is consistently less than or equal to the percent sodium replacement determined based at least in part on the patient's (unadjusted) urine output rate.

Figure 24A:
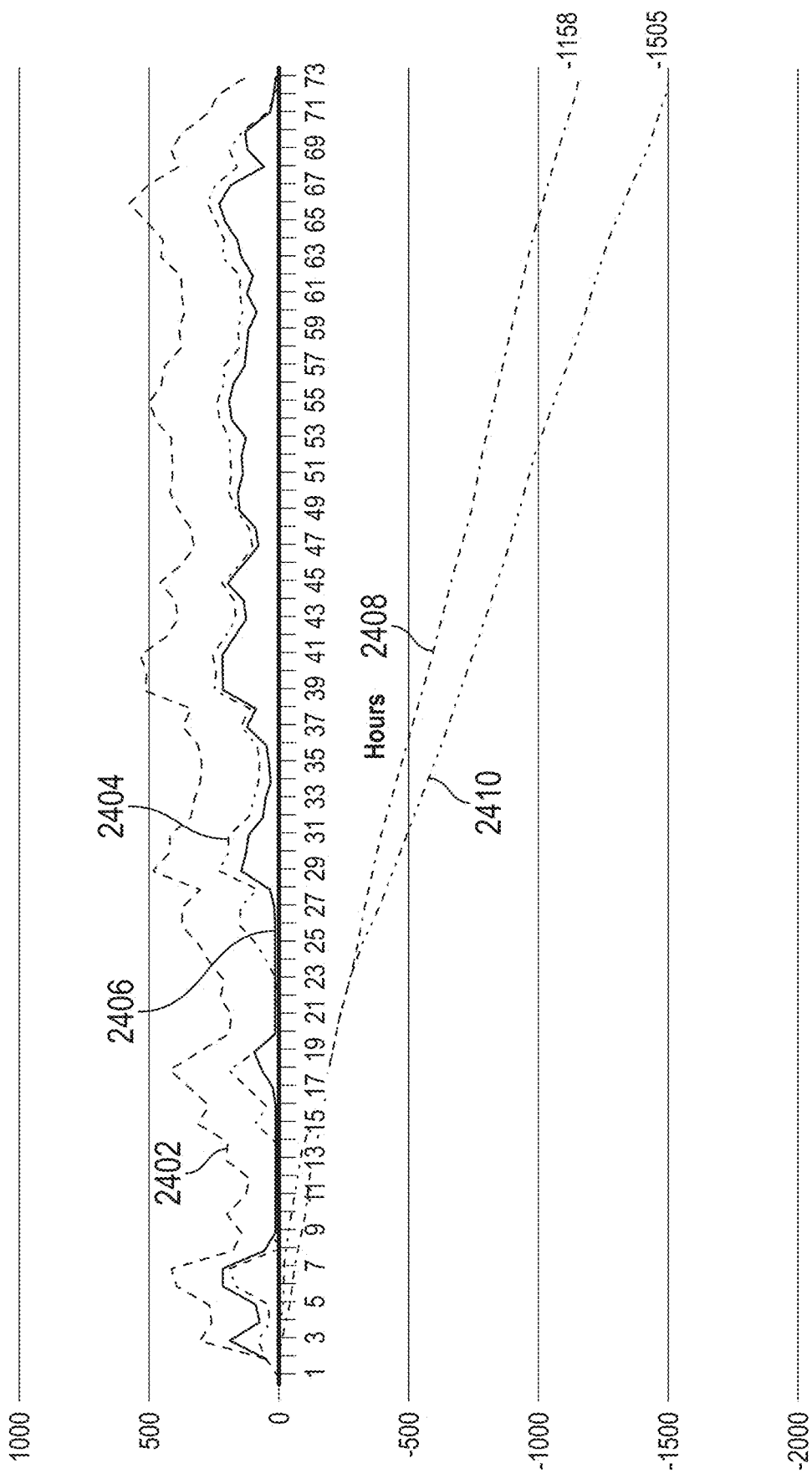
FIGS. 24A-26B are plots of data from patients that received fluid therapy in accordance with embodiments of the present technology.

FIG. 24A is a plot of example fluid therapy data for a patient with an average urine sodium concentration of 101 mmol/L (e.g., 39 mmol/L lower than an expected 140 mmol/L concentration). These data include hourly urine output 2402 (in mL), a first hydration fluid infusion rate 2404 (in mL/hr) based on (unadjusted) urine output rate, a second hydration fluid infusion rate 2406 (in mL/hr) based on an adjusted urine output rate and/or sodium output rate, a first cumulative net sodium loss 2408 (in mmol) associated with the first hydration fluid infusion rate 2404, and a second cumulative net sodium loss 2410 (in mmol) associated with the second hydration fluid infusion rate 2406. Both the first and second hydration fluid infusion rates 2404, 2406 generally track the patient's hourly urine output 2402 but, except for the first several hours of the depicted fluid therapy, the second hydration fluid infusion rate 2406 remained less than or approximately equal to the first hydration fluid infusion rate 2404. At the end of the fluid therapy, the second cumulative net sodium loss 2410 was greater than the first cumulative net sodium loss 2408, meaning that the second hydration fluid infusion rate 2406 caused a greater net sodium loss, as well as a greater net fluid loss, than the first hydration fluid infusion rate 2408.

Figure 24B:
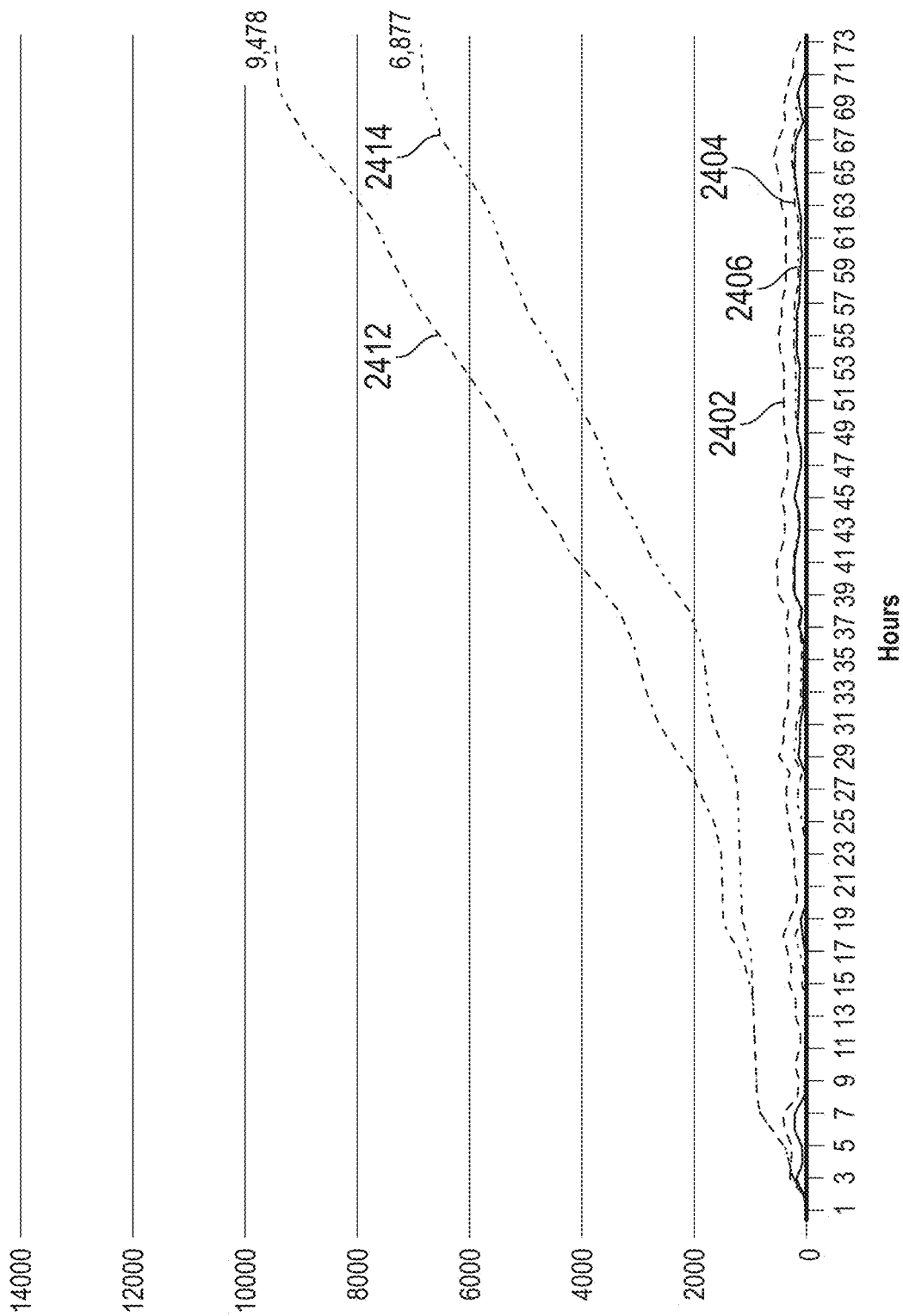

FIG. 24B is a plot of additional example fluid therapy data for the patient in FIG. 24A. In addition to showing the hourly urine output 2402 (in mL), the first hydration fluid infusion rate 2404 (in mL/hr), and the second hydration fluid infusion rate 2406 from FIG. 24A, FIG. 24B also includes a plot of first total saline infusion 2412 (in ml) based on the patient's (unadjusted) urine output rate and a plot of second total saline infusion 2414 (in ml) based on the patient's adjusted urine output rate and/or sodium output rate. As shown in FIG. 24B, at the end of treatment the second total saline infusion 2414 was less than the first total saline infusion 2412, meaning that providing fluid therapy based on the patient's adjusted urine output rate and/or sodium output rate led to less saline being infused over the course of fluid therapy than providing fluid therapy based on the patient's (unadjusted) urine output rate.

Figure 25A:
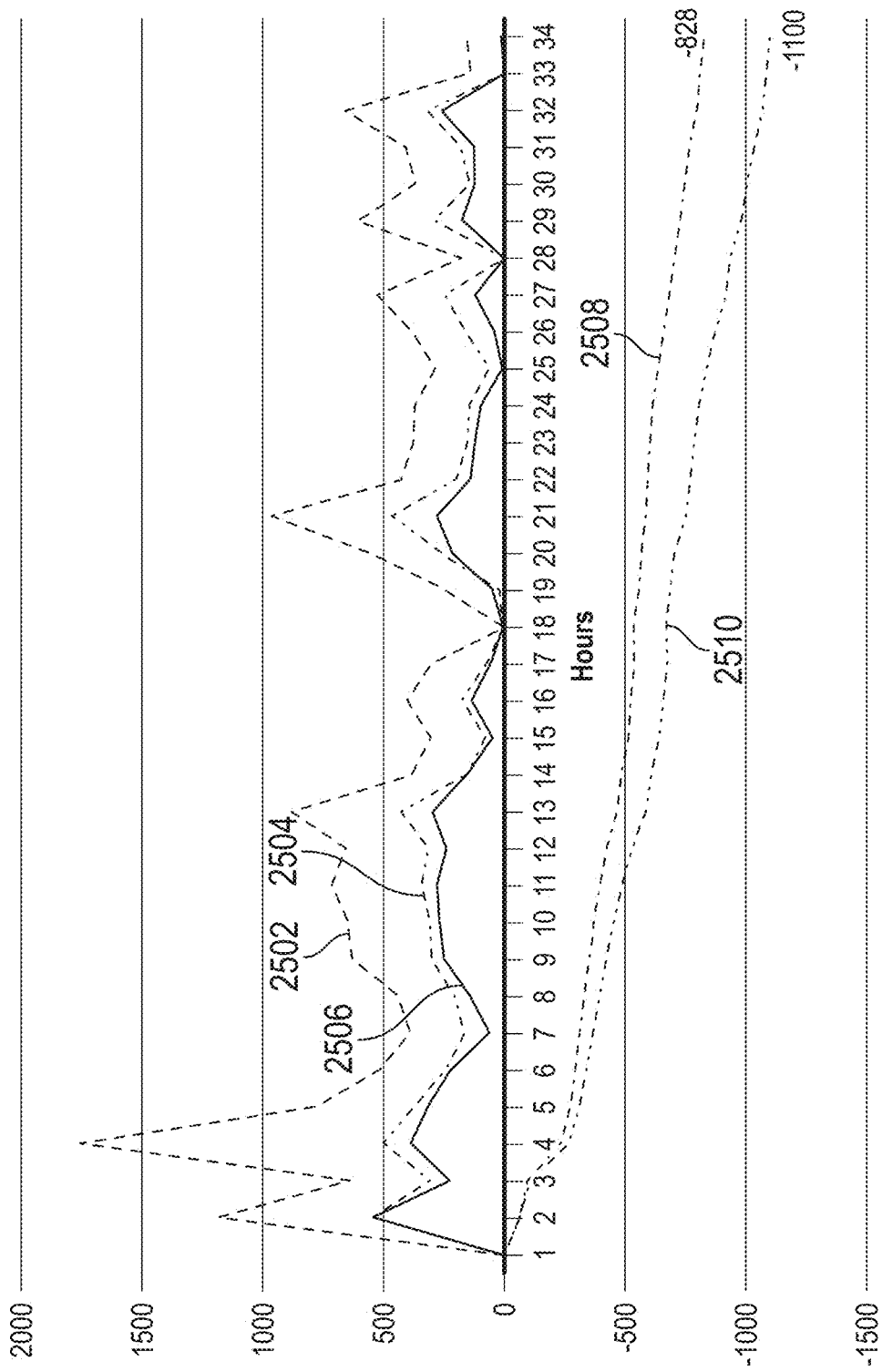

FIG. 25A is a plot of example fluid therapy data for a patient with an average urine sodium concentration of 110 mmol/L (e.g., 30 mmol/L lower than an expected 140 mmol/L urine sodium concentration). These data include hourly urine output 2502 (in mL), a first hydration fluid infusion rate 2504 (in mL/hr) based on (unadjusted) urine output rate, a second hydration fluid infusion rate 2506 (in mL/hr) based on an adjusted urine output rate and/or sodium output rate, a first cumulative net sodium loss 2508 (in mmol) associated with the first hydration fluid infusion rate 2504, and a second cumulative net sodium loss 2510 (in mmol) associated with the second hydration fluid infusion rate 2506. Both the first and second hydration fluid infusion rates 2504, 2506 generally track the patient's hourly urine output 2502 and the second hydration fluid infusion rate 2506 generally remained less than or approximately equal to the first hydration fluid infusion rate 2504 throughout treatment. At the end of the fluid therapy, the second cumulative net sodium loss 2510 was greater than the first cumulative net sodium loss 2508, meaning that the second hydration fluid infusion rate 2506 caused a greater net sodium loss (and, e.g., a greater net fluid loss) than the first hydration fluid infusion rate 2508.

Figure 25B:
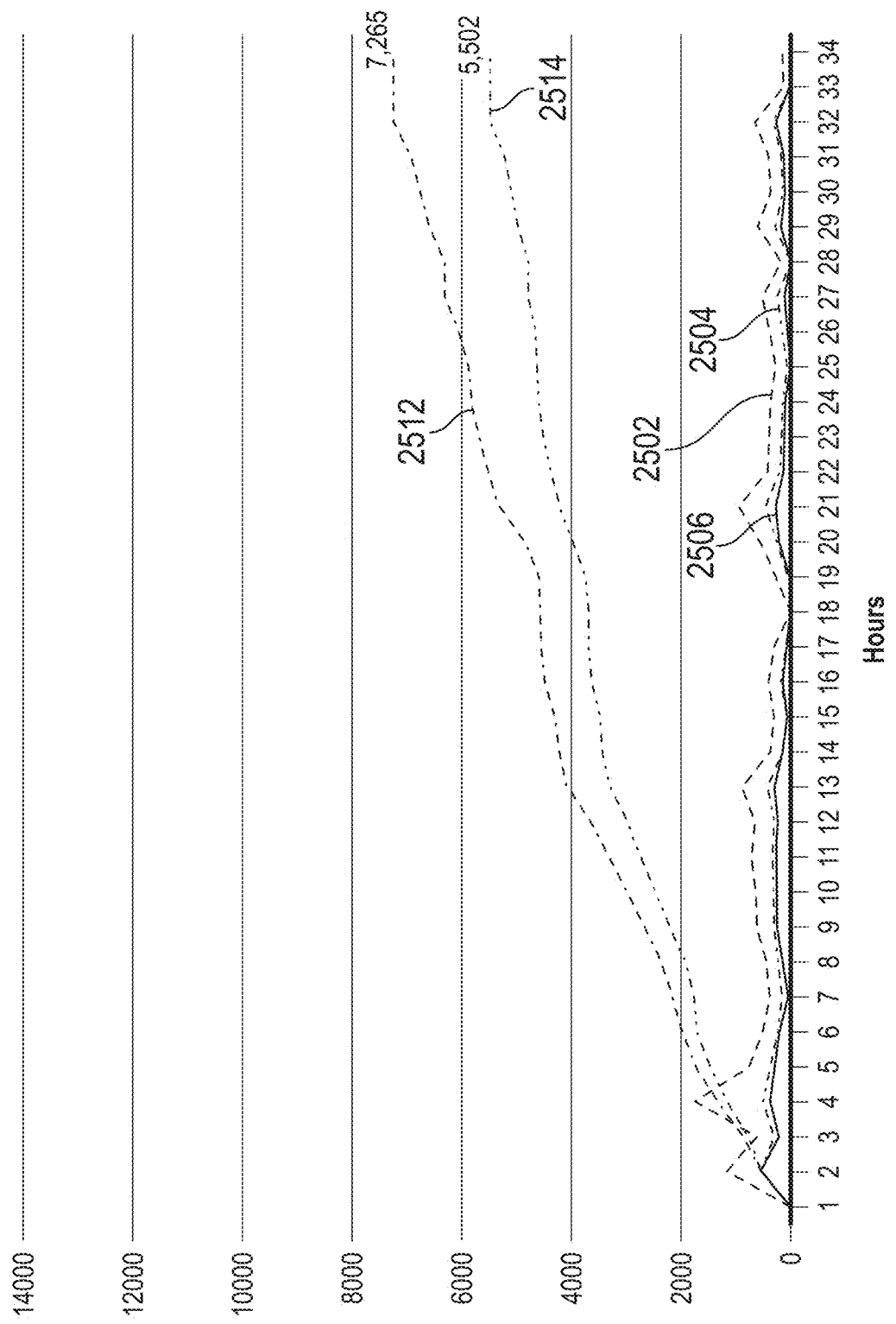

FIG. 25B is a plot of additional example fluid therapy data for the patient in FIG. 25A. In addition to showing the hourly urine output 2502 (in mL), the first hydration fluid infusion rate 2504 (in mL/hr), and the second hydration fluid infusion rate 2506 from FIG. 25A, FIG. 25B also includes a plot of first total saline infusion 2512 (in ml) based on the patient's (unadjusted) urine output rate and a plot of second total saline infusion 2514 (in ml) based on the patient's adjusted urine output rate and/or sodium output rate. As shown in FIG. 25B, at the end of treatment the second total saline infusion 2514 was less than the first total saline infusion 2512, meaning that providing fluid therapy based on the patient's adjusted urine output rate and/or sodium output rate led to less saline being infused over the course of fluid therapy than providing fluid therapy based on the patient's (unadjusted) urine output rate.

Figure 26A:
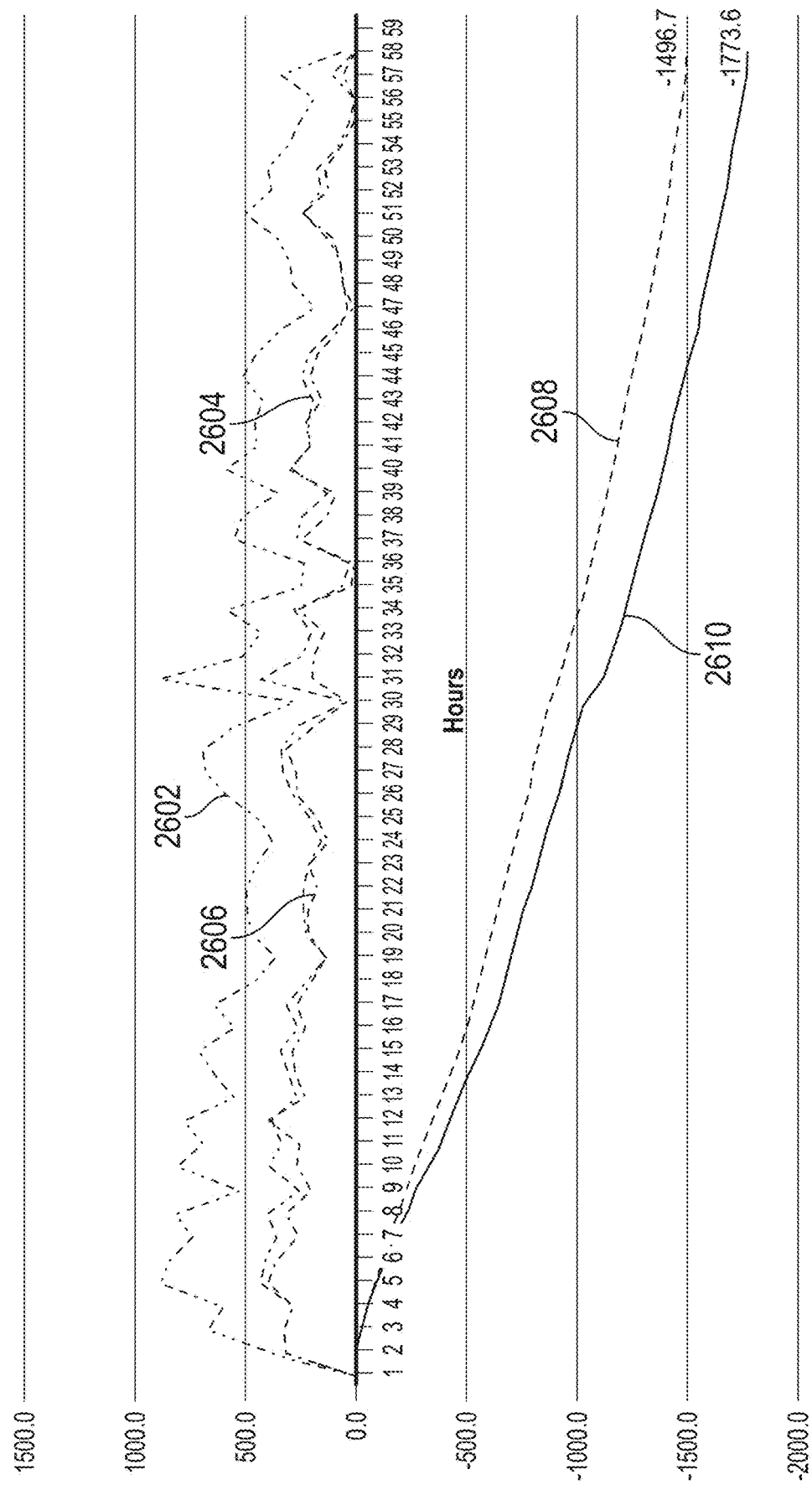

FIG. 26A is a plot of example fluid therapy data for a patient with an average urine sodium concentration of 120 mmol/L (e.g., 20 mmol/L lower than an expected 140 mmol/L urine sodium concentration). These data include hourly urine output 2602 (in mL), a first hydration fluid infusion rate 2604 (in mL/hr) based on (unadjusted) urine output rate, a second hydration fluid infusion rate 2606 (in mL/hr) based on an adjusted urine output rate and/or sodium output rate, a first cumulative net sodium loss 2608 (in mmol) associated with the first hydration fluid infusion rate 2604, and a second cumulative net sodium loss 2610 (in mmol) associated with the second hydration fluid infusion rate 2606. Both the first and second hydration fluid infusion rates 2604, 2606 generally track the patient's hourly urine output 2602 and the second hydration fluid infusion rate 2606 generally remained less than or approximately equal to the first hydration fluid infusion rate 2604 throughout treatment. At the end of the fluid therapy, the second cumulative net sodium loss 2610 was greater than the first cumulative net sodium loss 2608, meaning that the second hydration fluid infusion rate 2606 caused a greater net sodium loss (and, e.g., a greater net fluid loss) than the first hydration fluid infusion rate 2608.

Figure 26B:
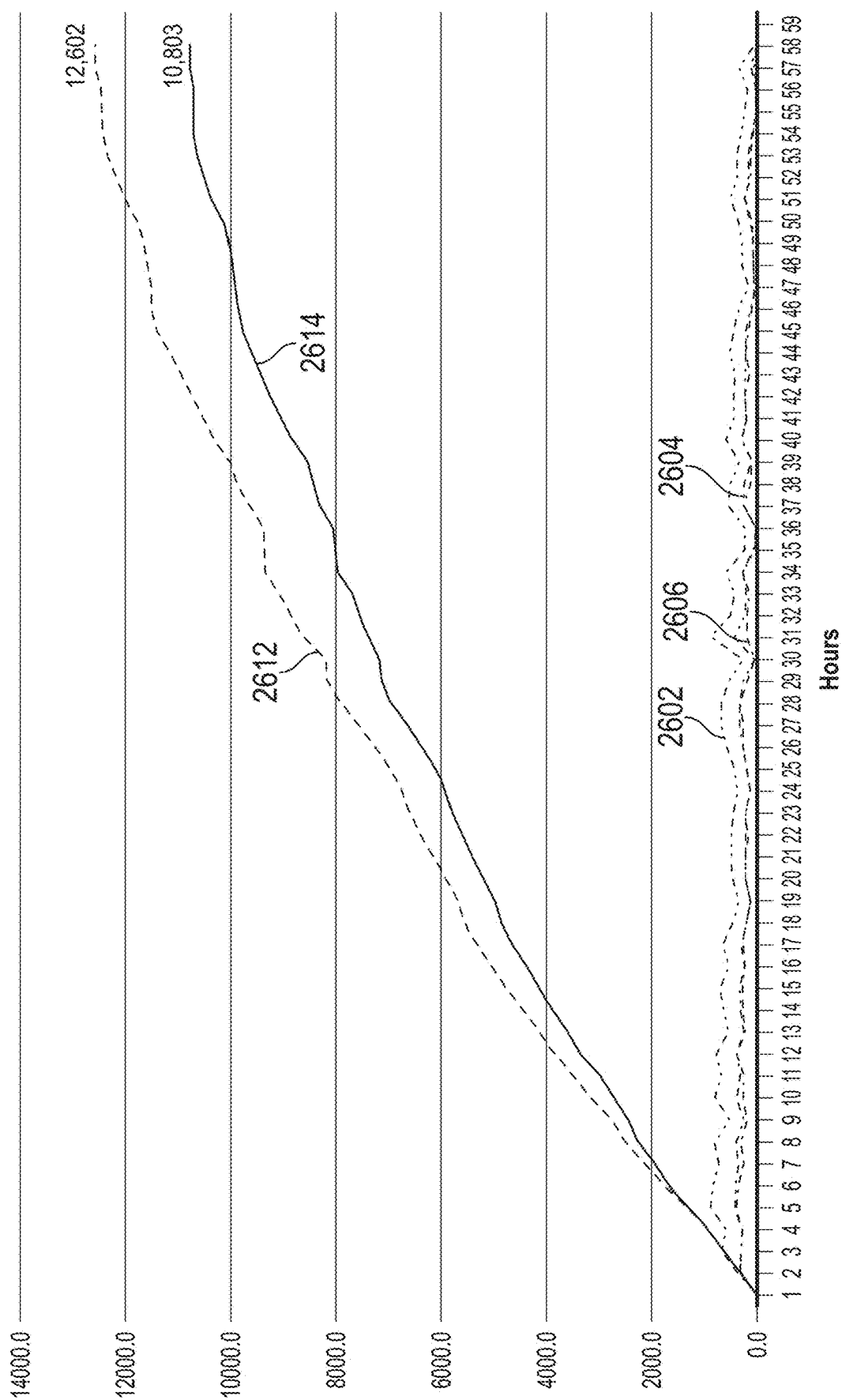

FIG. 26B is a plot of additional example fluid therapy data for the patient in FIG. 26A. In addition to showing the hourly urine output 2602 (in mL), the first hydration fluid infusion rate 604 (in mL/hr), and the second hydration fluid infusion rate 2606 from FIG. 26A, FIG. 26B also includes a plot of first total saline infusion 2612 (in ml) based on the patient's (unadjusted) urine output rate and a plot of second total saline infusion 2614 (in ml) based on the patient's adjusted urine output rate and/or sodium output rate. As shown in FIG. 26B, at the end of treatment the second total saline infusion 2614 was less than the first total saline infusion 2612, meaning that providing fluid therapy based on the patient's adjusted urine output rate and/or sodium output rate led to less saline being infused over the course of fluid therapy than providing fluid therapy based on the patient's (unadjusted) urine output rate.

VI. CONCLUSION

It will be apparent to those having skill in the art that changes may be made to the details of the above-described embodiments without departing from the underlying principles of the present disclosure. For example, although certain embodiments of the present technology are described as utilizing a patient's urine sodium levels (see, e.g., block 502 in FIG. 5A), it will be apparent to those having skill in the art that embodiments of the present technology can also utilize the level of one or more other electrolytes and/or charged particles or compounds (e.g., chloride) in the patient's urine, in addition to or instead of the patient's urine sodium levels. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Where context permits, singular or plural terms may also include the plural or singular term, respectively. In addition, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded. Moreover, as used herein, the phrases "based on," "depends on," "as a result of," and "in response to" shall not be construed as a reference to a closed set of conditions. For example, an exemplary step that is described as "based on condition A" may be based on both condition A and condition B without departing from the scope of the present disclosure. In other words, as used herein, the phrase "based on" shall be construed in the same manner as the phrase "based at least in part on" or the phrase "based at least partially on."

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing concentrations, rates, volumes, and/or combinations thereof, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10. As another example, a set of values of "at least 1, 5, or 10" includes any and all subvalues therebetween, e.g., 2, 3, 6.5, etc.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

VII. EXAMPLES

The present technology is illustrated, for example, according to various aspects described below as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. A method for providing fluid therapy, the method comprising:
   receiving a sodium excretion input for the patient;
   receiving a urine output rate;
   determining an adjusted urine output rate based on the sodium excretion input and the urine output rate; and
   providing fluid therapy based on the adjusted urine output rate.

2. The method of any one of the clauses herein, wherein determining the adjusted urine output rate is further based on a predetermined urine sodium concentration for a group of patients.

3. The method of any one of the clauses herein, wherein determining the adjusted urine output rate is based on a relative difference between the sodium excretion input for the patient and a predetermined urine sodium concentration for a group of patients.

4. The method of any one of the clauses herein, wherein determining the adjusted urine output rate is based on a relative difference between the sodium excretion input for the patient and a predetermined urine sodium concentration for a group of patients, and wherein the predetermined urine sodium concentration is at least 140 mmol/L.

5. The method of any one of the clauses herein, wherein determining the adjusted urine output rate comprises:
dividing the sodium excretion input for the patient by a predetermined urine sodium concentration for a group of patients to produce a weighted value, and
multiplying the weighted value by the urine output rate to determine the adjusted urine output rate.

6. The method of any one of the clauses herein, wherein determining the adjusted urine output rate comprises:
determining the sodium excretion input is greater than a max threshold urine sodium level, and
determining the adjusted urine output rate based, at least in part, on the max threshold urine sodium level.

7. The method of any one of the clauses herein, wherein determining the adjusted urine output rate comprises:
determining the sodium excretion input is less than a minimum threshold urine sodium level, and
determining the adjusted urine output rate based, at least in part, on the minimum threshold urine sodium level.

8. The method of any one of the clauses herein, wherein providing fluid therapy comprises:
before receiving the sodium excretion input, providing a hydration fluid at a hydration fluid infusion rate; and
after receiving the sodium excretion input, adjusting the hydration fluid infusion rate based on the sodium excretion input.

9. The method of any one of the clauses herein, wherein providing fluid therapy comprises:
before receiving the sodium excretion input, providing a hydration fluid at a hydration fluid infusion rate; and
after receiving the sodium excretion input, adjusting the hydration fluid infusion rate based on the adjusted urine output rate.

10. The method of any one of the clauses herein, wherein providing fluid therapy comprises:
before receiving the sodium excretion input, providing a diuretic at a diuretic dosage rate; and
after receiving the sodium excretion input, adjusting the diuretic dosage rate based on the sodium excretion input.

11. The method of any one of the clauses herein, wherein providing fluid therapy comprises:
before receiving the sodium excretion input, providing a diuretic at a diuretic dosage rate; and
after receiving the sodium excretion input, adjusting the diuretic dosage rate based on the adjusted urine output rate.

12. The method of any one of the clauses herein, wherein the sodium excretion input comprises a rate, a concentration, or an amount.

13. A method for providing fluid therapy, the method comprising:
receiving a sodium excretion input for the patient;
receiving a urine output rate;
determining an adjusted urine output rate based on the sodium excretion input and the urine output rate; and
determining a dose finding urine rate threshold based on the adjusted urine output rate.

14. The method of clause 13, further comprising:
before the adjusted urine output rate is equal to or greater than the dose finding urine rate threshold, increasing a diuretic dosage rate from a first diuretic dosage rate to a second diuretic dosage rate, and
after the adjusted urine output rate is equal to or greater than the dose finding urine rate threshold, administering diuretic at a third diuretic dosage rate based, at least in part, on the second diuretic dosage rate.

15. A method for providing fluid therapy, the method comprising:
receiving a sodium excretion input for the patient;
receiving a urine output rate;
determining an adjusted urine output rate based on the sodium excretion input and the urine output rate; and
determining a low urine rate threshold based on the adjusted urine output rate.

16. The method of clause 15, further comprising:
before the adjusted urine output rate is less than or equal to than the low urine rate threshold, causing diuretic to be administered to the patient a first diuretic dosage rate, and
after the adjusted urine output rate is less than or equal to the low urine rate threshold, causing diuretic to be administered to the patient at a second diuretic dosage rate greater than the first diuretic dosage rate.

17. A method for providing fluid therapy, the method comprising:
receiving a sodium excretion input for the patient;
receiving a urine output rate;
determining an adjusted urine output rate based on the sodium excretion input and the urine output rate; and
determining a high urine rate threshold based on the adjusted urine output rate.

18. The method of clause 17, further comprising:
before the adjusted urine output rate is equal to or greater than the high urine rate threshold, causing diuretic to be administered to the patient a first diuretic dosage rate, and
after the adjusted urine output rate is equal to or greater than the high urine rate threshold, causing diuretic to be administered to the patient at a second diuretic dosage rate less than the first diuretic dosage rate when the adjusted urine output rate remains equal to or greater than the high urine rate threshold for a predetermined amount of time.

19. A method for providing fluid therapy, the method comprising:
receiving a sodium excretion input for the patient;
receiving a urine output rate;
determining an adjusted urine output rate based on the sodium excretion input and the urine output rate; and
determining a desired sodium excretion rate based on the adjusted urine output rate.

20 The method of any one of the clauses herein.

21 The method of any one of the clauses herein wherein the desired sodium excretion rate is a target sodium excretion rate at the dose finding diuretic rate threshold.

22. The method of any one of the clauses herein wherein the desired sodium excretion rate is a target sodium excretion rate at the low urine rate threshold.

23. The method of any one of the clauses herein wherein the desired sodium excretion rate is a target sodium excretion rate at the high urine rate threshold.

24. The method of any one of the clauses herein wherein the adjusted urine output rate is further based on a chloride and/or other electrolyte excretion input for the patient.

25. A method for providing fluid therapy, the method comprising:
receiving an electrolyte excretion input for the patient;
receiving a urine output rate;

determining an adjusted urine output rate based on the electrolyte excretion input and the urine output rate; and providing fluid therapy based on the adjusted urine output rate.

26 The method of any one of the clauses herein wherein the electrolyte excretion input includes a sodium excretion input.

27. The method of any one of the clauses herein wherein the electrolyte excretion input includes a chloride excretion input.

28. A fluid therapy system, comprising:
one or more processors; and
tangible, non-transitory computer-readable media having instructions that, when executed by the one or more processors, cause the fluid therapy system to perform operations to cause a net fluid loss from a patient, the operations comprising—
obtaining a sodium excretion input for the patient;
obtaining a urine output rate for the patient;
determining an adjusted urine output rate for the patient based on the sodium excretion input and the urine output rate;
receiving a first indication that the adjusted urine output rate is at or above a first urine output threshold and below a second urine output threshold,
after receiving the first indication, causing hydration fluid to be infused to the patient at a first hydration fluid rate, such that a first difference exists between the first hydration fluid rate and the adjusted urine output rate of the patient when the first indication is received, wherein the first hydration fluid rate is less than a first predetermined rate while the adjusted urine output rate is below the second urine output threshold;
receiving a second indication that the adjusted urine output rate is at or above the second urine output threshold; and
after receiving the second indication, causing the hydration fluid to be infused at a second hydration fluid rate at or above the first hydration fluid rate, such that a second difference exists between the second hydration fluid rate and the adjusted urine output rate when the second indication is received, wherein the second difference is greater than the first difference, and wherein the second hydration fluid rate is less than the adjusted urine output rate.

29. The fluid therapy system of clause 28, wherein:
when the adjusted urine output rate of the patient is between the first urine output threshold and the second urine output threshold, the adjusted urine output rate is greater than the first hydration fluid rate by a first amount,
when the adjusted urine output rate of the patient is between the second urine output threshold and a third urine output threshold greater than the second urine output threshold, the adjusted urine output rate is greater than the second hydration fluid rate by a second amount, and
the second amount is greater than the first amount.

30 The fluid therapy system of clause 28 or clause 29, wherein the operations further comprise:
receiving a third indication that the adjusted urine output rate is at or above a third urine output threshold, wherein the third urine output threshold is above the second urine output threshold; and after receiving the third indication, causing the hydration fluid to be infused at a third hydration fluid rate at or above the second hydration fluid rate.

31. The fluid therapy system of clause 30, wherein:
causing the hydration fluid to be infused at the first hydration fluid rate is configured to correspond to a first net fluid balance of the patient,
causing the hydration fluid to be infused at the second hydration fluid rate is configured to correspond to a second net fluid balance of the patient less than the first net fluid balance, and
causing the hydration fluid to be infused at the third hydration fluid rate is configured to correspond to a third net fluid balance of the patient less than the second net fluid balance.

32. The fluid therapy system of clause 30 or clause 31, wherein the operations further comprise:
receiving a fourth indication that the adjusted urine output rate is at or above a fourth urine output threshold, wherein the fourth urine output threshold is above the third urine output threshold; and
after receiving the fourth indication, causing the hydration fluid to be infused at a fourth hydration fluid rate at or above the third hydration fluid rate.

33. The fluid therapy system of any of clauses 30-32, wherein the first urine output threshold is at least 175 milliliters/hour, and the second urine output threshold is at least 375 milliliters/hour.

34 The fluid therapy system of any of clauses 28-33, further comprising a first pump configured to provide the hydration fluid to the patient and a second pump configured to provide a diuretic to the patient.

35. The fluid therapy system of any of clauses 28-35, wherein the operations further comprise, when the adjusted urine output rate is below the first urine output threshold, not causing the hydration fluid to be infused.

36. The fluid therapy system of any of clauses 28-35, further comprising, prior to causing the hydration fluid to be infused to the patient at the first hydration fluid rate, causing the hydration fluid to be infused to the patient at an initial infusion rate, wherein the first hydration fluid rate is higher than the initial infusion rate.

37. The fluid therapy system of any of clauses 28-36, wherein determining the adjusted urine output rate is further based on a predetermined urine sodium concentration for a group of patients.

38. The fluid therapy system of any of clauses 28-37, wherein determining the adjusted urine output rate is based on a relative difference between the sodium excretion input for the patient and a predetermined urine sodium concentration for a group of patients.

39. The fluid therapy system of any of clauses 28-38, wherein determining the adjusted urine output rate is based on a relative difference between the sodium excretion input for the patient and a predetermined urine sodium concentration for a group of patients, and wherein the predetermined urine sodium concentration is at least 140 mmol/L.

40. The fluid therapy system of any of clauses 28-39, wherein determining the adjusted urine output rate comprises:
dividing the sodium excretion input for the patient by a predetermined urine sodium concentration for a group of patients to produce a weighted value, and
multiplying the weighted value by the urine output rate to determine the adjusted urine output rate.

41. The fluid therapy system of any of clauses 28-40, wherein determining the adjusted urine output rate comprises:
  determining the sodium excretion input is greater than a max threshold urine sodium level, and
  determining the adjusted urine output rate based, at least in part, on the max threshold urine sodium level.

42. The fluid therapy system of any of clauses 28-41, wherein determining the adjusted urine output rate comprises:
  determining the sodium excretion input is less than a minimum threshold urine sodium level, and
  determining the adjusted urine output rate based, at least in part, on the minimum threshold urine sodium level.

43. A method for providing fluid therapy, the method comprising:
  obtaining a sodium excretion input for a patient;
  obtaining a urine output rate for the patient;
  determining an adjusted urine output rate for the patient based on the sodium excretion input and the urine output rate;
  receiving a first indication that an adjusted urine output rate of a patient is at or above a first urine output threshold and below a second urine output threshold;
  after receiving the first indication, causing hydration fluid to be infused to the patient at a first hydration fluid rate, such that a first difference exists between the first hydration fluid rate and the adjusted urine output rate of the patient when the first indication is received, wherein the first hydration fluid rate is less than a first predetermined rate while the adjusted urine output rate is below the second urine output threshold;
  receiving a second indication that the adjusted urine output rate is at or above the second urine output threshold; and
  after receiving the second indication, causing the hydration fluid to be infused at a second hydration fluid rate at or above the first hydration fluid rate, such that a second difference exists between the second hydration fluid rate and the adjusted urine output rate when the second indication is received, wherein the second difference is greater than the first difference, and wherein the second hydration fluid rate is less than the adjusted urine output rate.

44. The method of clause 43, wherein determining the adjusted urine output rate is further based on a predetermined urine sodium concentration for a group of patients.

45. The method of clause 43 or clause 44, wherein determining the adjusted urine output rate is based on a relative difference between the sodium excretion input for the patient and a predetermined urine sodium concentration for a group of patients.

46. The method of any of clauses 43-45, wherein determining the adjusted urine output rate is based on a relative difference between the sodium excretion input for the patient and a predetermined urine sodium concentration for a group of patients, and wherein the predetermined urine sodium concentration is at least 140 mmol/L.

47. The method of any of clauses 43-46, wherein determining the adjusted urine output rate comprises:
  dividing the sodium excretion input for the patient by a predetermined urine sodium concentration for a group of patients to produce a weighted value, and
  multiplying the weighted value by the urine output rate to determine the adjusted urine output rate.

48. The method of any of clauses 43-47, wherein determining the adjusted urine output rate comprises:
  determining the sodium excretion input is greater than a max threshold urine sodium level, and
  determining the adjusted urine output rate based, at least in part, on the max threshold urine sodium level.

49. The method of any of clauses 43-48, wherein determining the adjusted urine output rate comprises:
  determining the sodium excretion input is less than a minimum threshold urine sodium level, and
  determining the adjusted urine output rate based, at least in part, on the minimum threshold urine sodium level.

50. The method of any of clauses 43-49, wherein:
  when the adjusted urine output rate of the patient is between the first urine output threshold and the second urine output threshold, the adjusted urine output rate is greater than the first hydration fluid rate by a first amount,
  when the adjusted urine output rate of the patient is between the second urine output threshold and a third urine output threshold greater than the second urine output threshold, the adjusted urine output rate is greater than the second hydration fluid rate by a second amount, and
  the second amount is greater than the first amount.

51. The method of any of clauses 43-50, further comprising:
  receiving a third indication that the adjusted urine output rate is at or above a third urine output threshold, wherein the third urine output threshold is above the second urine output threshold; and
  after receiving the third indication, causing the hydration fluid to be infused at a third hydration fluid rate at or above the second hydration fluid rate.

52. The method of clause 51, wherein:
  causing the hydration fluid to be infused at the first hydration fluid rate is configured to correspond to a first net fluid balance of the patient,
  causing the hydration fluid to be infused at the second hydration fluid rate is configured to correspond to a second net fluid balance of the patient less than the first net fluid balance, and
  causing the hydration fluid to be infused at the third hydration fluid rate is configured to correspond to a third net fluid balance of the patient less than the second net fluid balance.

53. The method of clause 51 or clause 52, further comprising:
  receiving a fourth indication that the adjusted urine output rate is at or above a fourth urine output threshold, wherein the fourth urine output threshold is above the third urine output threshold; and
  after receiving the fourth indication, causing the hydration fluid to be infused at a fourth hydration fluid rate at or above the third hydration fluid rate.

54. The method of any of clauses 51-53, wherein the first urine output threshold is at least 175 milliliters/hour, and the second urine output threshold is at least 375 milliliters/hour.

55. The method of any of clauses 43-54, further comprising a first pump configured to provide the hydration fluid to the patient and a second pump configured to provide a diuretic to the patient.

56. The method of any of clauses 43-55, further comprising, when the adjusted urine output rate is below the first urine output threshold, not causing the hydration fluid to be infused.

57. The method of any of clauses 43-56, further comprising, prior to causing the hydration fluid to be infused to the patient at the first hydration fluid rate, causing the hydration fluid to be infused to the patient at an initial infusion rate, wherein the first hydration fluid rate is higher than the initial infusion rate.

58. A fluid therapy system, comprising:
  a urine measurement device configured to measure urine output of a patient;
  a diuretic source configured to provide a diuretic to the patient;
  a hydration fluid source configured to provide a hydration fluid to the patient; and
  a controller, wherein the controller is configured to—
    obtain, via the urine measurement device, a urine output rate of the patient;
    obtain a sodium excretion input for the patient;
    determine an adjusted urine output rate based on the sodium excretion input and the urine output rate; and
    based on the adjusted urine output rate, (i) cause the diuretic to be administered to the patient at one or more diuretic dosage rates and (ii) cause the hydration fluid to be administered to the patient at one or more hydration rates to produce a net fluid loss in the patient.

59. The fluid therapy system of clause 58, wherein the controller is further configured to:
  determine, based at least in part on a ratio of the urine output rate to the adjusted urine output rate, one or more thresholds associated with the administration of the hydration fluid and/or the diuretic to the patient; and
  cause the diuretic and/or the hydration fluid to be administered, and/or cause an adjustment to the one or more diuretic dosage rates and/or the one or more hydration rates, based at least in part on the one or more thresholds.

60. The fluid therapy system of clause 58 or clause 59, wherein the adjusted urine output rate is further based on a predetermined urine sodium concentration for a group of patients.

61. The fluid therapy system of any of clauses 58-60, wherein the adjusted urine output rate is further based on a relative difference between the sodium excretion input for the patient and a predetermined urine sodium concentration for a group of patients.

62. The fluid therapy system of any of clauses 58-61, wherein the adjusted urine output rate is further based on a relative difference between the sodium excretion input for the patient and a predetermined urine sodium concentration for a group of patients, and wherein the predetermined urine sodium concentration is at least 140 mmol/L.

63. The fluid therapy system of any of clauses 58-62, wherein, to determine the adjusted urine output rate, the controller is configured to:
  divide the sodium excretion input for the patient by a predetermined urine sodium concentration for a group of patients to produce a weighted value, and
  multiply the weighted value by the urine output rate to determine the adjusted urine output rate.

64 The fluid therapy system of any of clauses 58-63, wherein, to determine the adjusted urine output rate, the controller is configured to:
  determine the sodium excretion input is greater than a max threshold urine sodium level, and
  determine the adjusted urine output rate based, at least in part, on the max threshold urine sodium level.

65. The fluid therapy system of any of clauses 58-64, wherein, to determine the adjusted urine output rate, the controller is configured to:
  determine the sodium excretion input is less than a minimum threshold urine sodium level, and
  determine the adjusted urine output rate based, at least in part, on the minimum threshold urine sodium level.

66. The fluid therapy system of any of clauses 58-65, wherein:
  before receiving the sodium excretion input, the controller is configured to provide the hydration fluid at a hydration fluid infusion rate; and
  after receiving the sodium excretion input, the controller is configured to adjust the hydration fluid infusion rate based on the adjusted urine output rate.

67. The fluid therapy system of any of clauses 58-66, wherein:
  before receiving the sodium excretion input, the controller is configured to provide the diuretic at a diuretic dosage rate; and
  after receiving the sodium excretion input, the controller is configured to adjust the diuretic dosage rate based on the adjusted urine output rate.

68. The fluid therapy system of any of clauses 58-67, wherein the sodium excretion input comprises a rate, a concentration, or an amount.

69. The fluid therapy system of any of clauses 58-68, further comprising a user interface, wherein the controller is configured to obtain the sodium excretion input for the patient from a user input via the user interface.

70. The fluid therapy system of any of clauses 58-69, further comprising a sensor configured to detect a level of sodium in the urine output from the patient, wherein the controller is configured to obtain the sodium excretion input for the patient based at least in part on the level of sodium detected via the sensor.

71. The fluid therapy system of any of clauses 58-70, wherein the controller is further configured to:
  determine a desired sodium excretion rate for the patient based at least in part on the adjusted urine output rate; and
  cause (i) the diuretic to be administered to the patient at the one or more diuretic dosage rates and/or (ii) the hydration fluid to be administered to the patient at the one or more hydration rates to cause a sodium excretion rate for the patient to equal or exceed the desired sodium excretion rate.

72. The fluid therapy system of clause 71, wherein the desired sodium excretion rate is a minimum sodium excretion rate associated with a net fluid loss goal for the patient.

73. A method for providing fluid therapy to a patient, the method comprising:
  obtaining a urine output rate for the patient;
  obtaining a sodium excretion input for the patient;
  determining an adjusted urine output rate based on the sodium excretion input and the urine output rate; and
  based on the adjusted urine output rate, (i) causing a diuretic to be administered to the patient at one or more diuretic dosage rates and (ii) causing a hydration fluid to be administered to the patient at one or more hydration rates to produce a net fluid loss in the patient.

74 The method of clause 73, further comprising:
  determining one or more thresholds associated with the administration of the hydration fluid and/or the diuretic based at least in part on a ratio of the urine output rate to the adjusted urine output rate,
  wherein causing the diuretic and the hydration fluid to be administered includes causing the hydration fluid and/or the diuretic to be administered, and/or causing an adjustment to the one or more diuretic dosage rates and/or the one or more hydration rates, based at least in part on the one or more thresholds.

75. The method of clause 73 or clause 74, wherein determining the adjusted urine output rate is further based on a predetermined urine sodium concentration for a group of patients.

76. The method of any of clauses 73-75, wherein determining the adjusted urine output rate is further based on a relative difference between the sodium excretion input for the patient and a predetermined urine sodium concentration for a group of patients.

77. The method of any of clauses 73-76, wherein determining the adjusted urine output rate is further based on a relative difference between the sodium excretion input for the patient and a predetermined urine sodium concentration for a group of patients, and wherein the predetermined urine sodium concentration is at least 140 mmol/L.

78. The method of any of clauses 73-77, wherein determining the adjusted urine output rate comprises:
dividing the sodium excretion input for the patient by a predetermined urine sodium concentration for a group of patients to produce a weighted value, and
multiplying the weighted value by the urine output rate to determine the adjusted urine output rate.

79. The method of any of clauses 73-78, wherein determining the adjusted urine output rate comprises:
determining the sodium excretion input is greater than a max threshold urine sodium level, and
determining the adjusted urine output rate based, at least in part, on the max threshold urine sodium level.

80. The method of any of clauses 73-79, wherein determining the adjusted urine output rate comprises:
determining the sodium excretion input is less than a minimum threshold urine sodium level, and
determining the adjusted urine output rate based, at least in part, on the minimum threshold urine sodium level.

81. The method of any of clauses 73-80, wherein causing the hydration fluid to be administered to the patient at the one or more hydration rates comprises:
before receiving the sodium excretion input, causing the hydration fluid to be administered to the patient at a hydration fluid infusion rate; and
after receiving the sodium excretion input, causing an adjustment to the hydration fluid infusion rate based on the adjusted urine output rate.

82 The method of any of clauses 73-81, wherein causing the diuretic to be administered to the patient at the one or more diuretic dosage rates comprises:
before receiving the sodium excretion input, causing the diuretic to be administered at a diuretic dosage rate; and
after receiving the sodium excretion input, causing an adjustment to the diuretic dosage rate based on the adjusted urine output rate.

83. The method of any of clauses 73-82, wherein obtaining the sodium excretion input comprises obtaining a rate, a concentration, or an amount associated with a level of sodium in the patient's urine.

84. The method of any of clauses 73-83, wherein obtaining the sodium excretion input includes obtaining the sodium excretion input from a user via a user interface.

85. The method of any of clauses 73-84, wherein obtaining the sodium excretion input incudes obtaining the sodium excretion input via a sensor configured to detect a level of sodium in the patient's urine.

86. The method of any of clauses 73-85, further comprising:
determining a desired sodium excretion rate for the patient based at least in part on the adjusted urine output rate;
wherein—
causing the diuretic to be administered to the patient at the one or more diuretic dosage rates includes causing the diuretic to be administered at one or more diuretic dosage rate to produce the desired sodium excretion rate; and/or
causing the hydration fluid to be administered to the patient at the one or more hydration rates includes causing the hydration fluid to be administered at one or more hydration rates to produce the desired sodium excretion rate.

87. The method of clause 86, wherein the desired sodium excretion rate is a minimum sodium excretion rate associated with a net fluid loss goal for the patient.

88. A fluid therapy system, comprising:
a diuretic source configured to provide a diuretic to the patient;
a hydration fluid source configured to provide a hydration fluid to the patient; and
a controller, wherein the controller is configured to—
obtain a sodium excretion input for the patient;
determine a sodium output rate based at least in part on the sodium excretion input; and
based on the sodium output rate, (i) cause the diuretic to be administered to the patient at one or more diuretic dosage rates and (ii) cause the hydration fluid to be administered to the patient at one or more hydration rates to produce a net fluid loss in the patient.

89 The fluid therapy system of clause 88, further comprising a urine measurement device configured to measure urine output of the patient, wherein the controller is further configured to determine the sodium output rate based at least in part on the sodium excretion input and a urine output rate obtained via the urine measurement device.

90. The fluid therapy system of clause 88 or clause 89, wherein the controller is further configured to:
compare the sodium excretion input with one or more sodium output rate thresholds associated with the administration of the hydration fluid and/or the diuretic to the patient; and
cause the diuretic and/or the hydration fluid to be administered and/or cause an adjustment to the administration of the diuretic and/or the hydration fluid based at least in part on the comparison.

91. The fluid therapy system of any of clauses 88-90, wherein the sodium excretion input includes a conductivity of the patient's urine.

92. The fluid therapy system of any of clauses 88-91, wherein the sodium excretion input includes a concentration of sodium in the patient's urine.

93. The fluid therapy system of any of clauses 88-92, wherein:
before receiving the sodium excretion input, the controller is configured to provide the hydration fluid at a hydration fluid infusion rate; and
after receiving the sodium excretion input, the controller is configured to adjust the hydration fluid infusion rate based on the sodium output rate.

94 The fluid therapy system of any of clauses 88-93, wherein:
before receiving the sodium excretion input, the controller is configured to provide the diuretic at a diuretic dosage rate; and after receiving the sodium excretion input, the controller is configured to adjust the diuretic dosage rate based on the sodium output rate.

95. The fluid therapy system of any of clauses 88-94, further comprising a user interface, wherein the controller is configured to obtain the sodium excretion input for the patient from a user input via the user interface.

96. The fluid therapy system of any of clauses 88-95, further comprising a sensor configured to detect a sodium concentration in urine output from the patient, wherein the controller is configured to obtain the sodium excretion input for the patient based at least in part on the sodium concentration detected via the sensor.

97. The fluid therapy system of any of clauses 88-96, wherein, during a first time period, the controller is configured to provide fluid therapy based on an assumed sodium excretion input and, during a second time period after the first time period, the controller is configured to obtain the sodium excretion input for the patient.

98. The fluid therapy system of clause 97, wherein the assumed sodium excretion input is an assumed sodium excretion based at least in part on a measured urine output rate for the patient and an assumed concentration of sodium in the patient's urine.

99. The fluid therapy system of clause 98, wherein the assumed concentration of sodium is 140 mmol/L.

100. The fluid therapy system of any of clauses 88-99, wherein the controller is configured to obtain a sodium loss based on the sodium output rate and cause an amount the hydration fluid to be administered to replace a percentage of the sodium loss.

101. The fluid therapy system of clause 100, wherein the percentage is up to 50% of the sodium loss.

102. A method for providing fluid therapy to a patient, the method comprising:
 obtaining a sodium excretion input for the patient;
 determining a sodium output rate based at least in part on the sodium excretion input; and
 based on the sodium output rate, (i) causing a diuretic to be administered to the patient at one or more diuretic dosage rates and (ii) causing a hydration fluid to be administered to the patient at one or more hydration rates to produce a net fluid loss in the patient.

103. The method of clause 102, further comprising obtaining a urine output rate for the patient, wherein determining the sodium output rate includes determining the sodium output rate based at least in part on the sodium excretion input and the urine output rate.

104. The method of clause 102 or clause 103, wherein determining the sodium excretion input includes a conductivity of the patient's urine.

105. The method of any of clauses 102-104, wherein obtaining the sodium excretion input includes obtaining a concentration of sodium in the patient's urine.

106. The method of any of clauses 102-105, wherein obtaining the sodium excretion input includes obtaining the sodium excretion input from a user via a user interface.

107. The method of any of clauses 102-106, wherein obtaining the sodium excretion input incudes obtaining the sodium excretion input via a sensor configured to detect a level of sodium in the patient's urine.

108. The method of any of clauses 102-107, wherein obtaining the sodium excretion input includes:
 collecting urine within a collection container of a fluid therapy system;
 removing a urine sample from the urine collected within the collection container;
 measuring a concentration of sodium in the urine sample; and
 causing a processor of the fluid therapy system to obtain the concentration.

109. The method of clause 108 wherein causing the processor to obtain the concentration includes inputtting the concentration via a user interface of the fluid therapy system.

110. The method of any of clauses 102-109, wherein, during a first time period, the method comprises causing the hydration fluid and/or the diuretic to be administered at one or more first rates that are based at least in part on an assumed sodium excretion input and, during a second time period after the first time period, the method comprises causing the hydration fluid and/or the diuretic to be administered at one or more second rates that are based at least in part on the obtained sodium excretion input for the patient.

111. The method of clause 110, wherein the assumed sodium excretion input is an assumed sodium excretion based at least in part on an obtained urine output rate for the patient and an assumed concentration of sodium in the patient's urine.

112. The method of clause 110 or clause 111 wherein the first time period is up to 6 hours.

113. The method of any of clauses 110-112 wherein the first time period includes an amount of time before the patient has output a predetermined quantity of urine.

114. The method of any of clauses 110-113 wherein the first time period includes an amount of time before the patient has output at least 1 liter of urine.

115. The method of any of clauses 102-114 wherein (i) causing the diuretic to be administered to the patient at the one or more diuretic dosage rates and/or (ii) causing the hydration fluid to be administered to the patient at the one or more hydration rates includes causing the diuretic and/or the hydration fluid to be administered to produce a net sodium loss in the patient.

116. The method of any of clauses 102-115 wherein causing the hydration fluid to be administered includes replacing a percentage of the sodium lost from the patient via urine during fluid therapy.

117. The method of clause 116, wherein the percentage is up to 50% of the sodium lost from the patient via urine during fluid therapy.

We claim:
1. A fluid therapy system, comprising:
 a diuretic source configured to provide a diuretic to a patient;
 a hydration fluid source configured to provide a hydration fluid to the patient; and
 a controller, wherein the controller is configured to—
  during a first time period, provide fluid therapy based on an assumed sodium excretion input; and
  during a second time period after the first time period—
   obtain a sodium excretion input for the patient;
   determine a sodium output rate based at least in part on the sodium excretion input; and
   based on the sodium output rate, (i) cause the diuretic to be administered to the patient at one or more diuretic dosage rates and (ii) cause the hydration fluid to be administered to the patient at one or more hydration rates to produce a net fluid loss in the patient.

2. The fluid therapy system of claim 1, further comprising a urine measurement device configured to measure urine output of the patient, wherein the controller is further configured to determine the sodium output rate based at least in part on the sodium excretion input and a urine output rate obtained via the urine measurement device.

3. The fluid therapy system of claim 1, wherein the controller is further configured to:
compare the sodium excretion input with one or more sodium output rate thresholds associated with the administration of the hydration fluid and/or the diuretic to the patient; and
cause the diuretic and/or the hydration fluid to be administered and/or cause an adjustment to the administration of the diuretic and/or the hydration fluid based at least in part on the comparison.

4. The fluid therapy system of claim 1, wherein the sodium excretion input includes a conductivity of the patient's urine.

5. The fluid therapy system of claim 1, wherein the sodium excretion input includes a concentration of sodium in the patient's urine.

6. The fluid therapy system of claim 1, wherein:
before receiving the sodium excretion input, the controller is configured to provide the hydration fluid at a hydration fluid infusion rate; and
after receiving the sodium excretion input, the controller is configured to adjust the hydration fluid infusion rate based on the sodium output rate.

7. The fluid therapy system of claim 1, wherein:
before receiving the sodium excretion input, the controller is configured to provide the diuretic at a diuretic dosage rate; and
after receiving the sodium excretion input, the controller is configured to adjust the diuretic dosage rate based on the sodium output rate.

8. The fluid therapy system of claim 1, further comprising a user interface, wherein the controller is configured to obtain the sodium excretion input for the patient from a user input via the user interface.

9. The fluid therapy system of claim 1, further comprising a sensor configured to detect a sodium concentration in urine output from the patient, wherein the controller is configured to obtain the sodium excretion input for the patient based at least in part on the sodium concentration detected via the sensor.

10. The fluid therapy system of claim 1, wherein the assumed sodium excretion input is an assumed sodium excretion based at least in part on a measured urine output rate for the patient and an assumed concentration of sodium in the patient's urine.

11. The fluid therapy system of claim 10, wherein the assumed concentration of sodium is 140 mmol/L.

12. The fluid therapy system of claim 1, wherein the controller is configured to obtain a sodium loss based on the sodium output rate and cause an amount the hydration fluid to be administered to replace a percentage of the sodium loss.

13. The fluid therapy system of claim 12, wherein the percentage is up to 50% of the sodium loss.

14. A method for providing fluid therapy to a patient, the method comprising:
during a first time period, causing a hydration fluid and/or a diuretic to be administered to the patient at one or more rates that are based at least in part on an assumed sodium excretion input for the patient; and
during a second time period after the first time period—
obtaining a sodium excretion input for the patient;
determining a sodium output rate based at least in part on the sodium excretion input; and
based on the sodium output rate, (i) causing the diuretic to be administered to the patient at one or more diuretic dosage rates and (ii) causing the hydration fluid to be administered to the patient at one or more hydration rates to produce a net fluid loss in the patient.

15. The method of claim 14, further comprising obtaining a urine output rate for the patient, wherein determining the sodium output rate includes determining the sodium output rate based at least in part on the sodium excretion input and the urine output rate.

16. The method of claim 14, wherein determining the sodium excretion input includes determining a conductivity of the patient's urine.

17. The method of claim 14, wherein obtaining the sodium excretion input includes obtaining a concentration of sodium in the patient's urine.

18. The method of claim 14, wherein obtaining the sodium excretion input includes obtaining the sodium excretion input from a user via a user interface.

19. The method of claim 14, wherein obtaining the sodium excretion input incudes obtaining the sodium excretion input via a sensor configured to detect a level of sodium in the patient's urine.

20. The method of claim 14, wherein obtaining the sodium excretion input includes:
collecting urine within a collection container of a fluid therapy system;
removing a urine sample from the urine collected within the collection container;
measuring a concentration of sodium in the urine sample; and
causing a processor of the fluid therapy system to obtain the concentration.

21. The method of claim 20 wherein causing the processor to obtain the concentration includes inputting the concentration via a user interface of the fluid therapy system.

22. The method of claim 14, wherein the assumed sodium excretion input is an assumed sodium excretion based at least in part on an obtained urine output rate for the patient and an assumed concentration of sodium in the patient's urine.

23. The method of claim 14 wherein the first time period is up to 6 hours.

24. The method of claim 14 wherein the first time period includes an amount of time before the patient has output a predetermined quantity of urine.

25. The method of claim 14 wherein the first time period includes an amount of time before the patient has output at least 1 liter of urine.

26. The method of claim 14 wherein (i) causing the diuretic to be administered to the patient at the one or more diuretic dosage rates and/or (ii) causing the hydration fluid to be administered to the patient at the one or more hydration rates includes causing the diuretic and/or the hydration fluid to be administered to produce a net sodium loss in the patient.

27. The method of claim 14 wherein causing the hydration fluid to be administered includes replacing a percentage of the sodium lost from the patient via urine during fluid therapy.

28. The method of claim 27, wherein the percentage is up to 50% of the sodium lost from the patient via urine during fluid therapy.

* * * * *

UNITED STATES PATENT AND TRADEMARK OFFICE
CERTIFICATE OF CORRECTION

| | |
|---|---|
| PATENT NO. | : 12,257,416 B1 |
| APPLICATION NO. | : 18/883857 |
| DATED | : March 25, 2025 |
| INVENTOR(S) | : Andrew V. Halpert et al. |

It is certified that error appears in the above-identified patent and that said Letters Patent is hereby corrected as shown below:

On the Title Page

On the page 2, in Column 2, under "U.S. Patent Documents", Line 22, delete "Gelfand" and insert -- Gelfand et al. --.

On the page 4, in Column 2, under "Other Publications", Line 14, delete "Pharmcokinetics," and insert -- Pharmacokinetics, --.

On the page 4, in Column 2, under "Other Publications", Line 21, delete "Urogyecologyl" and insert -- Urogynecology --.

On the page 5, in Column 1, under "Other Publications", Line 1, delete "Furosmide" and insert -- Furosemide --.

On the page 5, in Column 1, under "Other Publications", Line 3, delete "Univeristy" and insert -- University --.

In the Specification

In Column 34, Line 20, delete "5A" and insert -- 5A. --.

In Column 45, Line 66, delete "necessary," and insert -- necessary. --.

In Column 50, Line 32, delete "If" and insert -- if --.

In Column 62, Line 51, delete "20" and insert -- 20. --.

In Column 62, Line 52, delete "21" and insert -- 21. --.

In Column 63, Line 6, delete "26" and insert -- 26. --.

Signed and Sealed this
Fifteenth Day of July, 2025

Coke Morgan Stewart
*Acting Director of the United States Patent and Trademark Office*

CERTIFICATE OF CORRECTION (continued)
U.S. Pat. No. 12,257,416 B1

In Column 63, Line 62, delete "30" and insert -- 30. --.

In Column 64, Line 30 (approx.), delete "34" and insert -- 34. --.

In Column 67, Line 58, delete "64" and insert -- 64. --.

In Column 68, Line 59, delete "74" and insert -- 74. --.

In Column 69, Line 47, delete "82" and insert -- 82. --.

In Column 69, Line 63, delete "incudes" and insert -- includes --.

In Column 70, Line 33, delete "89" and insert -- 89. --.

In Column 70, Line 63, delete "94" and insert -- 94. --.

In Column 71, Line 59, delete "incudes" and insert -- includes --.

In the Claims

In Column 74, Line 22 (approx.), in Claim 19, delete "incudes" and insert -- includes --.